(12) United States Patent
Low et al.

(10) Patent No.: US 11,162,937 B2
(45) Date of Patent: Nov. 2, 2021

(54) PATIENT SELECTION METHOD FOR INFLAMMATION

(71) Applicant: Purdue Research Foundation, West Lafayette, IN (US)

(72) Inventors: Philip S. Low, West Lafayette, IN (US); Lindsay E. Kelderhouse, Island Lake, IL (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/037,793

(22) PCT Filed: Nov. 19, 2014

(86) PCT No.: PCT/US2014/066347
§ 371 (c)(1),
(2) Date: May 19, 2016

(87) PCT Pub. No.: WO2015/077303
PCT Pub. Date: May 28, 2015

(65) Prior Publication Data
US 2016/0274090 A1    Sep. 22, 2016

Related U.S. Application Data

(60) Provisional application No. 61/906,331, filed on Nov. 19, 2013.

(51) Int. Cl.
*A61K 49/00* (2006.01)
*A61K 51/04* (2006.01)
*G01N 33/50* (2006.01)

(52) U.S. Cl.
CPC ..... *G01N 33/5088* (2013.01); *A61K 49/0032* (2013.01); *A61K 49/0052* (2013.01); *A61K 51/0459* (2013.01); *G01N 2800/52* (2013.01)

(58) Field of Classification Search
CPC ........... A61K 49/00; A61K 49/0032; A61K 49/0052; A61K 51/00; A61K 51/0459; G01N 2800/52; G01N 33/5088
USPC .......... 424/1.11, 1.64, 1.69, 1.81, 1.85, 1.89, 424/9.1, 9.2, 9.3, 9.4, 9.5, 9.6
See application file for complete search history.

(56) References Cited

U.S. PATENT DOCUMENTS

| | | | |
|---|---|---|---|
| 5,688,488 A | 11/1997 | Low et al. | |
| 5,820,847 A | 10/1998 | Low et al. | |
| 6,692,724 B1 * | 2/2004 | Yang | A61K 51/0497 424/1.11 |
| 7,128,893 B2 | 10/2006 | Leamon et al. | |
| 7,601,332 B2 | 10/2009 | Vlahov et al. | |
| 7,862,798 B2 * | 1/2011 | Leamon | A61K 51/0459 424/1.11 |
| 8,105,568 B2 | 1/2012 | Vlahov et al. | |
| 8,288,557 B2 | 10/2012 | Vlahov et al. | |
| 8,313,728 B2 | 11/2012 | Leamon et al. | |
| 8,834,842 B2 | 9/2014 | Leamon et al. | |
| 8,865,126 B2 | 10/2014 | Leamon et al. | |
| 8,883,737 B2 | 11/2014 | Reddy et al. | |
| 8,987,281 B2 | 3/2015 | Reddy et al. | |
| 9,233,175 B2 * | 1/2016 | Low | A61K 49/0052 |
| 2009/0169550 A1 | 7/2009 | Dummer | |
| 2011/0286921 A1 | 11/2011 | Schibli et al. | |
| 2012/0128587 A1 | 5/2012 | Leamon et al. | |
| 2013/0071321 A1 | 3/2013 | Low et al. | |
| 2013/0158271 A1 | 6/2013 | Vlahov et al. | |
| 2014/0140925 A1 | 5/2014 | Leamon et al. | |

FOREIGN PATENT DOCUMENTS

| | | |
|---|---|---|
| WO | 2006/069388 | 6/2006 |
| WO | 2006/071754 | 7/2006 |
| WO | 2006/101845 | 9/2006 |
| WO | 2006/105141 | 10/2006 |
| WO | 2007/022493 | 2/2007 |
| WO | 2008098112 A2 | 8/2008 |
| WO | 2009/002993 | 12/2008 |

OTHER PUBLICATIONS

Fisher et al., "Exploratory study of 99m-Tc-EC20 imaging for identifying patients with folate receptor-positive solid tumors," *Journal of Nuclear Medicine*, 2008; 49:899-906.
Reddy et al., "Preclinical evaluation of EC145, a folate-vinca alkaloid conjugate," *Cancer Research*, 2007; 67:4434-4442.
Yap et al., "Beyond chemotherapy: targeted therapies in ovarian cancer," *Nature Reviews Cancer*, 2009; 9:167-181.
Downs et al., "A prospective randomized trial of thalidomide with topotecan compared with topotecan alone in women with recurrent epithelial ovarian carcinoma," *Cancer*, 2008; 112:331-339.
Sausville E. et al: "A phase I study of EC145 administered weeks 1 and 3 of a 4-week cycle in patients with refractory solid tumors". Journal of Clinical Oncology: 2007 ASCO Annual Meeting Proceedings (Post-Meeting Edition), 2007; 25(18S): 2577.
Leamon, C.P.et al. "Comparative preclinical activity of the folate-targeted Vinca alkaloid conjugates EC140 and EC145." International Journal of Cancer, 2007; 121(7):1585-1592.
Leamon, C. P. "Folate-targeted drug strategies for the treatment of cancer." Current Opinion in Investigational Drugs, 2008; 9(12):1277-1286.
Reddy, J. et al. "Anti tumor effect of EC145 in combination with DOXIL® in folate receptor positive tumor cell lines." Proceedings of the Annual Meeting of the American Association for Cancer Research, 2009; Abstract #1825, vol. 50, p. 439.

(Continued)

*Primary Examiner* — D. L. Jones
(74) *Attorney, Agent, or Firm* — Faegre Drinker Biddle & Reath LLP

(57) ABSTRACT

The invention relates to methods and compositions for the selection of patients for therapy with an anti-inflammatory drug. More particularly, the invention relates to compositions comprising folate-imaging agent conjugates for the selection of patients for therapy with an anti-inflammatory drug, and methods and uses therefor.

20 Claims, 20 Drawing Sheets

(56) References Cited

OTHER PUBLICATIONS

Endocyte: "Study of Vintafolide (EC145) in patients with progressive adenocarcinoma of the lung," Clinicaltrials.gov; XP002692174 (Aug. 2, 2007).
Endocyte: "Study of Vintafolide (EC145) in patients with advanced ovarian and endometrial cancers," Clinicaltrials.gov; XP002692175 (Jul. 24, 2007).
Endocyte: "Platinum resistant ovarian cancer evaluation of Doxil and Vintafolide (EC145) combination therapy," Clinicaltrials.gov; XP002692176 (Jul. 23, 2008).
Carney MT, Meier DE. "Palliative care and end-of-life issues." Anesthesiol Clin North America Mar. 2000;18(1):183-209.
Barnett et al., "Structure-activity relationships of dimeric Catharanthus alkaloids. 1. Deacetyl vinblastine amide (vindesine) sulfate," J. Med. Chem. 21:88-96 (1978).
Rouschias, G., "Recent advances in the chemistry of rhenium," Chem. Rev., 74: 531 (1974).
Symanouwski et al., Journal of Clinical Oncology, 2010 ASCO Annual Meeting Abstracts, vol. 28, No. 15 Suppl (May 20 Supplement), 2010, Abstract No. 5034.
Shen et al., "Use of Folate-Conjugated Imaging Agents to Target Alternatively Activated Macrophages in a Murine Model of Asthma," *Mol. Pharmaceutics*, 2013, 10 (5): 1918-1927.
Endocyte Begins Phase II Clinical Trial of Ec145 for Treatment of Women With Ovarian Cancer Medical News Today.
PCT Search Report and Written Opinion for PCT/US2014/066347, dated Feb. 23, 2015.
European Search Report issued in EP 14864223 dated May 23, 2017.
Shen et al., "Use of Folate-Conjugated Imaging Agents to Target Alternatively Activated Macrophages in a Murine Model of Asthma" Mol. Pharmaceutics 2013, 10, 1918-1927.
Office Action issued in EP 14864223 dated Apr. 10, 2018.
Kularatne, Sumith A., et al., "Comparative Analysis o fFolate Drived PET Imaging Agents with [18F]-2-Fluoro-2-deoxy-D-glucose Using a Rodent Inflammatory Paw Model", Molecular Pharmaceutics, vol. 10, No. 8, Aug. 5, 2013, pp. 3103-3111, XP055622477, US ISSN: 1543-8384, DOI: 10.1021/mp4001684.
Extended European Search Report issued by the European Patent Office, Munich, Germany, dated Oct. 2, 2019, for European Patent Application No. 19170627.4.

* cited by examiner

PATIENT SELECTION METHOD FOR INFLAMMATION

CROSS-REFERENCE TO RELATED APPLICATIONS

The present application is a national stage entry under 35 U.S.C. § 371(b) of PCT International Application No. PCT/US2014/066347, filed Nov. 19, 2014, and claims, under 35 U.S.C. § 119(e), the benefit of and priority to U.S. Provisional Application No. 61/906,331 filed Nov. 19, 2013, the disclosures of both of which is are hereby incorporated by reference herein in their entirety.

TECHNICAL FIELD

The invention relates to methods and compositions for the selection of patients for therapy with an anti-inflammatory drug. More particularly, the invention relates to compositions comprising folate-imaging agent conjugates for the selection of patients for therapy with an anti-inflammatory drug, and methods and uses therefor.

BACKGROUND AND SUMMARY

Biologic therapies (etanercept, infliximab, adalimumab, rituximab, abatacept, anakinra, efalizumab, etc.) have become the preferred method for treatment of many autoimmune and inflammatory diseases, primarily because of their increased efficacy, enhanced speed of onset, and greater tolerability. However, despite these obvious benefits, about forty percent of those receiving biologic therapies still fail to respond. Because no clinical marker currently exists to accurately predict response to therapy, physicians have been forced to rely on subjective criteria (i.e., assessment of pain, coloration and swelling, radiographic analysis, etc.) to determine whether to continue with a current treatment or not. Moreover, since meaningful changes in many subjective parameters are considered reliable only four to six months after initiation of therapy, identification of nonresponders is often possible only after irreversible damage or an ideal "window of therapeutic opportunity" has transpired. Considering the high costs of treatment (often upwards of $40,000 per year) and the damage that can ensue when an initial therapy fails, an ability to quickly predict a patient's eventual response could reduce both cost and morbidity associated with a less informed approach to anti-inflammatory drug selection.

Activated proinflammatory macrophages have been shown to constitute key players in the development and progression of a number of inflammatory and autoimmune diseases, including rheumatoid arthritis, atherosclerosis, psoriasis, ischemia/reperfusion injury, pulmonary fibrosis, organ transplant rejection, ulcerative colitis, impact trauma, multiple sclerosis, scleroderma, Crohn's disease, Sjögren's syndrome, glomerulonephritis, and sarcoidosis. Because the folate receptor β, a glycosylphosphatidylinositol anchored glycoprotein, is uniquely over-expressed on the surface of these activated macrophages, folate receptor-targeted imaging agents have been recently exploited to visualize sites of activated macrophage accumulation in both animals and humans. More specifically, $^{99m}$Tc-EC20, a folate receptor-targeted radiopharmaceutical, has proven particularly useful for these imaging applications in that uptake of $^{99m}$Tc-EC20 has been observed to correlate directly with severity of arthritis symptoms.

Applicants have surprisingly found that reduction in uptake of folate-imaging agent conjugates, such as $^{99m}$Tc-EC20, dramatically precedes observable changes in symptomology for patients with inflammatory disease being treated with anti-inflammatory drugs. This reduction in uptake occurs regardless which specific anti-inflammatory drug is being employed. This surprising observation resulted in Applicants' invention which is a method that utilizes a folate-targeted imaging agent, such as $^{99m}$Tc-EC20, to predict an eventual response to therapy for inflammatory diseases. Applicants have demonstrated that uptake of folate receptor-targeted imaging agents at sites of inflammatory disease shortly after initiation of therapy can accurately forecast a subsequent response to an anti-inflammatory drug long before clinical changes can be detected. Accordingly, Applicants have found that folate-imaging agent conjugates are useful as clinical tools for the selection of patients who will eventually benefit from treatment with a particular anti-inflammatory drug.

Several embodiments of the invention are described by the following enumerated clauses:

1. A method for selecting a patient for therapy with an anti-inflammatory drug, the method comprising the steps of administering to the patient a folate-imaging agent conjugate, and using the folate-imaging agent conjugate to predict the response of the patient to the anti-inflammatory drug.

2. Use of a folate-imaging agent conjugate for selecting a patient for therapy with an anti-inflammatory drug wherein the folate-imaging agent conjugate is administered to the patient and is used to predict the response of the patient to the anti-inflammatory drug.

3. Use of a folate-imaging agent conjugate in the manufacture of a medicament for selecting a patient for therapy with an anti-inflammatory drug wherein the folate-imaging agent conjugate is administered to the patient and is used to predict the response of the patient to the anti-inflammatory drug.

4. The method or use of any one of clauses 1 to 3 wherein the folate-imaging agent conjugate produces a detectable signal in the patient, wherein the signal is detected, and wherein the detection of the signal is used to predict the response of the patient to the anti-inflammatory drug.

5. The method or use of clause 4 wherein the signal is a radioactive signal.

6. The method or use of clause 4 wherein the signal is produced by a chromophore.

7. The method or use of clause 6 wherein the chromophore is a fluorophore.

8. The method or use of clause 7 wherein the fluorophore is selected from the group consisting of a fluorescein, a rhodamine, a phycoerythrin, a long wavelength fluorescent dye, and a cyanine.

9. The method or use of any one of clauses 4 to 8 wherein the signal is produced as a result of binding of the folate-imaging agent conjugate to activated macrophages.

10. The method or use of any one of clauses 1 to 9 wherein the administering step comprises a first administering step and a second administering step.

11. The method or use of clause 10 wherein the first and second administering steps produce a first signal and a second signal, respectively.

12. The method or use of clause 11 wherein the first signal and the second signal are quantified.

13. The method or use of clause 11 wherein the first signal is obtained by administering the folate-imaging agent conjugate prior to administration of the anti-inflammatory drug.

14. The method or use of clause 11 wherein the first signal is obtained by administering the folate-imaging agent conjugate on the same day as treatment with the anti-inflammatory drug is initiated.

15. The method or use of clause 11 wherein the second signal is obtained by administering the folate-imaging agent conjugate subsequent to the administration of the anti-inflammatory drug.

16. The method or use of clause 11 wherein the second signal is obtained by administering the folate-imaging agent conjugate within about 21 days after administration of the anti-inflammatory drug is initiated.

17. The method or use of clause 11 wherein the second signal is obtained by administering the folate-imaging agent conjugate within about 1 week, about 2 weeks, about 3 weeks, or about 4 weeks after the administration of the anti-inflammatory drug is initiated.

18. The method or use of clause 11 wherein the second signal is obtained by administering the folate-imaging agent conjugate on any one of the days within about 21 days after the administration of the anti-inflammatory drug is initiated.

19. The method or use of clause 11 wherein the second signal is obtained by administering the folate-imaging agent conjugate on any one of the days within about 12 weeks after the administration of the anti-inflammatory drug is initiated.

20. The method or use of clause 11 wherein the second signal is reduced by about 10%, about 20%, about 30%, about 40%, about 50%, about 60%, about 70%, about 80%, about 90%, or about 100% compared to the first signal, and wherein the reduction indicates that the patient should continue to be treated with the anti-inflammatory drug.

21. The method or use of clause 11 wherein the second signal is obtained by administering the folate-imaging agent conjugate about 2, about 3, about 4, about 5, about 6, about 12, about 15, or about 21 days after the administration of the anti-inflammatory drug is initiated.

22. The method or use of any one of clauses 1 to 21 wherein the inflammatory disease is selected from the group consisting of arthritis, osteoarthritis, rheumatoid arthritis, atherosclerosis, psoriasis, ischemia/reperfusion injury, pulmonary fibrosis, organ transplant rejection, ulcerative colitis, impact trauma, osteomyelitis, multiple sclerosis, scleroderma, Crohn's disease, Sjögren's syndrome, glomerulonephritis, systemic sclerosis, sarcoidosis, an inflammatory lesion, and chronic inflammation.

23. The method or use of any one of clauses 1 to 22 wherein the folate-imaging agent conjugate is in a parenteral dosage form.

24. The method or use of clause 23 wherein the dosage form is selected from the group consisting of an intradermal, a subcutaneous, an intramuscular, an intraperitoneal, an intravenous, and an intrathecal dosage form.

25. The method or use of any one of clauses 1 to 24 wherein the folate-imaging agent conjugate is in a composition and wherein the composition further comprises a pharmaceutically acceptable carrier.

26. The method or use of clause 25 wherein the pharmaceutically acceptable carrier is a liquid carrier.

27. The method or use of clause 26 wherein the liquid carrier is selected from the group consisting of saline, glucose, alcohols, glycols, esters, amides, and a combination thereof.

28. The method or use of any one of clauses 1 to 27 wherein the folate-imaging agent conjugate is administered in an effective amount.

29. The method or use of clause 28 wherein the effective amount ranges from about 1 ng to about 1 mg per kilogram of body weight of the patient.

30. The method or use of clause 28 wherein the effective amount ranges from about 100 ng to about 500 µg per kilogram of body weight of the patient.

31. The method or use of clause 28 wherein the effective amount ranges from about 100 ng to about 25 µg per kilogram of body weight of the patient.

32. The method or use of clause 28 wherein the effective amount ranges from about 1 µg/m$^2$ to about 500 mg/m$^2$ of body surface area of the patient.

33. The method or use of clause 28 wherein the effective amount ranges from about 1 µg/m$^2$ to about 300 mg/m$^2$ of body surface area of the patient.

34. The method or use of clause 28 wherein the effective amount ranges from about 10 µg/kg to about 100 µg/kg of patient body weight.

35. The method or use of any one of clauses 1 to 34 further comprising the step of administering unlabeled folic acid to the patient.

36. The method or use of clause 35 wherein the unlabeled folic acid is administered before administration of the folate-imaging agent conjugate.

37. The method or use of any one of clauses 1 to 5 or 9 to 36 wherein the folate-imaging agent conjugate has the formula wherein M is a radionuclide.

38. The method or use of any one of clauses 1 to 5 or 9 to 37 wherein the folate-imaging agent conjugate has the formula

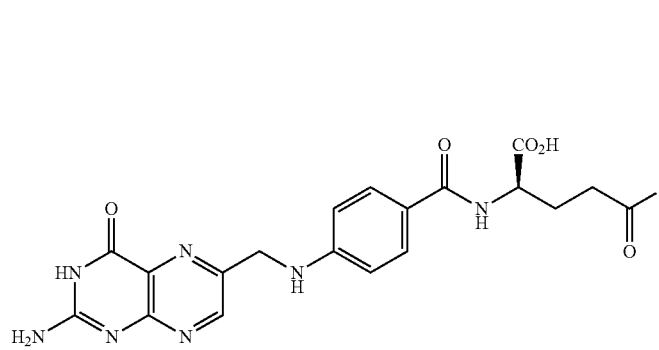
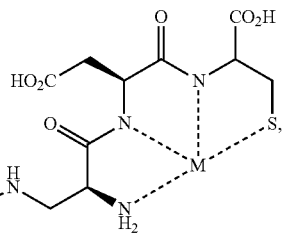

wherein M is a radionuclide.

39. The method or use of clause 37 or 38 wherein the radionuclide is selected from the group consisting of an isotope of gallium, an isotope of indium, an isotope of copper, an isotope of technetium, and an isotope of rhenium.

40. The method or use of clause 39 wherein the radionuclide is an isotope of technetium.

41. The method or use of clause 40 wherein the technecium is $^{99m}$-technetium.

42. The method or use of any one of clauses 1 to 5 or 9 to 41 wherein the folate-imaging agent conjugate is $^{99m}$Tc-EC20.

43. The method or use of any one of clauses 1 to 5 or 9 to 42 wherein the signal is detected using scintigraphic imaging.

44. The method or use of any one of clauses 1 to 43 wherein the patient is a human patient.

45. The method or use of any one of clauses 1 to 43 wherein the patient is a veterinary patient.

46. The method or use of any one of clauses 1 to 5 or 9 to 45 wherein the folate-imaging agent conjugate has a radiochemical purity of at least 90% based on weight percentage.

47. The method or use of any one of clauses 1 to 46 wherein the folate-imaging agent conjugate is in the form of a reconstituted lyophilizate.

48. The method or use of any one of clauses 1 to 47 wherein the folate-imaging agent conjugate is in a sterile, pyrogen-free aqueous solution.

49. The method or use of any one of clauses 1-5, 9 to 36, or 44 to 48 wherein the folate-imaging agent conjugate has the formula:

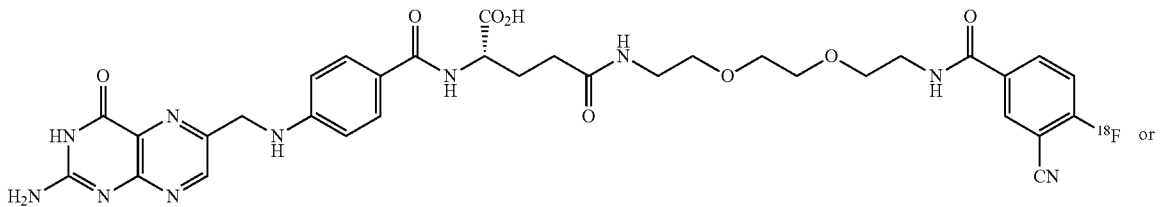

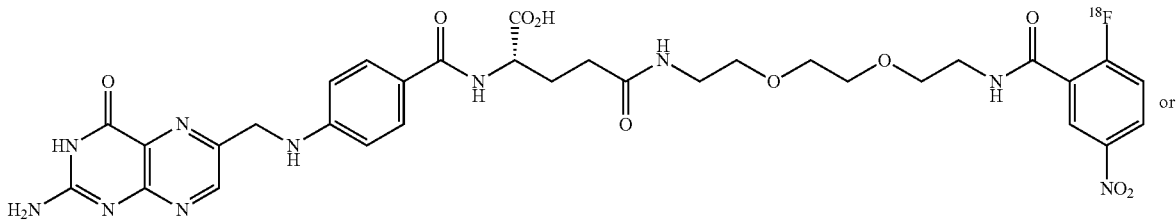

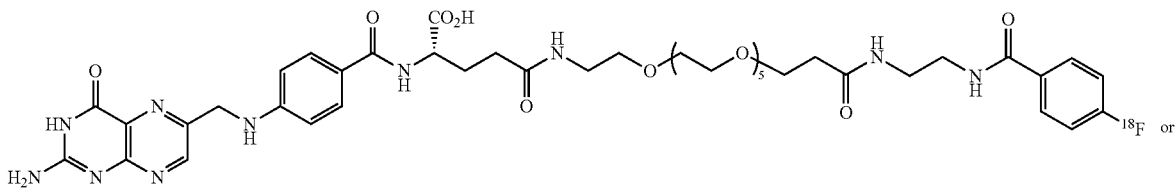

-continued

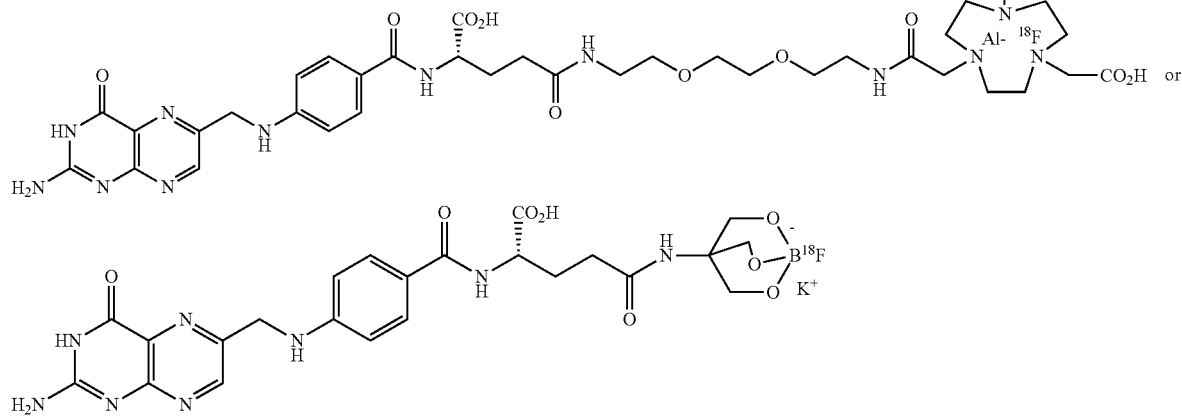

or a pharmaceutically acceptable salt of any of these compounds.

50. The method or use of any one of clauses 1-5, 9 to 36, or 44 to 48 wherein the folate-imaging agent conjugate has the formula:

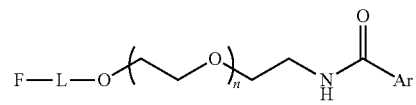

wherein F is a folate ligand, L is an optional bivalent linker; n is an integer selected from 1 to about 100, or from 1 to about 20, or n is 1, 2, 3, 4, 5, 6, 7, or 8; Ar is an aryl group, including heteroaryl groups, that includes one or more substituents $R^f$ comprising a radiophore or a precursor to a radiophore.

51. The method or use of any one of clauses 1-5, 9 to 36, or 44 to 48 wherein the folate-imaging agent conjugate has the formula:

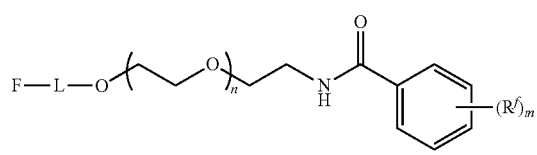

wherein F is a folate ligand; L is an optional bivalent linker; n is an integer selected from 1 to about 100, or from 1 to about 20, or n is 1, 2, 3, 4, 5, 6, 7, or 8; $R^f$ is as described below; and m is an integer selected from 1 to about 3.

52. The method or use of any one of clauses 1-5, 9 to 36, or 44 to 48 wherein the folate-imaging agent conjugate has the formula:

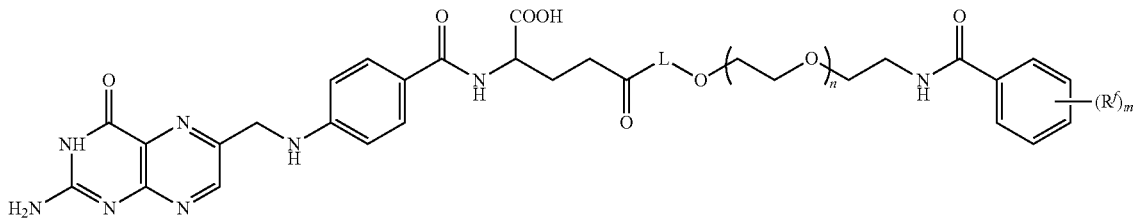

wherein L is an optional bivalent linker; n is an integer selected from 1 to about 100; $R^f$ is as defined in the various embodiments herein; and m is an integer selected from 1 to about 3.

53. A method for selecting a patient for therapy with an anti-inflammatory drug, the method comprising the steps of assessing whether the patient is in need of therapy with the anti-inflammatory drug by relying on the results obtained by means for detecting a signal produced in the patient by a folate-imaging agent conjugate administered to the patient; and prescribing or continuing to prescribe the anti-inflammatory drug to treat the patient assessed to be in need of the anti-inflammatory drug.

54. The method of clause 54 wherein the folate-imaging agent conjugate produces a detectable signal in the patient, wherein the signal is detected, and wherein the detection of the signal is used to assess whether the patient is in need of therapy with the anti-inflammatory drug.

55. The method of clause 54 wherein the signal is a radioactive signal.

56. The method of clause 54 wherein the signal is produced by a chromophore.

57. The method of clause 56 wherein the chromophore is a fluorophore.

58. The method of clause 57 wherein the fluorophore is selected from the group consisting of a fluorescein, a rhodamine, a phycoerythrin, a long wavelength fluorescent dye, and a cyanine.

59. The method of any one of clauses 53 to 58 wherein the signal is produced as a result of binding of the folate-imaging agent conjugate to activated macrophages.

60. The method of any one of clauses 53 to 59 wherein the administration comprises a first administering step and a second administering step.

61. The method of clause 60 wherein the first and second administering steps produce a first signal and a second signal, respectively.

62. The method of clause 61 wherein the first signal and the second signal are quantified.

63. The method of clause 61 wherein the first signal is obtained by administering the folate-imaging agent conjugate prior to administration of the anti-inflammatory drug.

64. The method of clause 61 wherein the first signal is obtained by administering the folate-imaging agent conjugate on the same day as treatment with the anti-inflammatory drug is initiated.

65. The method of clause 61 wherein the second signal is obtained by administering the folate-imaging agent conjugate subsequent to the administration of the anti-inflammatory drug.

66. The method of clause 61 wherein the second signal is obtained by administering the folate-imaging agent conjugate within about 21 days after administration of the anti-inflammatory drug is initiated.

67. The method of clause 61 wherein the second signal is obtained by administering the folate-imaging agent conjugate within about 1 week, about 2 weeks, about 3 weeks, or about 4 weeks after the administration of the anti-inflammatory drug is initiated.

68. The method of clause 61 wherein the second signal is obtained by administering the folate-imaging agent conjugate on any one of the days within about 21 days after the administration of the anti-inflammatory drug is initiated.

69. The method of clause 61 wherein the second signal is obtained by administering the folate-imaging agent conjugate on any one of the days within about 12 weeks after the administration of the anti-inflammatory drug is initiated.

70. The method of clause 61 wherein the second signal is reduced by about 10%, about 20%, about 30%, about 40%, about 50%, about 60%, about 70%, about 80%, about 90%, or about 100% compared to the first signal, and wherein the reduction indicates that the patient should continue to be treated with the anti-inflammatory drug.

71. The method of clause 61 wherein the second signal is obtained by administering the folate-imaging agent conjugate about 2, about 3, about 4, about 5, about 6, about 12, about 15, or about 21 days after the administration of the anti-inflammatory drug is initiated.

72. The method of any one of clauses 53 to 71 wherein the inflammatory disease is selected from the group consisting of arthritis, osteoarthritis, rheumatoid arthritis, atherosclerosis, psoriasis, ischemia/reperfusion injury, pulmonary fibrosis, organ transplant rejection, ulcerative colitis, impact trauma, osteomyelitis, multiple sclerosis, scleroderma, Crohn's disease, Sjögren's syndrome, glomerulonephritis, systemic sclerosis, sarcoidosis, an inflammatory lesion, and chronic inflammation.

73. The method of any one of clauses 53 to 72 wherein the folate-imaging agent conjugate is in a parenteral dosage form.

74. The method of clause 73 wherein the dosage form is selected from the group consisting of an intradermal, a subcutaneous, an intramuscular, an intraperitoneal, an intravenous, and an intrathecal dosage form.

75. The method of any one of clauses 53 to 74 wherein the folate-imaging agent conjugate is in a composition and wherein the composition further comprises a pharmaceutically acceptable carrier.

76. The method of clause 75 wherein the pharmaceutically acceptable carrier is a liquid carrier.

77. The method of clause 76 wherein the liquid carrier is selected from the group consisting of saline, glucose, alcohols, glycols, esters, amides, and a combination thereof.

78. The method of any one of clauses 53 to 77 wherein the folate-imaging agent conjugate is administered in an effective amount.

79. The method of clause 78 wherein the effective amount ranges from about 1 ng to about 1 mg per kilogram of body weight of the patient.

80. The method of clause 78 wherein the effective amount ranges from about 100 ng to about 500 µg per kilogram of body weight of the patient.

81. The method of clause 78 wherein the effective amount ranges from about 100 ng to about 25 µg per kilogram of body weight of the patient.

82. The method of clause 78 wherein the effective amount ranges from about 1 µg/m$^2$ to about 500 mg/m$^2$ of body surface area of the patient.

83. The method of clause 78 wherein the effective amount ranges from about 1 µg/m$^2$ to about 300 mg/m$^2$ of body surface area of the patient.

84. The method of clause 78 wherein the effective amount ranges from about 10 µg/kg to about 100 µg/kg of patient body weight.

85. The method of any one of clauses 53 to 84 further comprising the step of administering unlabeled folic acid to the patient.

86. The method of clause 85 wherein the unlabeled folic acid is administered before administration of the folate-imaging agent conjugate.

87. The method of any one of clauses 53 to 55 or 59 to 86 wherein the folate-imaging agent conjugate has the formula

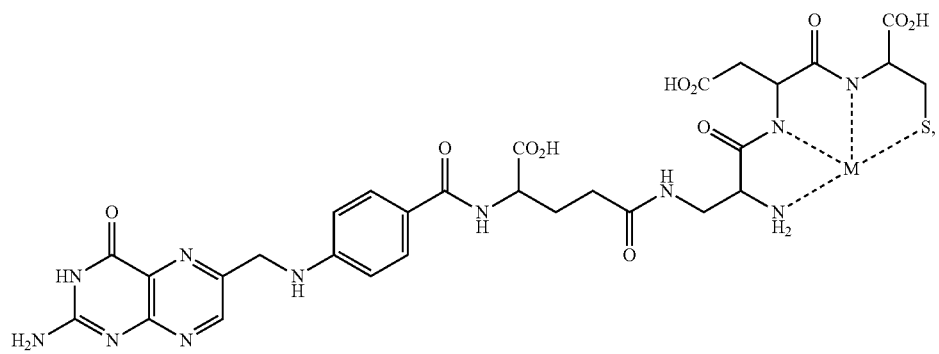

wherein M is a radionuclide.

88. The method of any one of clauses 53 to 55 or 59 to 87 wherein the folate-imaging agent conjugate has the formula:

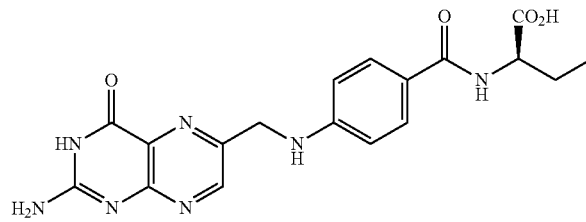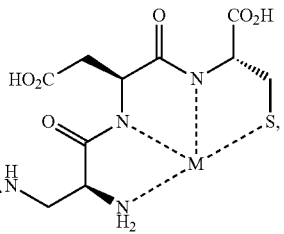

wherein M is a radionuclide.

89. The method of clause 87 or 88 wherein the radionuclide is selected from the group consisting of an isotope of gallium, an isotope of indium, an isotope of copper, an isotope of technetium, and an isotope of rhenium.

90. The method of clause 89 wherein the radionuclide is an isotope of technetium.

91. The method of clause 90 wherein the technecium is $^{99m}$-technetium.

92. The method of any one of clauses 53 to 55 or 59 to 91 wherein the folate-imaging imaging agent conjugate $^{99m}$Tc-EC20.

93. The method of any one of clauses 53 to 55 or 59 to 92 wherein the signal is detected using scintigraphic imaging.

94. The method of any one of clauses 53 to 93 wherein the patient is a human patient.

95. The method of any one of clauses 53 to 93 wherein the patient is a veterinary patient.

96. The method of any one of clauses 53 to 55 or 59 to 95 wherein the folate-imaging agent conjugate has a radiochemical purity of at least 90% based on weight percentage.

97. The method of any one of clauses 53 to 96 wherein the folate-imaging agent conjugate is in the form of a reconstituted lyophilizate.

98. The method of any one of clauses 53 to 97 wherein the folate-imaging agent conjugate is in a sterile, pyrogen-free aqueous solution.

99. The method of any one of clauses 53-55, 59 to 86, or 94 to 98 wherein the folate-imaging agent conjugate has the formula:

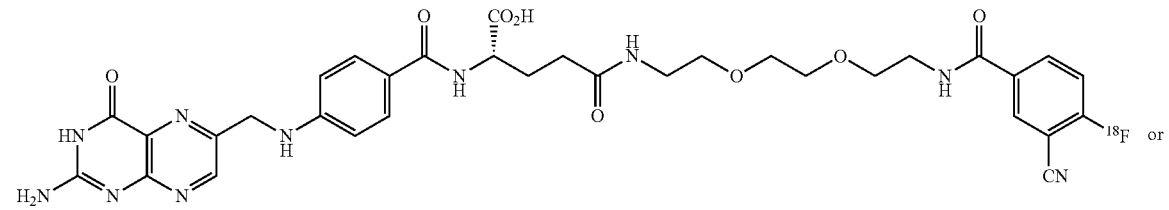

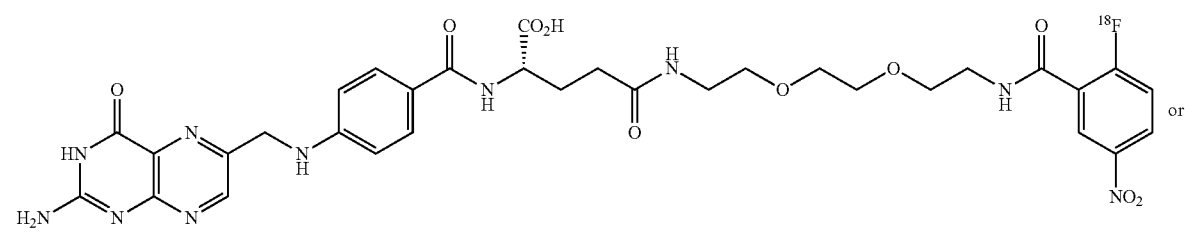

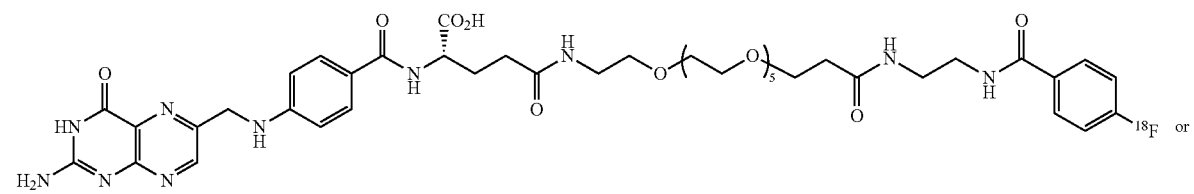

-continued

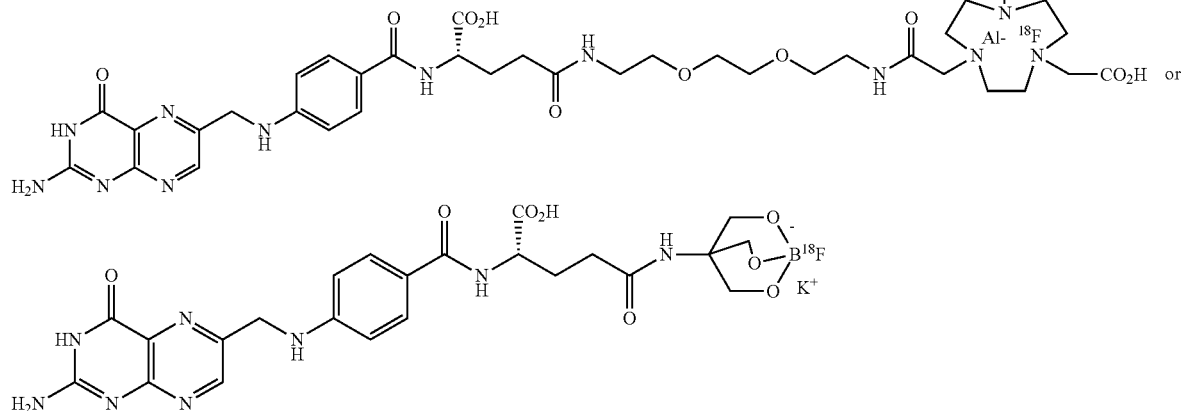

or

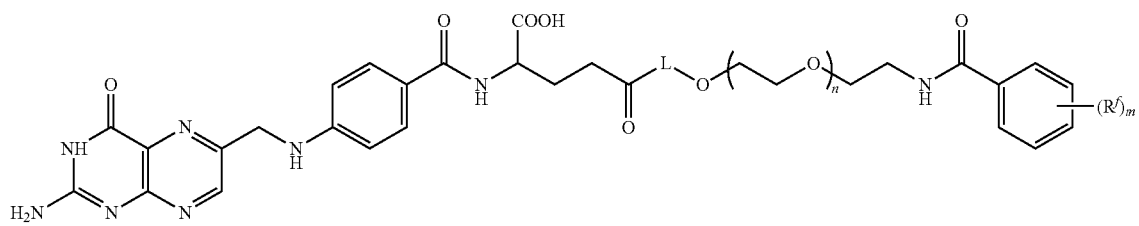

or a pharmaceutically acceptable salt of any of these compounds.

100. The method of any one of clauses 53-55, 59 to 86, or 94 to 98 wherein the folate-imaging agent conjugate has the formula:

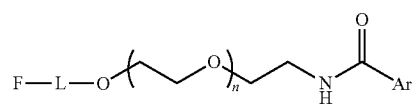

wherein F is a folate ligand, L is an optional bivalent linker; n is an integer selected from 1 to about 100, or from 1 to about 20, or n is 1, 2, 3, 4, 5, 6, 7, or 8; Ar is an aryl group, including heteroaryl groups, that includes one or more substituents $R^f$ comprising a radiophore or a precursor to a radiophore.

101. The method of any one of clauses 53-55, 59 to 86, or 94 to 98 wherein the folate-imaging agent conjugate has the formula:

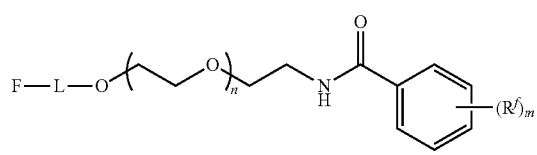

wherein F is a folate ligand; L is an optional bivalent linker; n is an integer selected from 1 to about 100, or from 1 to about 20, or n is 1, 2, 3, 4, 5, 6, 7, or 8; $R^f$ is as described below; and m is an integer selected from 1 to about 3.

102. The method of any one of clauses 53-55, 59 to 86, or 94 to 98 wherein the folate-imaging agent conjugate has the formula:

wherein L is an optional bivalent linker; n is an integer selected from 1 to about 100; $R^f$ is as defined in the various embodiments herein; and m is an integer selected from 1 to about 3.

103. A method for predicting the efficacy of an anti-inflammatory drug in a patient, the method comprising the steps of administering to the patient a folate-imaging agent conjugate, and using the folate-imaging agent conjugate to predict efficacy of the anti-inflammatory drug in the patient.

104. The method of clause 103 wherein the folate-imaging agent conjugate produces a detectable signal in the patient, wherein the signal is detected, and wherein the detection of the signal is used to assess whether the patient is in need of therapy with the anti-inflammatory drug.

105. The method of clause 104 wherein the signal is a radioactive signal.

106. The method of clause 104 wherein the signal is produced by a chromophore.

107. The method of clause 106 wherein the chromophore is a fluorophore.

108. The method of clause 107 wherein the fluorophore is selected from the group consisting of a fluorescein, a rhodamine, a phycoerythrin, a long wavelength fluorescent dye, and a cyanine.

109. The method of any one of clauses 104 to 108 wherein the signal is produced as a result of binding of the folate-imaging agent conjugate to activated macrophages.

110. The method of any one of clauses 103 to 109 wherein the administering step comprises a first administering step and a second administering step.

111. The method of clause 110 wherein the first and second administering steps produce a first signal and a second signal, respectively.

112. The method of clause 111 wherein the first signal and the second signal are quantified.

113. The method of clause 111 wherein the first signal is obtained by administering the folate-imaging agent conjugate prior to administration of the anti-inflammatory drug.

114. The method of clause 111 wherein the first signal is obtained by administering the folate-imaging agent conjugate on the same day as treatment with the anti-inflammatory drug is initiated.

115. The method of clause 111 wherein the second signal is obtained by administering the folate-imaging agent conjugate subsequent to the administration of the anti-inflammatory drug.

116. The method of clause 111 wherein the second signal is obtained by administering the folate-imaging agent conjugate within about 21 days after administration of the anti-inflammatory drug is initiated.

117. The method of clause 111 wherein the second signal is obtained by administering the folate-imaging agent conjugate within about 1 week, about 2 weeks, about 3 weeks, or about 4 weeks after the administration of the anti-inflammatory drug is initiated.

118. The method of clause 111 wherein the second signal is obtained by administering the folate-imaging agent conjugate on any one of the days within about 21 days after the administration of the anti-inflammatory drug is initiated.

119. The method of clause 111 wherein the second signal is obtained by administering the folate-imaging agent conjugate on any one of the days within about 12 weeks after the administration of the anti-inflammatory drug is initiated.

120. The method of clause 111 wherein the second signal is reduced by about 10%, about 20%, about 30%, about 40%, about 50%, about 60%, about 70%, about 80%, about 90%, or about 100% compared to the first signal, and wherein the reduction indicates that the patient should continue to be treated with the anti-inflammatory drug.

121. The method of clause 111 wherein the second signal is obtained by administering the folate-imaging agent conjugate about 2, about 3, about 4, about 5, about 6, about 12, about 15, or about 21 days after the administration of the anti-inflammatory drug is initiated.

122. The method of any one of clauses 103 to 121 wherein the inflammatory disease is selected from the group consisting of arthritis, osteoarthritis, rheumatoid arthritis, atherosclerosis, psoriasis, ischemia/reperfusion injury, pulmonary fibrosis, organ transplant rejection, ulcerative colitis, impact trauma, osteomyelitis, multiple sclerosis, scleroderma, Crohn's disease, Sjögren's syndrome, glomerulonephritis, systemic sclerosis, sarcoidosis, an inflammatory lesion, and chronic inflammation.

123. The method of any one of clauses 103 to 122 wherein the folate-imaging agent conjugate is in a parenteral dosage form.

124. The method of clause 123 wherein the dosage form is selected from the group consisting of an intradermal, a subcutaneous, an intramuscular, an intraperitoneal, an intravenous, and an intrathecal dosage form.

125. The method of any one of clauses 103 to 124 wherein the folate-imaging agent conjugate is in a composition and wherein the composition further comprises a pharmaceutically acceptable carrier.

126. The method of clause 125 wherein the pharmaceutically acceptable carrier is a liquid carrier.

127. The method of clause 126 wherein the liquid carrier is selected from the group consisting of saline, glucose, alcohols, glycols, esters, amides, and a combination thereof.

128. The method of any one of clauses 103 to 127 wherein the folate-imaging agent conjugate is administered in an effective amount.

129. The method of clause 128 wherein the effective amount ranges from about 1 ng to about 1 mg per kilogram of body weight of the patient.

130. The method of clause 128 wherein the effective amount ranges from about 100 ng to about 500 µg per kilogram of body weight of the patient.

131. The method of clause 128 wherein the effective amount ranges from about 100 ng to about 25 µg per kilogram of body weight of the patient.

132. The method of clause 128 wherein the effective amount ranges from about 1 µg/m$^2$ to about 500 mg/m$^2$ of body surface area of the patient.

133. The method of clause 128 wherein the effective amount ranges from about 1 µg/m$^2$ to about 300 mg/m$^2$ of body surface area of the patient.

134. The method of clause 128 wherein the effective amount ranges from about 10 µg/kg to about 100 µg/kg of patient body weight.

135. The method of any one of clauses 103 to 134 further comprising the step of administering unlabeled folic acid to the patient.

136. The method of clause 135 wherein the unlabeled folic acid is administered before administration of the folate-imaging agent conjugate.

137. The method of any one of clauses 103 to 105 or 109 to 136 wherein the folate-imaging agent conjugate has the formula

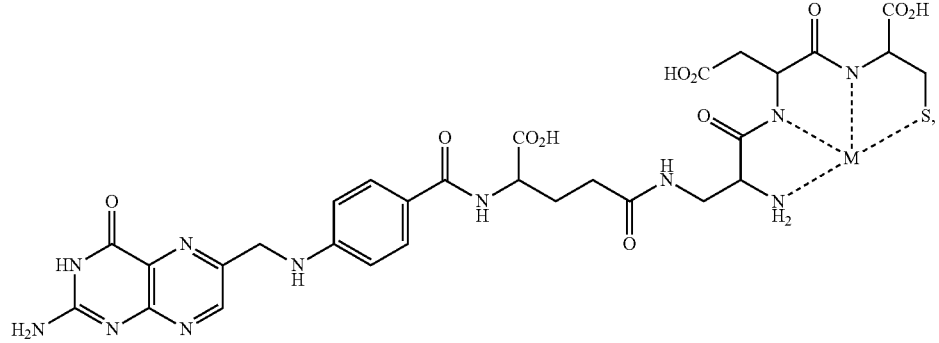

wherein M is a radionuclide.

138. The method of any one of clauses 103 to 105 or 109 to 137 wherein the folate-imaging agent conjugate has the formula

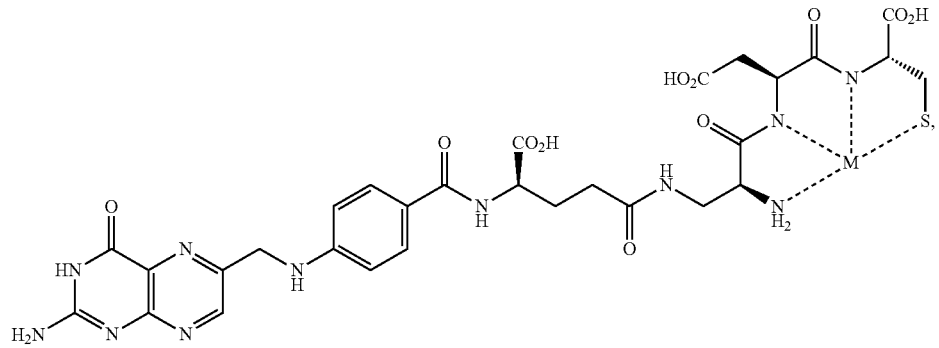

wherein M is a radionuclide.

139. The method of clause 137 or 138 wherein the radionuclide is selected from the group consisting of an isotope of gallium, an isotope of indium, an isotope of copper, an isotope of technetium, and an isotope of rhenium.

140. The method of clause 139 wherein the radionuclide is an isotope of technetium.

141. The method of clause 140 wherein the technecium is $^{99m}$-technetium.

142. The method of any one of clauses 103 to 105 or 109 to 141 wherein the folate-imaging agent conjugate is $^{99m}$Tc-EC20.

143. The method of any one of clauses 103 to 105 or 109 to 142 wherein the signal is detected using scintigraphic imaging.

144. The method of any one of clauses 103 to 143 wherein the patient is a human patient.

145. The method of any one of clauses 103 to 143 wherein the patient is a veterinary patient.

146. The method of any one of clauses 103 to 105 or 109 to 145 wherein the folate-imaging agent conjugate has a radiochemical purity of at least 90% based on weight percentage.

147. The method of any one of clauses 103 to 146 wherein the folate-imaging agent conjugate is in the form of a reconstituted lyophilizate.

148. The method of any one of clauses 103 to 147 wherein the folate-imaging agent conjugate is in a sterile, pyrogen-free aqueous solution.

149. The method of any one of clauses 103-105, 109 to 136, or 144 to 148 wherein the folate-imaging agent conjugate has the formula:

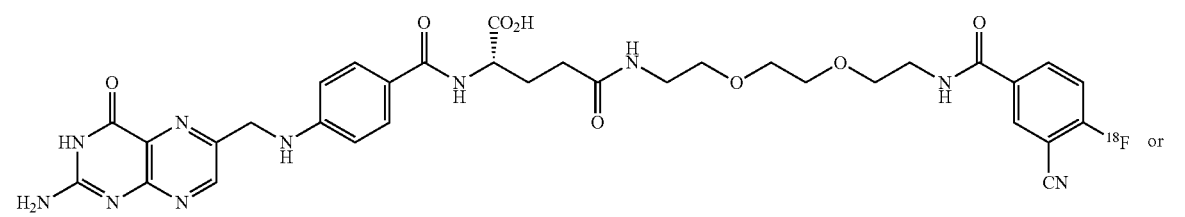

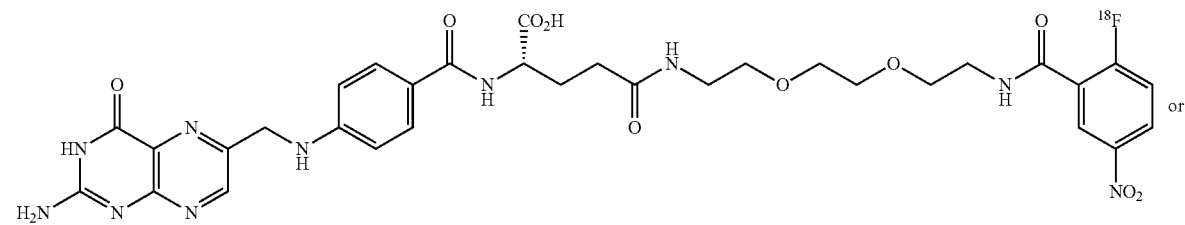

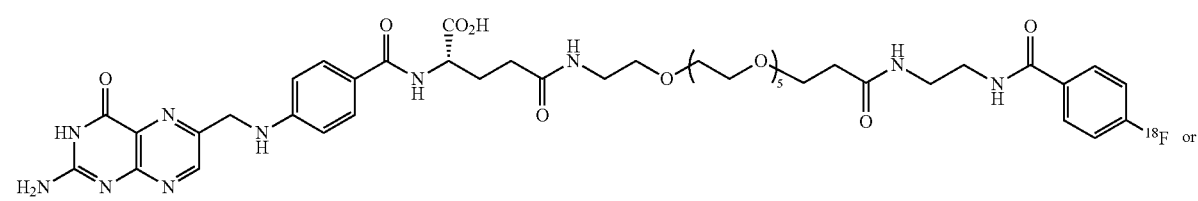

-continued

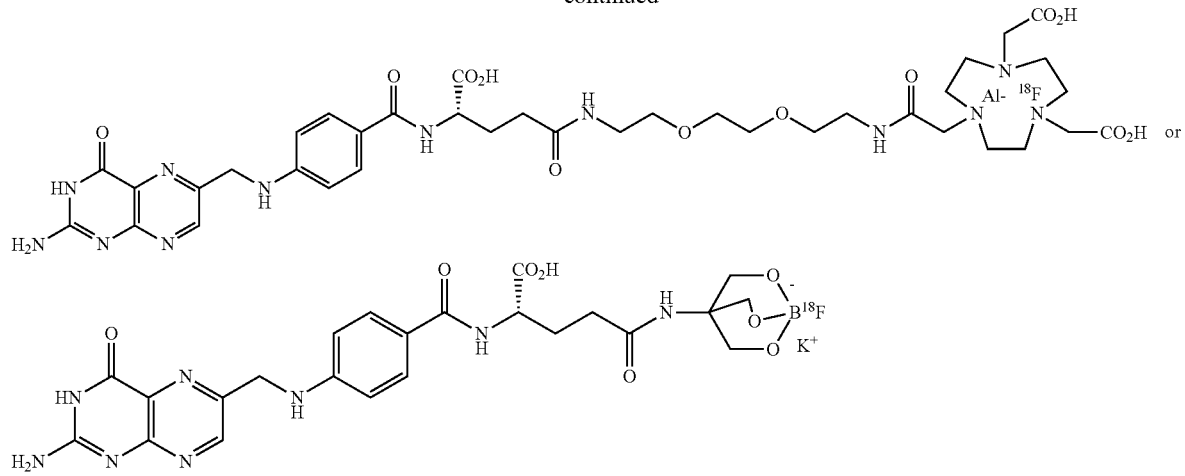

or a pharmaceutically acceptable salt of any of these compounds.

150. The method of any one of clauses 103-105, 109 to 136, or 144 to 148 wherein the folate-imaging agent conjugate has the formula:

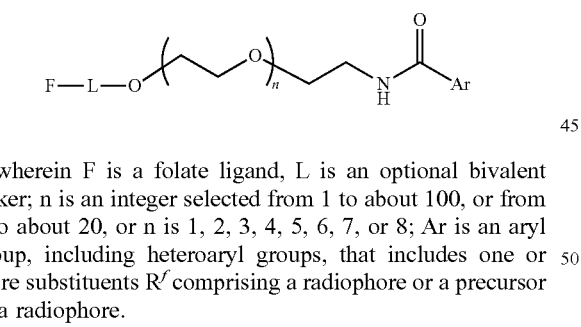

wherein F is a folate ligand, L is an optional bivalent linker; n is an integer selected from 1 to about 100, or from 1 to about 20, or n is 1, 2, 3, 4, 5, 6, 7, or 8; Ar is an aryl group, including heteroaryl groups, that includes one or more substituents $R^f$ comprising a radiophore or a precursor to a radiophore.

151. The method of any one of clauses 103-105, 109 to 136, or 144 to 148 wherein the folate-imaging agent conjugate has the formula:

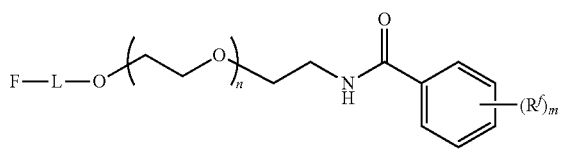

wherein F is a folate ligand; L is an optional bivalent linker; n is an integer selected from 1 to about 100, or from 1 to about 20, or n is 1, 2, 3, 4, 5, 6, 7, or 8; $R^f$ is as described below; and m is an integer selected from 1 to about 3.

152. The method of any one of clauses 103-105, 109 to 136, or 144 to 148 wherein the folate-imaging agent conjugate has the formula:

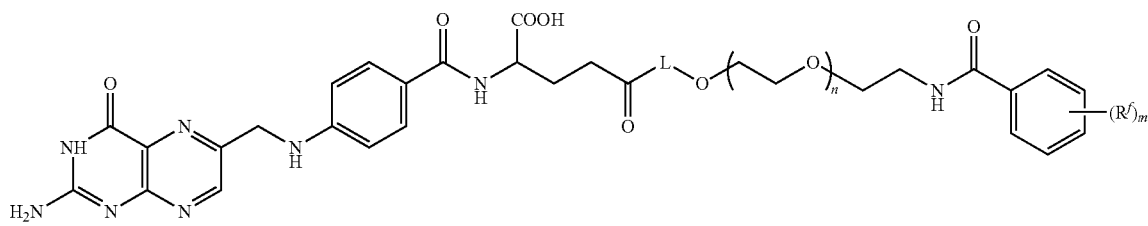

wherein L is an optional bivalent linker; n is an integer selected from 1 to about 100; $R^f$ is as defined in the various embodiments herein; and m is an integer selected from 1 to about 3.

153. The method of use of any one of clauses 1 to 152 wherein the folate portion of the folate-imaging agent conjugate comprises a compound of the formula:

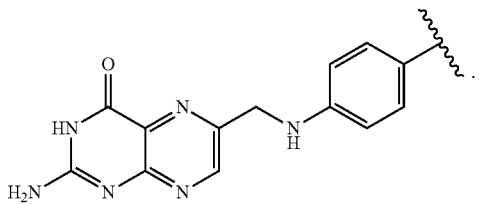 [SMILES: *c1ccc(NCc2cnc3nc(N)[nH]c(=O)c3n2)cc1]

154. The method or use of any one of clauses 1-4, 9-36, 44-45, 47-48, 53-54, 59-86, 94-95, 97-98, 103-104, 109-136, or 144-148 wherein the folate-imaging agent conjugate has the formula:

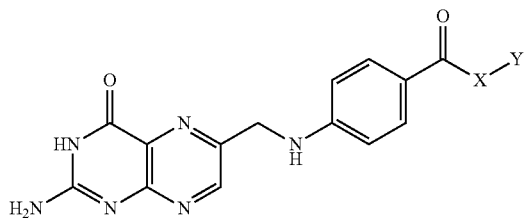

wherein:

X is an amino acid or a derivative thereof, and

Y is a dye that has a fluorescence excitation and emission spectra in the near infrared range, and said compound maintains or enhances the fluorescence of Y.

155. The method or use of any one of clauses 1-4, 9-36, 44-45, 47-48, 53-54, 59-86, 94-95, 97-98, 103-104, 109-136, or 144-148 wherein the imaging agent Y has the formula:

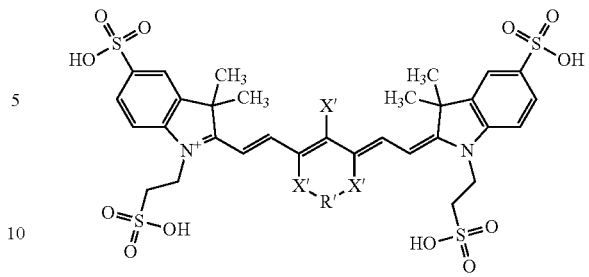

wherein:

X' is independently selected from the group consisting of O, S, N and C, and

R' is independently selected from the group consisting of CH2 and CH2CH2. In some embodiments, the dye Y is selected from the group consisting of LS288, IR800, SP054, S0121, KODAK IRD28, S2076, S0456 and derivatives thereof.

156. The method or use of any one of clauses of clauses 1-4, 9-36, 44-45, 47-48, 53-54, 59-86, 94-95, 97-98, 103-104, 109-136, or 144-148 wherein the folate-imaging agent conjugate has the formula:

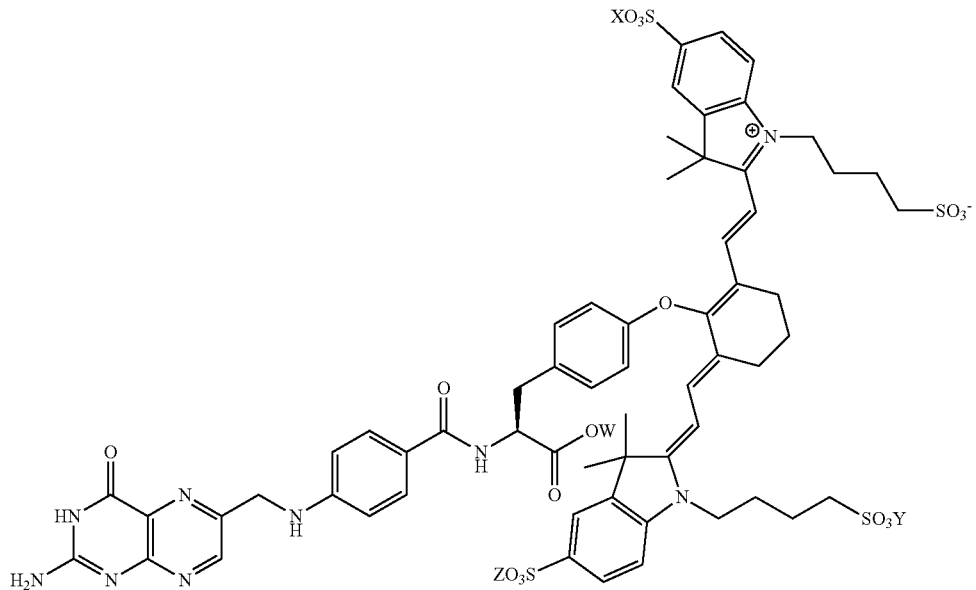

wherein W, X, Y, Z each are H, $Na^+$, $K^+$ or $NH_4^+$.

BRIEF DESCRIPTION OF THE DRAWINGS

The patent or application file contains at least one drawing executed in color. Copies of this patent or patent application publication with color drawings will be provided by the Office upon request and payment of the necessary fee.

DEFINITIONS

Figure 1A:
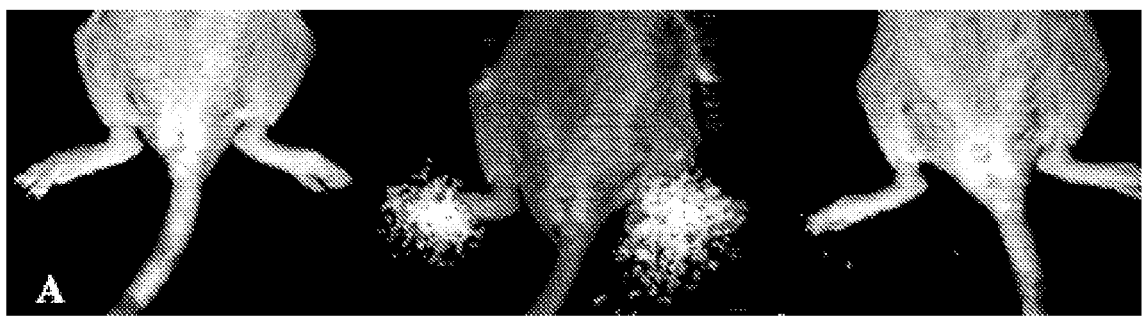
FIG. 1. Analysis of $^{99m}$Tc-EC20 accumulation in CIA mice treated with methotrexate or dexamethasone. A: Radio-image of mice injected with $^{99m}$Tc-EC20 three days after initiation of treatment with methotrexate (left), saline (middle) or dexamethasone (right). B and C: Arthritis scores and paw thickness measurements of mice in each of the following treatment groups: disease control (up triangle), methotrexate (diamond), dexamethasone (down triangle), and healthy control (square).

As used herein, the term "signal" means any detectable signal produced by a medical imaging agent that is capable of being detected using a medical imaging procedure. Examples of medical imaging procedures include, but are not limited to, the use of radioactive imaging agents in imaging procedures, the use of fluorescent imaging agents or other types of dyes in medical imaging, positron emission tomography, magnetic resonance imaging, computed tomography, scintigraphic imaging, optical imaging, ultrasound, and the like.

As used herein, the phrases "selecting a patient for therapy with an anti-inflammatory drug," "selection of a patient for therapy with an anti-inflammatory drug," "selection of patients for therapy with an anti-inflammatory drug," and similar phrases mean that the determination is made that a patient should be treated with or should continue to be treated with a particular anti-inflammatory drug.

As used herein, the phrase "predict the response of the patient to the anti-inflammatory drug," means that a determination is made whether the patient is expected to benefit from initiation of treatment or continuation of treatment with an anti-inflammatory drug or is not expected to benefit from initiation of treatment or continuation of treatment with an anti-inflammatory drug.

As used herein, the term "folate-imaging agent conjugate" means a folate ligand linked to an imaging agent.

DETAILED DESCRIPTION OF ILLUSTRATIVE EMBODIMENTS

Several embodiments of the invention are described by the following enumerated clauses and each of the embodiments described in this Detailed Description section of this application apply to each of the following embodiments:

1. A method for selecting a patient for therapy with an anti-inflammatory drug, the method comprising the steps of administering to the patient a folate-imaging agent conjugate, and using the folate-imaging agent conjugate to predict the response of the patient to the anti-inflammatory drug.

2. Use of a folate-imaging agent conjugate for selecting a patient for therapy with an anti-inflammatory drug wherein the folate-imaging agent conjugate is administered to the patient and is used to predict the response of the patient to the anti-inflammatory drug.

3. Use of a folate-imaging agent conjugate in the manufacture of a medicament for selecting a patient for therapy with an anti-inflammatory drug wherein the folate-imaging agent conjugate is administered to the patient and is used to predict the response of the patient to the anti-inflammatory drug.

4. The method or use of any one of clauses 1 to 3 wherein the folate-imaging agent conjugate produces a detectable signal in the patient, wherein the signal is detected, and wherein the detection of the signal is used to predict the response of the patient to the anti-inflammatory drug.

5. The method or use of clause 4 wherein the signal is a radioactive signal.

6. The method or use of clause 4 wherein the signal is produced by a chromophore.

7. The method or use of clause 6 wherein the chromophore is a fluorophore.

8. The method or use of clause 7 wherein the fluorophore is selected from the group consisting of a fluorescein, a rhodamine, a phycoerythrin, a long wavelength fluorescent dye, and a cyanine.

9. The method or use of any one of clauses 4 to 8 wherein the signal is produced as a result of binding of the folate-imaging agent conjugate to activated macrophages.

10. The method or use of any one of clauses 1 to 9 wherein the administering step comprises a first administering step and a second administering step.

11. The method or use of clause 10 wherein the first and second administering steps produce a first signal and a second signal, respectively.

12. The method or use of clause 11 wherein the first signal and the second signal are quantified.

13. The method or use of clause 11 wherein the first signal is obtained by administering the folate-imaging agent conjugate prior to administration of the anti-inflammatory drug.

14. The method or use of clause 11 wherein the first signal is obtained by administering the folate-imaging agent conjugate on the same day as treatment with the anti-inflammatory drug is initiated.

15. The method or use of clause 11 wherein the second signal is obtained by administering the folate-imaging agent conjugate subsequent to the administration of the anti-inflammatory drug.

16. The method or use of clause 11 wherein the second signal is obtained by administering the folate-imaging agent conjugate within about 21 days after administration of the anti-inflammatory drug is initiated.

17. The method or use of clause 11 wherein the second signal is obtained by administering the folate-imaging agent conjugate within about 1 week, about 2 weeks, about 3 weeks, or about 4 weeks after the administration of the anti-inflammatory drug is initiated.

18. The method or use of clause 11 wherein the second signal is obtained by administering the folate-imaging agent conjugate on any one of the days within about 21 days after the administration of the anti-inflammatory drug is initiated.

19. The method or use of clause 11 wherein the second signal is obtained by administering the folate-imaging agent conjugate on any one of the days within about 12 weeks after the administration of the anti-inflammatory drug is initiated.

20. The method or use of clause 11 wherein the second signal is reduced by about 10%, about 20%, about 30%, about 40%, about 50%, about 60%, about 70%, about 80%, about 90%, or about 100% compared to the first signal, and wherein the reduction indicates that the patient should continue to be treated with the anti-inflammatory drug.

21. The method or use of clause 11 wherein the second signal is obtained by administering the folate-imaging agent conjugate about 2, about 3, about 4, about 5, about 6, about 12, about 15, or about 21 days after the administration of the anti-inflammatory drug is initiated.

22. The method or use of any one of clauses 1 to 21 wherein the inflammatory disease is selected from the group consisting of arthritis, osteoarthritis, rheumatoid arthritis, atherosclerosis, psoriasis, ischemia/reperfusion injury, pulmonary fibrosis, organ transplant rejection, ulcerative colitis, impact trauma, osteomyelitis, multiple sclerosis, scleroderma, Crohn's disease, Sjögren's syndrome, glomerulonephritis, systemic sclerosis, sarcoidosis, an inflammatory lesion, and chronic inflammation.

23. The method or use of any one of clauses 1 to 22 wherein the folate-imaging agent conjugate is in a parenteral dosage form.

24. The method or use of clause 23 wherein the dosage form is selected from the group consisting of an intradermal, a subcutaneous, an intramuscular, an intraperitoneal, an intravenous, and an intrathecal dosage form.

25. The method or use of any one of clauses 1 to 24 wherein the folate-imaging agent conjugate is in a composition and wherein the composition further comprises a pharmaceutically acceptable carrier.

26. The method or use of clause 25 wherein the pharmaceutically acceptable carrier is a liquid carrier.

27. The method or use of clause 26 wherein the liquid carrier is selected from the group consisting of saline, glucose, alcohols, glycols, esters, amides, and a combination thereof.

28. The method or use of any one of clauses 1 to 27 wherein the folate-imaging agent conjugate is administered in an effective amount.

29. The method or use of clause 28 wherein the effective amount ranges from about 1 ng to about 1 mg per kilogram of body weight of the patient.

30. The method or use of clause 28 wherein the effective amount ranges from about 100 ng to about 500 µg per kilogram of body weight of the patient.

31. The method or use of clause 28 wherein the effective amount ranges from about 100 ng to about 25 µg per kilogram of body weight of the patient.

32. The method or use of clause 28 wherein the effective amount ranges from about 1 µg/m$^2$ to about 500 mg/m$^2$ of body surface area of the patient.

33. The method or use of clause 28 wherein the effective amount ranges from about 1 µg/m$^2$ to about 300 mg/m$^2$ of body surface area of the patient.

34. The method or use of clause 28 wherein the effective amount ranges from about 10 µg/kg to about 100 µg/kg of patient body weight.

35. The method or use of any one of clauses 1 to 34 further comprising the step of administering unlabeled folic acid to the patient.

36. The method or use of clause 35 wherein the unlabeled folic acid is administered before administration of the folate-imaging agent conjugate.

37. The method or use of any one of clauses 1 to 5 or 9 to 36 wherein the folate-imaging agent conjugate has the formula

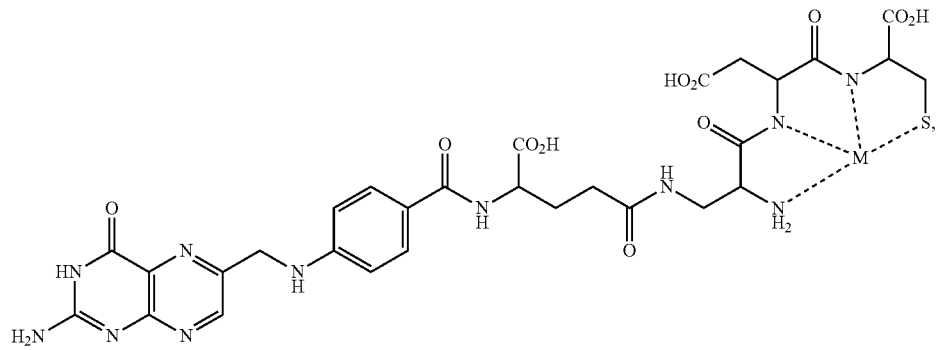

wherein M is a radionuclide.

38. The method or use of any one of clauses 1 to 5 or 9 to 37 wherein the folate-imaging agent conjugate has the formula

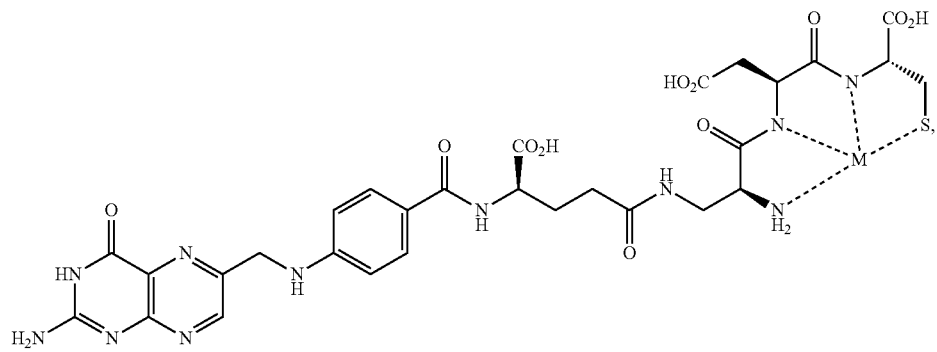

wherein M is a radionuclide.

39. The method or use of clause 37 or 38 wherein the radionuclide is selected from the group consisting of an isotope of gallium, an isotope of indium, an isotope of copper, an isotope of technetium, and an isotope of rhenium.

40. The method or use of clause 39 wherein the radionuclide is an isotope of technetium.

41. The method or use of clause 40 wherein the technecium is $^{99m}$-technetium.

42. The method or use of any one of clauses 1 to 5 or 9 to 41 wherein the folate-imaging agent conjugate is $^{99m}$Tc-EC20.

43. The method or use of any one of clauses 1 to 5 or 9 to 42 wherein the signal is detected using scintigraphic imaging.

44. The method or use of any one of clauses 1 to 43 wherein the patient is a human patient.

45. The method or use of any one of clauses 1 to 43 wherein the patient is a veterinary patient.

46. The method or use of any one of clauses 1 to 5 or 9 to 45 wherein the folate-imaging agent conjugate has a radiochemical purity of at least 90% based on weight percentage.

47. The method or use of any one of clauses 1 to 46 wherein the folate-imaging agent conjugate is in the form of a reconstituted lyophilizate.

48. The method or use of any one of clauses 1 to 47 wherein the folate-imaging agent conjugate is in a sterile, pyrogen-free aqueous solution.

49. The method or use of any one of clauses 1-5, 9 to 36, or 44 to 48 wherein the folate-imaging agent conjugate has the formula:

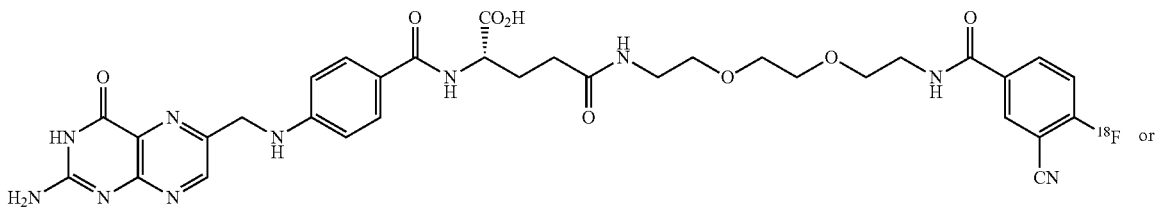

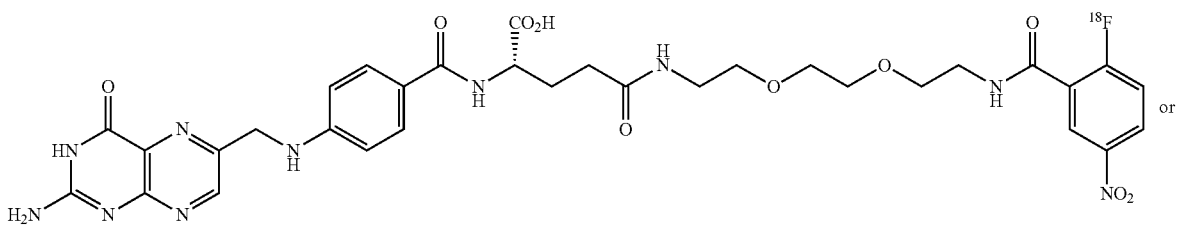

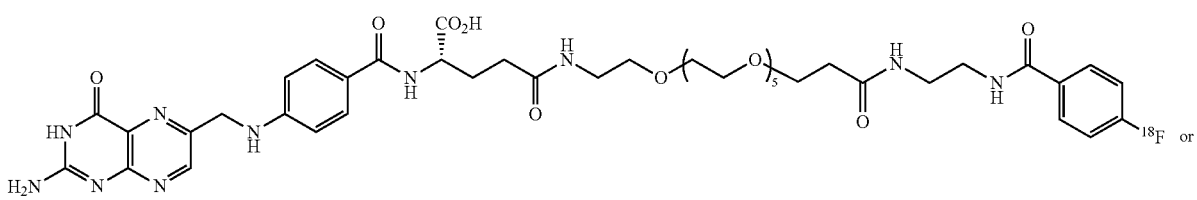

-continued

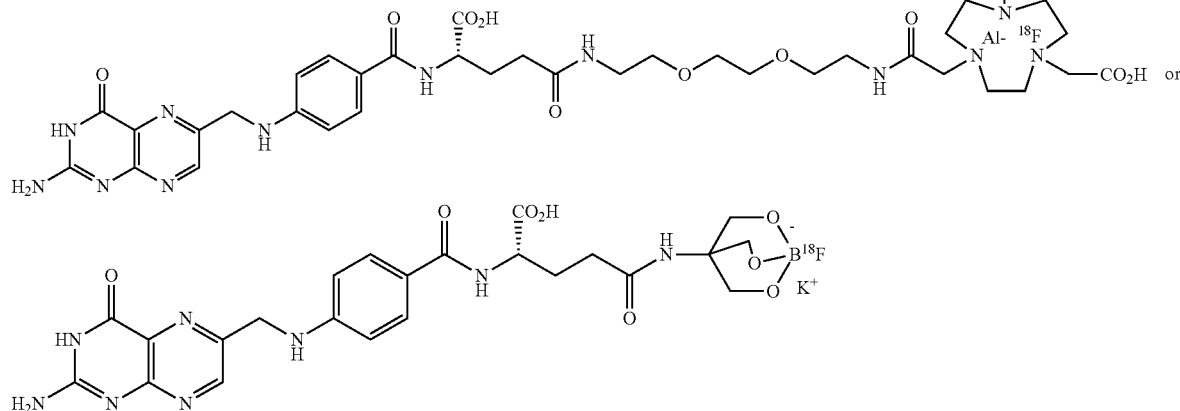

or a pharmaceutically acceptable salt of any of these compounds.

50. The method or use of any one of clauses 1-5, 9 to 36, or 44 to 48 wherein the folate-imaging agent conjugate has the formula:

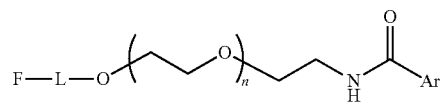

wherein F is a folate ligand, L is an optional bivalent linker; n is an integer selected from 1 to about 100, or from 1 to about 20, or n is 1, 2, 3, 4, 5, 6, 7, or 8; Ar is an aryl group, including heteroaryl groups, that includes one or more substituents $R^f$ comprising a radiophore or a precursor to a radiophore.

51. The method or use of any one of clauses 1-5, 9 to 36, or 44 to 48 wherein the folate-imaging agent conjugate has the formula:

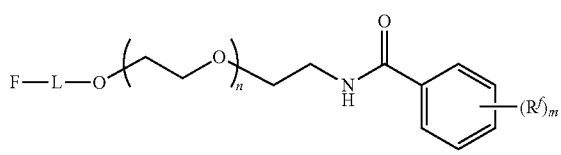

wherein F is a folate ligand; L is an optional bivalent linker; n is an integer selected from 1 to about 100, or from 1 to about 20, or n is 1, 2, 3, 4, 5, 6, 7, or 8; $R^f$ is as described below; and m is an integer selected from 1 to about 3.

52. The method or use of any one of clauses 1-5, 9 to 36, or 44 to 48 wherein the folate-imaging agent conjugate has the formula:

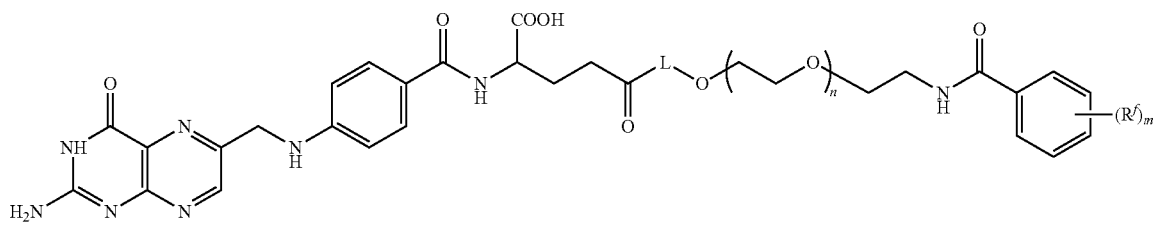

wherein L is an optional bivalent linker; n is an integer selected from 1 to about 100; $R^f$ is as defined in the various embodiments herein; and m is an integer selected from 1 to about 3.

53. A method for selecting a patient for therapy with an anti-inflammatory drug, the method comprising the steps of assessing whether the patient is in need of therapy with the anti-inflammatory drug by relying on the results obtained by means for detecting a signal produced in the patient by a folate-imaging agent conjugate administered to the patient; and prescribing or continuing to prescribe the anti-inflammatory drug to treat the patient assessed to be in need of the anti-inflammatory drug.

54. The method of clause 54 wherein the folate-imaging agent conjugate produces a detectable signal in the patient, wherein the signal is detected, and wherein the detection of the signal is used to assess whether the patient is in need of therapy with the anti-inflammatory drug.

55. The method of clause 54 wherein the signal is a radioactive signal.

56. The method of clause 54 wherein the signal is produced by a chromophore.

57. The method of clause 56 wherein the chromophore is a fluorophore.

58. The method of clause 57 wherein the fluorophore is selected from the group consisting of a fluorescein, a rhodamine, a phycoerythrin, a long wavelength fluorescent dye, and a cyanine.

59. The method of any one of clauses 53 to 58 wherein the signal is produced as a result of binding of the folate-imaging agent conjugate to activated macrophages.

60. The method of any one of clauses 53 to 59 wherein the administration comprises a first administering step and a second administering step.

61. The method of clause 60 wherein the first and second administering steps produce a first signal and a second signal, respectively.

62. The method of clause 61 wherein the first signal and the second signal are quantified.

63. The method of clause 61 wherein the first signal is obtained by administering the folate-imaging agent conjugate prior to administration of the anti-inflammatory drug.

64. The method of clause 61 wherein the first signal is obtained by administering the folate-imaging agent conjugate on the same day as treatment with the anti-inflammatory drug is initiated.

65. The method of clause 61 wherein the second signal is obtained by administering the folate-imaging agent conjugate subsequent to the administration of the anti-inflammatory drug.

66. The method of clause 61 wherein the second signal is obtained by administering the folate-imaging agent conjugate within about 21 days after administration of the anti-inflammatory drug is initiated.

67. The method of clause 61 wherein the second signal is obtained by administering the folate-imaging agent conjugate within about 1 week, about 2 weeks, about 3 weeks, or about 4 weeks after the administration of the anti-inflammatory drug is initiated.

68. The method of clause 61 wherein the second signal is obtained by administering the folate-imaging agent conjugate on any one of the days within about 21 days after the administration of the anti-inflammatory drug is initiated.

69. The method of clause 61 wherein the second signal is obtained by administering the folate-imaging agent conjugate on any one of the days within about 12 weeks after the administration of the anti-inflammatory drug is initiated.

70. The method of clause 61 wherein the second signal is reduced by about 10%, about 20%, about 30%, about 40%, about 50%, about 60%, about 70%, about 80%, about 90%, or about 100% compared to the first signal, and wherein the reduction indicates that the patient should continue to be treated with the anti-inflammatory drug.

71. The method of clause 61 wherein the second signal is obtained by administering the folate-imaging agent conjugate about 2, about 3, about 4, about 5, about 6, about 12, about 15, or about 21 days after the administration of the anti-inflammatory drug is initiated.

72. The method of any one of clauses 53 to 71 wherein the inflammatory disease is selected from the group consisting of arthritis, osteoarthritis, rheumatoid arthritis, atherosclerosis, psoriasis, ischemia/reperfusion injury, pulmonary fibrosis, organ transplant rejection, ulcerative colitis, impact trauma, osteomyelitis, multiple sclerosis, scleroderma, Crohn's disease, Sjögren's syndrome, glomerulonephritis, systemic sclerosis, sarcoidosis, an inflammatory lesion, and chronic inflammation.

73. The method of any one of clauses 53 to 72 wherein the folate-imaging agent conjugate is in a parenteral dosage form.

74. The method of clause 73 wherein the dosage form is selected from the group consisting of an intradermal, a subcutaneous, an intramuscular, an intraperitoneal, an intravenous, and an intrathecal dosage form.

75. The method of any one of clauses 53 to 74 wherein the folate-imaging agent conjugate is in a composition and wherein the composition further comprises a pharmaceutically acceptable carrier.

76. The method of clause 75 wherein the pharmaceutically acceptable carrier is a liquid carrier.

77. The method of clause 76 wherein the liquid carrier is selected from the group consisting of saline, glucose, alcohols, glycols, esters, amides, and a combination thereof.

78. The method of any one of clauses 53 to 77 wherein the folate-imaging agent conjugate is administered in an effective amount.

79. The method of clause 78 wherein the effective amount ranges from about 1 ng to about 1 mg per kilogram of body weight of the patient.

80. The method of clause 78 wherein the effective amount ranges from about 100 ng to about 500 µg per kilogram of body weight of the patient.

81. The method of clause 78 wherein the effective amount ranges from about 100 ng to about 25 µg per kilogram of body weight of the patient.

82. The method of clause 78 wherein the effective amount ranges from about 1 µg/m$^2$ to about 500 mg/m$^2$ of body surface area of the patient.

83. The method of clause 78 wherein the effective amount ranges from about 1 µg/m$^2$ to about 300 mg/m$^2$ of body surface area of the patient.

84. The method of clause 78 wherein the effective amount ranges from about 10 µg/kg to about 100 µg/kg of patient body weight.

85. The method of any one of clauses 53 to 84 further comprising the step of administering unlabeled folic acid to the patient.

86. The method of clause 85 wherein the unlabeled folic acid is administered before administration of the folate-imaging agent conjugate.

87. The method of any one of clauses 53 to 55 or 59 to 86 wherein the folate-imaging agent conjugate has the formula 88. The method of any one of clauses 53 to 55 or 59 to 87 wherein the folate-imaging agent conjugate has the formula

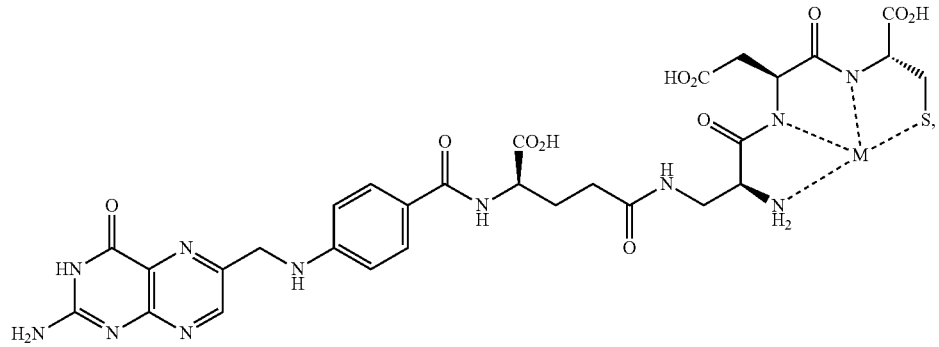

wherein M is a radionuclide.

89. The method of clause 87 or 88 wherein the radionuclide is selected from the group consisting of an isotope of gallium, an isotope of indium, an isotope of copper, an isotope of technetium, and an isotope of rhenium.

90. The method of clause 89 wherein the radionuclide is an isotope of technetium.

91. The method of clause 90 wherein the technecium is $^{99m}$-technetium.

92. The method of any one of clauses 53 to 55 or 59 to 91 wherein the folate-imaging imaging agent conjugate is $^{99m}$Tc-EC20.

93. The method of any one of clauses 53 to 55 or 59 to 92 wherein the signal is detected using scintigraphic imaging.

94. The method of any one of clauses 53 to 93 wherein the patient is a human patient.

95. The method of any one of clauses 53 to 93 wherein the patient is a veterinary patient.

96. The method of any one of clauses 53 to 55 or 59 to 95 wherein the folate-imaging agent conjugate has a radiochemical purity of at least 90% based on weight percentage.

97. The method of any one of clauses 53 to 96 wherein the folate-imaging agent conjugate is in the form of a reconstituted lyophilizate.

98. The method of any one of clauses 53 to 97 wherein the folate-imaging agent conjugate is in a sterile, pyrogen-free aqueous solution.

99. The method of any one of clauses 53-55, 59 to 86, or 94 to 98 wherein the folate-imaging agent conjugate has the formula:

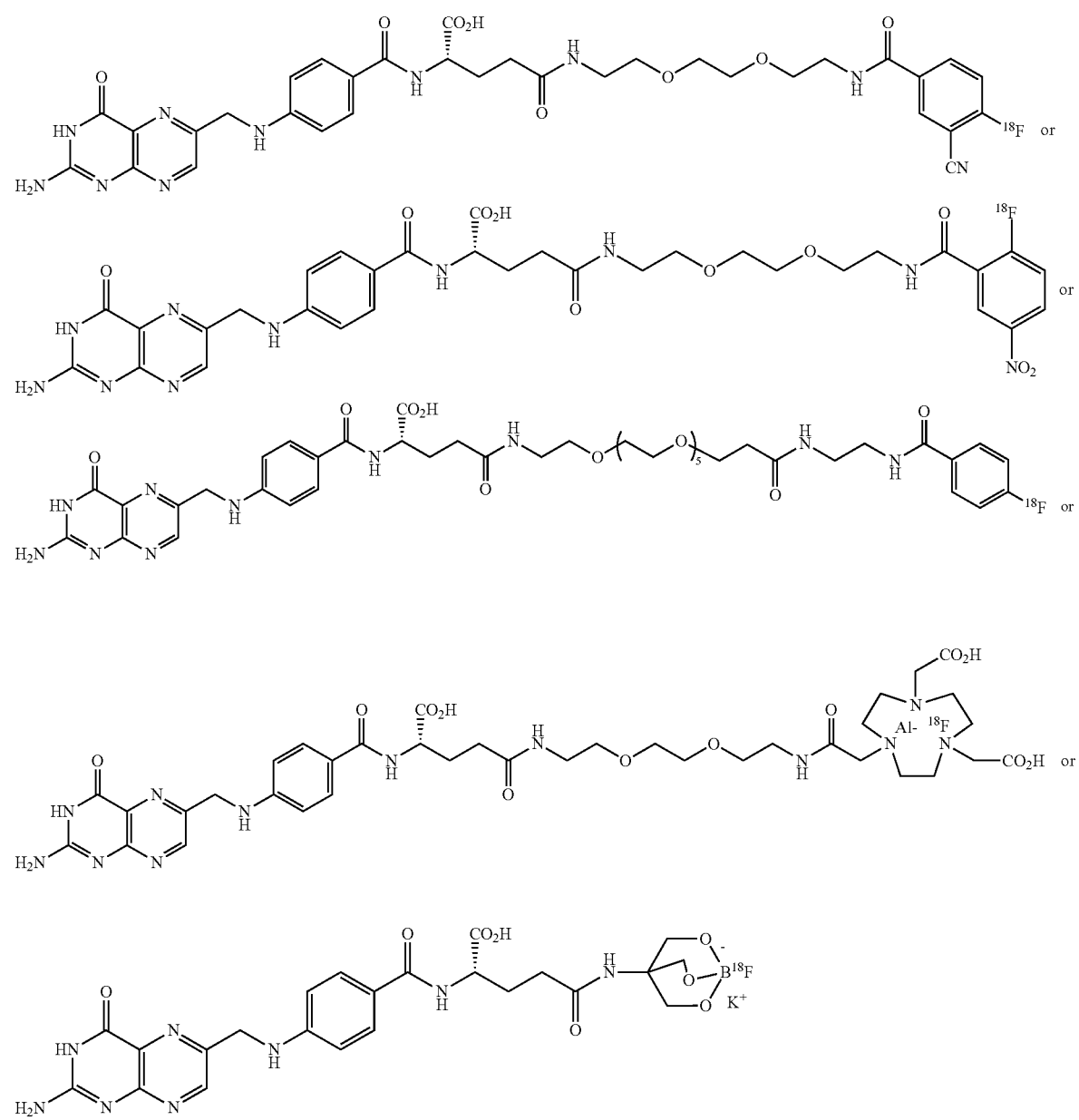

or a pharmaceutically acceptable salt of any of these compounds.

100. The method of any one of clauses 53-55, 59 to 86, or 94 to 98 wherein the folate-imaging agent conjugate has the formula:

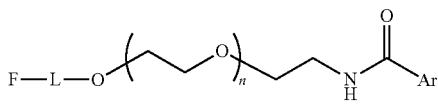

wherein F is a folate ligand, L is an optional bivalent linker; n is an integer selected from 1 to about 100, or from 1 to about 20, or n is 1, 2, 3, 4, 5, 6, 7, or 8; Ar is an aryl group, including heteroaryl groups, that includes one or more substituents $R^f$ comprising a radiophore or a precursor to a radiophore.

101. The method of any one of clauses 53-55, 59 to 86, or 94 to 98 wherein the folate-imaging agent conjugate has the formula:

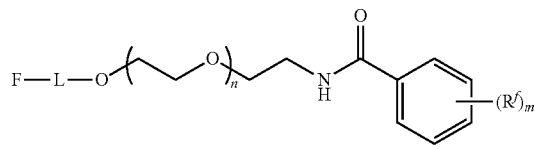

wherein F is a folate ligand; L is an optional bivalent linker; n is an integer selected from 1 to about 100, or from 1 to about 20, or n is 1, 2, 3, 4, 5, 6, 7, or 8; $R^f$ is as described below; and m is an integer selected from 1 to about 3.

102. The method of any one of clauses 53-55, 59 to 86, or 94 to 98 wherein the folate-imaging agent conjugate has the formula:

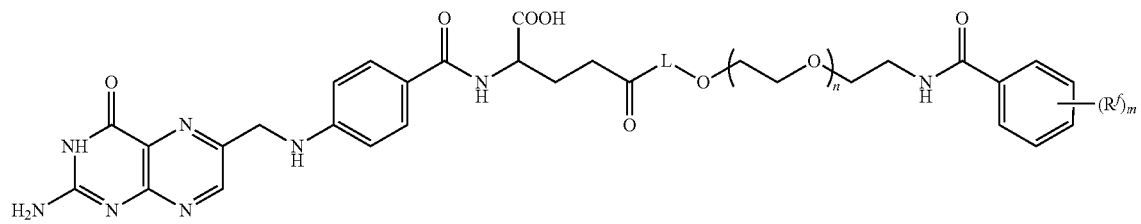

wherein L is an optional bivalent linker; n is an integer selected from 1 to about 100; $R^f$ is as defined in the various embodiments herein; and m is an integer selected from 1 to about 3.

103. A method for predicting the efficacy of an anti-inflammatory drug in a patient, the method comprising the steps of administering to the patient a folate-imaging agent conjugate, and using the folate-imaging agent conjugate to predict efficacy of the anti-inflammatory drug in the patient.

104. The method of clause 103 wherein the folate-imaging agent conjugate produces a detectable signal in the patient, wherein the signal is detected, and wherein the detection of the signal is used to assess whether the patient is in need of therapy with the anti-inflammatory drug.

105. The method of clause 104 wherein the signal is a radioactive signal.

106. The method of clause 104 wherein the signal is produced by a chromophore.

107. The method of clause 106 wherein the chromophore is a fluorophore.

108. The method of clause 107 wherein the fluorophore is selected from the group consisting of a fluorescein, a rhodamine, a phycoerythrin, a long wavelength fluorescent dye, and a cyanine.

109. The method of any one of clauses 104 to 108 wherein the signal is produced as a result of binding of the folate-imaging agent conjugate to activated macrophages.

110. The method of any one of clauses 103 to 109 wherein the administering step comprises a first administering step and a second administering step.

111. The method of clause 110 wherein the first and second administering steps produce a first signal and a second signal, respectively.

112. The method of clause 111 wherein the first signal and the second signal are quantified.

113. The method of clause 111 wherein the first signal is obtained by administering the folate-imaging agent conjugate prior to administration of the anti-inflammatory drug.

114. The method of clause 111 wherein the first signal is obtained by administering the folate-imaging agent conjugate on the same day as treatment with the anti-inflammatory drug is initiated.

115. The method of clause 111 wherein the second signal is obtained by administering the folate-imaging agent conjugate subsequent to the administration of the anti-inflammatory drug.

116. The method of clause 111 wherein the second signal is obtained by administering the folate-imaging agent conjugate within about 21 days after administration of the anti-inflammatory drug is initiated.

117. The method of clause 111 wherein the second signal is obtained by administering the folate-imaging agent conjugate within about 1 week, about 2 weeks, about 3 weeks, or about 4 weeks after the administration of the anti-inflammatory drug is initiated.

118. The method of clause 111 wherein the second signal is obtained by administering the folate-imaging agent conjugate on any one of the days within about 21 days after the administration of the anti-inflammatory drug is initiated.

119. The method of clause 111 wherein the second signal is obtained by administering the folate-imaging agent conjugate on any one of the days within about 12 weeks after the administration of the anti-inflammatory drug is initiated.

120. The method of clause 111 wherein the second signal is reduced by about 10%, about 20%, about 30%, about 40%, about 50%, about 60%, about 70%, about 80%, about 90%, or about 100% compared to the first signal, and wherein the reduction indicates that the patient should continue to be treated with the anti-inflammatory drug.

121. The method of clause 111 wherein the second signal is obtained by administering the folate-imaging agent conjugate about 2, about 3, about 4, about 5, about 6, about 12, about 15, or about 21 days after the administration of the anti-inflammatory drug is initiated.

122. The method of any one of clauses 103 to 121 wherein the inflammatory disease is selected from the group consisting of arthritis, osteoarthritis, rheumatoid arthritis, atherosclerosis, psoriasis, ischemia/reperfusion injury, pulmonary fibrosis, organ transplant rejection, ulcerative colitis, impact trauma, osteomyelitis, multiple sclerosis, scleroderma, Crohn's disease, Sjögren's syndrome, glomerulonephritis, systemic sclerosis, sarcoidosis, an inflammatory lesion, and chronic inflammation.

123. The method of any one of clauses 103 to 122 wherein the folate-imaging agent conjugate is in a parenteral dosage form.

124. The method of clause 123 wherein the dosage form is selected from the group consisting of an intradermal, a subcutaneous, an intramuscular, an intraperitoneal, an intravenous, and an intrathecal dosage form.

125. The method of any one of clauses 103 to 124 wherein the folate-imaging agent conjugate is in a composition and wherein the composition further comprises a pharmaceutically acceptable carrier.

126. The method of clause 125 wherein the pharmaceutically acceptable carrier is a liquid carrier.

127. The method of clause 126 wherein the liquid carrier is selected from the group consisting of saline, glucose, alcohols, glycols, esters, amides, and a combination thereof.

128. The method of any one of clauses 103 to 127 wherein the folate-imaging agent conjugate is administered in an effective amount.

129. The method of clause 128 wherein the effective amount ranges from about 1 ng to about 1 mg per kilogram of body weight of the patient.

130. The method of clause 128 wherein the effective amount ranges from about 100 ng to about 500 µg per kilogram of body weight of the patient.

131. The method of clause 128 wherein the effective amount ranges from about 100 ng to about 25 µg per kilogram of body weight of the patient.

132. The method of clause 128 wherein the effective amount ranges from about 1 µg/m$^2$ to about 500 mg/m$^2$ of body surface area of the patient.

133. The method of clause 128 wherein the effective amount ranges from about 1 µg/m$^2$ to about 300 mg/m$^2$ of body surface area of the patient.

134. The method of clause 128 wherein the effective amount ranges from about 10 µg/kg to about 100 µg/kg of patient body weight.

135. The method of any one of clauses 103 to 134 further comprising the step of administering unlabeled folic acid to the patient.

136. The method of clause 135 wherein the unlabeled folic acid is administered before administration of the folate-imaging agent conjugate.

137. The method of any one of clauses 103 to 105 or 109 to 136 wherein the folate-imaging agent conjugate has the formula

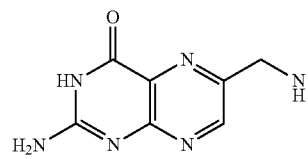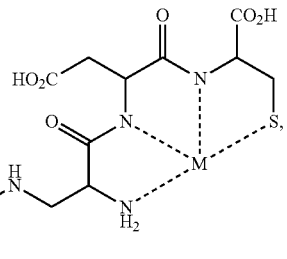

wherein M is a radionuclide.

138. The method of any one of clauses 103 to 105 or 109 to 137 wherein the folate-imaging agent conjugate has the formula

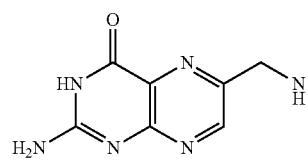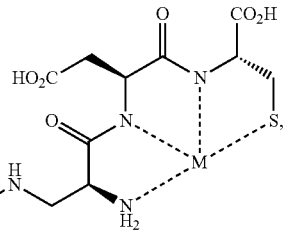

wherein M is a radionuclide.

139. The method of clause 137 or 138 wherein the radionuclide is selected from the group consisting of an isotope of gallium, an isotope of indium, an isotope of copper, an isotope of technetium, and an isotope of rhenium.

140. The method of clause 139 wherein the radionuclide is an isotope of technetium.

141. The method of clause 140 wherein the technecium is $^{99m}$-technetium.

142. The method of any one of clauses 103 to 105 or 109 to 141 wherein the folate-imaging agent conjugate is $^{99m}$Tc-EC20.

143. The method of any one of clauses 103 to 105 or 109 to 142 wherein the signal is detected using scintigraphic imaging.

144. The method of any one of clauses 103 to 143 wherein the patient is a human patient.

145. The method of any one of clauses 103 to 143 wherein the patient is a veterinary patient.

146. The method of any one of clauses 103 to 105 or 109 to 145 wherein the folate-imaging agent conjugate has a radiochemical purity of at least 90% based on weight percentage.

147. The method of any one of clauses 103 to 146 wherein the folate-imaging agent conjugate is in the form of a reconstituted lyophilizate.

148. The method of any one of clauses 103 to 147 wherein the folate-imaging agent conjugate is in a sterile, pyrogen-free aqueous solution.

149. The method of any one of clauses 103-105, 109 to 136, or 144 to 148 wherein the folate-imaging agent conjugate has the formula:

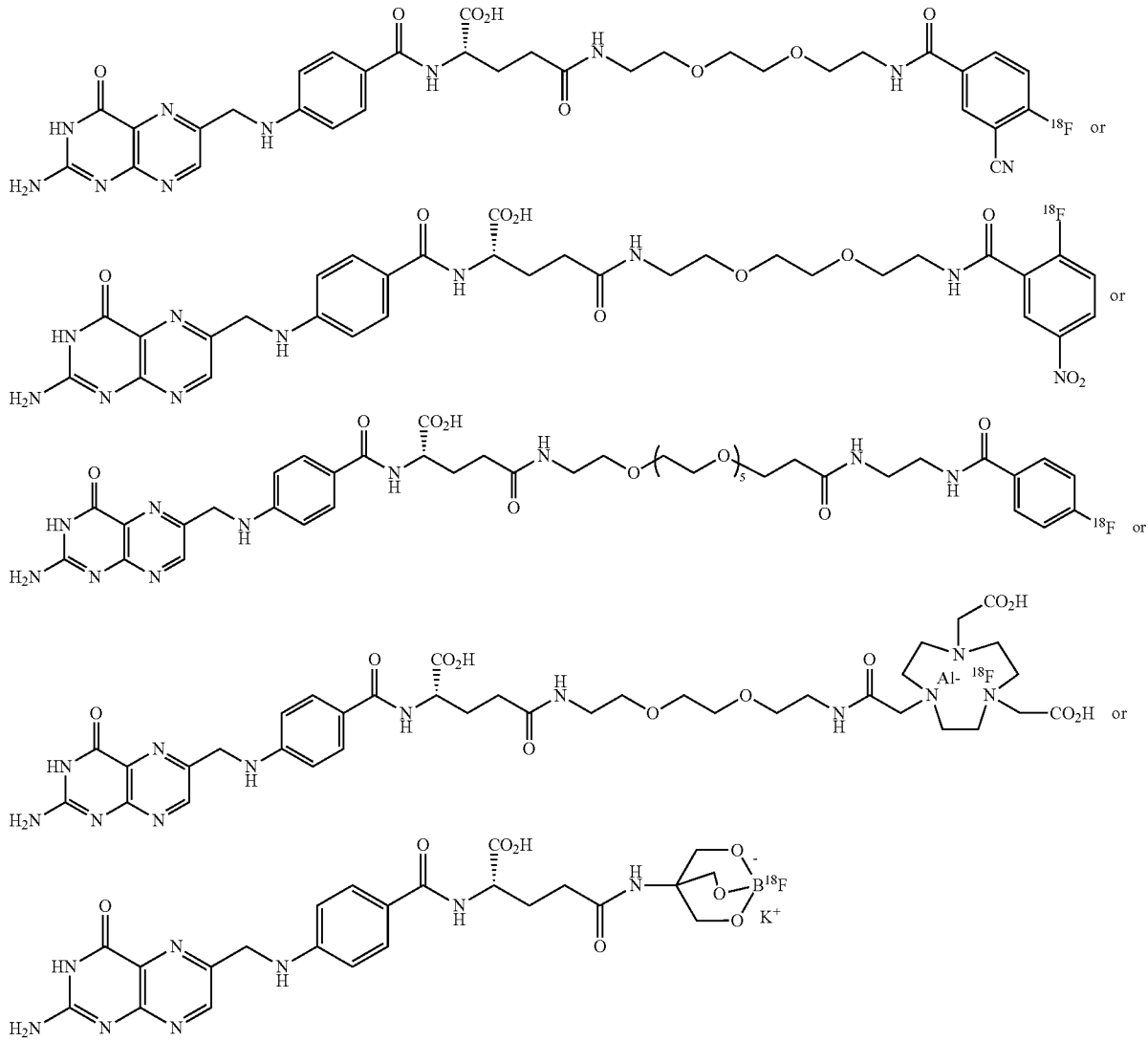

or a pharmaceutically acceptable salt of any of these compounds.

150. The method of any one of clauses 103-105, 109 to 136, or 144 to 148 wherein the folate-imaging agent conjugate has the formula:

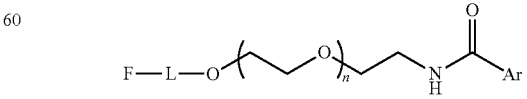

wherein F is a folate ligand, L is an optional bivalent linker; n is an integer selected from 1 to about 100, or from 1 to about 20, or n is 1, 2, 3, 4, 5, 6, 7, or 8; Ar is an aryl group, including heteroaryl groups, that includes one or more substituents R^f comprising a radiophore or a precursor to a radiophore.

151. The method of any one of clauses 103-105, 109 to 136, or 144 to 148 wherein the folate-imaging agent conjugate has the formula:

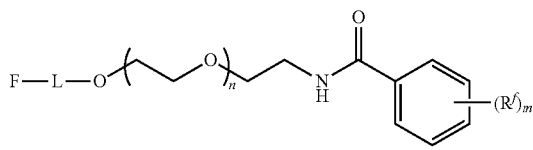

wherein F is a folate ligand; L is an optional bivalent linker; n is an integer selected from 1 to about 100, or from 1 to about 20, or n is 1, 2, 3, 4, 5, 6, 7, or 8; R^f is as described below; and m is an integer selected from 1 to about 3.

152. The method of any one of clauses 103-105, 109 to 136, or 144 to 148 wherein the folate-imaging agent conjugate has the formula:

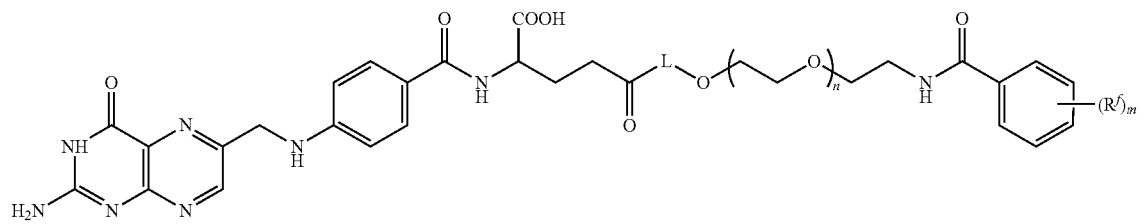

wherein L is an optional bivalent linker; n is an integer selected from 1 to about 100; R^f is as defined in the various embodiments herein; and m is an integer selected from 1 to about 3.

153. The method of use of any one of clauses 1 to 152 wherein the folate portion of the folate-imaging agent conjugate comprises a compound of the formula:

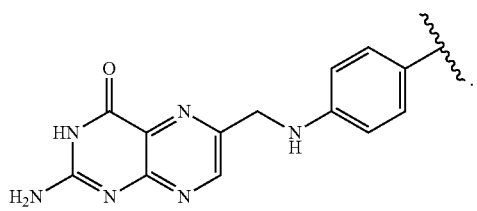 [SMILES: *c1ccc(NCc2cnc3nc(N)[nH]c(=O)c3n2)cc1]

154. The method or use of any one of clauses 1-4, 9-36, 44-45, 47-48, 53-54, 59-86, 94-95, 97-98, 103-104, 109-136, or 144-148 wherein the folate-imaging agent conjugate has the formula:

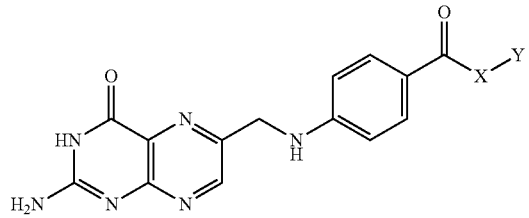

wherein:

X is an amino acid or a derivative thereof, and

Y is a dye that has a fluorescence excitation and emission spectra in the near infrared range, and said compound maintains or enhances the fluorescence of Y.

155. The method or use of any one of clauses 1-4, 9-36, 44-45, 47-48, 53-54, 59-86, 94-95, 97-98, 103-104, 109-136, or 144-148 wherein the imaging agent Y has the formula:

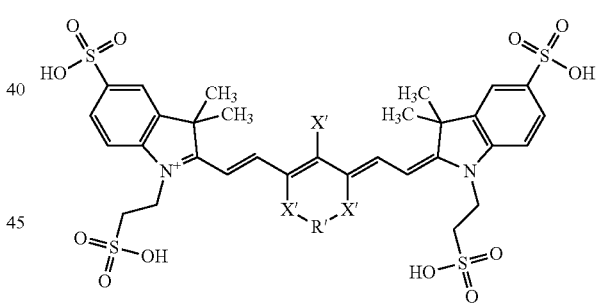

wherein:

X' is independently selected from the group consisting of O, S, N and C, and

R' is independently selected from the group consisting of CH2 and CH2CH2. In some embodiments, the dye Y is selected from the group consisting of LS288, IR800, SP054, S0121, KODAK IRD28, S2076, S0456 and derivatives thereof.

156. The method or use of any one of clauses of clauses 1-4, 9-36, 44-45, 47-48, 53-54, 59-86, 94-95, 97-98, 103-104, 109-136, or 144-148 wherein the folate-imaging agent conjugate has the formula:

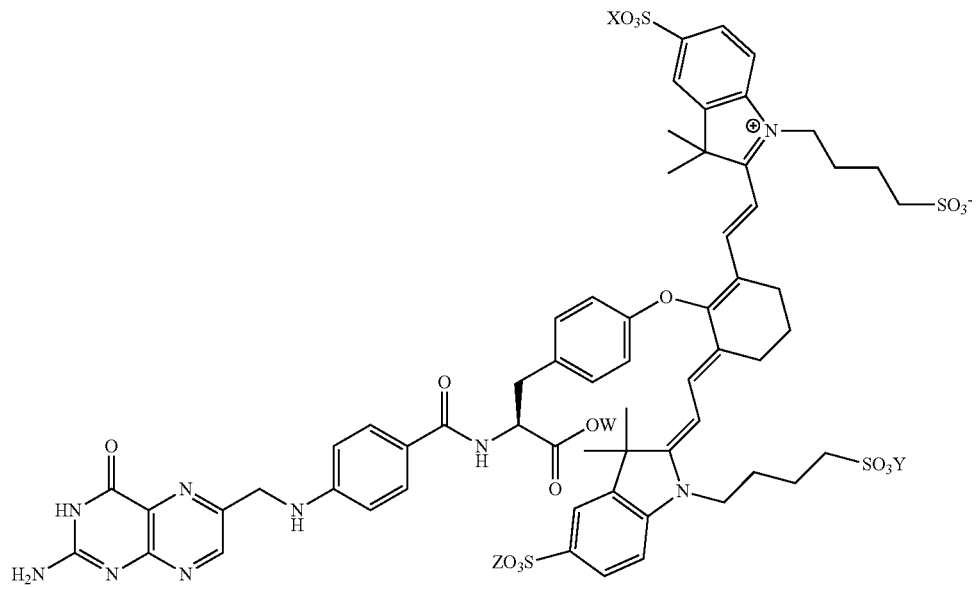

wherein W, X, Y, Z each are H, Na+, K+ or NH4+. This compound is referred to herein as OTL-38 or OTL-0038.

In any of the various embodiments described herein, the following features may be present where applicable, providing additional embodiments of the invention. For all of the embodiments described herein, any applicable combination of embodiments is also contemplated. Any applicable combination of the above-described embodiments is also considered to be in accordance with the invention.

The invention relates to methods and compositions for the selection of patients for therapy with an anti-inflammatory drug. More particularly, the invention relates to compositions comprising folate-imaging agent conjugates for the selection of patients for therapy with an anti-inflammatory drug, and methods and uses therefor.

In one embodiment, a method is provided for selecting a patient for therapy with an anti-inflammatory drug. The method comprises the steps of administering to the patient a folate-imaging agent conjugate, and using the folate-imaging agent conjugate to predict the response of the patient to the anti-inflammatory drug.

In another embodiment, a use is provided of a folate-imaging agent conjugate for selecting a patient for therapy with an anti-inflammatory drug. The folate-imaging agent conjugate is administered to the patient and is used to predict the response of the patient to the anti-inflammatory drug.

In yet another embodiment, a use is provided of a folate-imaging agent conjugate in the manufacture of a medicament for selecting a patient for therapy with an anti-inflammatory drug. The folate-imaging agent conjugate is administered to the patient and is used to predict the response of the patient to the anti-inflammatory drug.

In another illustrative embodiment, a method for selecting a patient for therapy with an anti-inflammatory drug is provided. The method comprises the steps of assessing whether the patient is in need of therapy with the anti-inflammatory drug by relying on the results obtained by means for detecting a signal produced in the patient by a folate-imaging agent conjugate administered to the patient; and prescribing or continuing to prescribe the anti-inflammatory drug to treat the patient assessed to be in need of the anti-inflammatory drug.

The folate-imaging agent conjugate produces a detectable signal in the patient, the signal is detected, and detection of the signal is used to predict the response of the patient to the anti-inflammatory drug. Without being bound by theory, the signal may be produced as a result of the binding of folate-imaging agent conjugates to activated macrophages at a site of inflammation, and/or may result from accumulation of folate-imaging agent conjugates in activated macrophages at a site of inflammation.

In all of the above-described embodiments, the folate-imaging agent conjugate is administered to the patient and is used to predict the response of the patient to the anti-inflammatory drug. The administering step can comprise a first administering step and a second administering step. The first and second administering steps can produce a first signal and a second signal, respectively.

In another illustrative aspect, the first signal and the second signal can be quantified, and compared to each other to determine if there is a reduction in the intensity of the second signal compared to the first signal. In these embodiments, a reduction in the intensity of the second signal compared to the first signal can indicate that the patient will benefit from continuation of treatment with an anti-inflammatory drug. The patient may then be treated with the anti-inflammatory drug, or treatment with the anti-inflammatory drug may be continued, if the patient was already being treated with the anti-inflammatory drug.

In one embodiment, the first signal is obtained by administering the folate-imaging agent conjugate prior to administration of the anti-inflammatory drug to obtain a "control" level of signal intensity prior to treatment with the anti-inflammatory drug. In another embodiment, the first signal is obtained by administering the folate-imaging agent conjugate on the same day as treatment with the anti-inflammatory drug is initiated to obtain a "control" level of signal intensity. The second signal can be obtained by administering the folate-imaging agent conjugate subsequent to the administration of the anti-inflammatory drug to determine the level of signal intensity after treatment with the anti-inflammatory drug for a period of time. Without being bound by theory, a reduction in the intensity of the second signal compared to the first signal may reflect a reduction in the number of inflammatory cells capable of binding folate-imaging agent conjugates, such as activated macrophages, at the site of inflammation, inactivation of inflammatory cells at the site of inflammation, a reduction in the capacity of inflammatory cells to bind folate-imaging agent conjugates, a reduction in accumulation of folate-imaging agent conjugates in inflammatory cells at the site of inflammation, or any other response caused by the anti-inflammatory drug that reduces the signal intensity produced by folate-imaging agent conjugates at a site of inflammation.

In one of the above described embodiments, the second signal is obtained by administering the folate-imaging agent conjugate subsequent to the administration of the anti-inflammatory drug. In one illustrative embodiment, the second signal is obtained by administering the folate-imaging agent conjugate within about 21 days after administration of the anti-inflammatory drug is initiated. In another embodiment, the second signal is obtained by administering the folate-imaging agent conjugate on any one of the days within about 21 days after the administration of the anti-inflammatory drug is initiated. In another aspect, the second signal is obtained by administering the folate-imaging agent conjugate within about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks after the administration of the anti-inflammatory drug is initiated. In another illustrative embodiment, the second signal is obtained by administering the folate-imaging agent conjugate on any one of the days within about 12 weeks after the administration of the anti-inflammatory drug is initiated. In another embodiment, the second signal is obtained by administering the folate-imaging agent conjugate on day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, or day 24 after the administration of the anti-inflammatory drug is initiated. The day the administration of the anti-inflammatory drug is initiated is day 0. Additional signals may be obtained by using a third, fourth, etc. administration step of the folate-imaging agent conjugate. Any additional administrations of the folate-imaging agent conjugate may be done at any of the times described in this paragraph.

As described herein, the first signal is obtained by administering the folate-imaging agent conjugate prior to administration of the anti-inflammatory drug, or on the same day as treatment with the anti-inflammatory drug is initiated, to obtain a "control" level of signal intensity prior to treatment with the anti-inflammatory drug. The second signal can be obtained by administering the folate-imaging agent conjugate subsequent to the administration of the anti-inflammatory drug to determine the level of signal intensity after treatment with the anti-inflammatory drug for a period of time. The first signal and the second signal can be quantified, and compared to each other to determine if there is a reduction in the intensity of the second signal compared to the first signal. In these embodiments, a reduction in the intensity of the second signal compared to the first signal can indicate that the patient will benefit from continued treatment with an anti-inflammatory drug, or will not benefit from continuation of treatment with the anti-inflammatory drug. If it is determined that the patient will not benefit from treatment with a particular anti-inflammatory drug, a different anti-inflammatory drug can be used. The methods and uses described herein can be used to determine whether the new anti-inflammatory drug will benefit the patient.

In various embodiments, the second signal can be reduced by about 10%, about 20%, about 30%, about 40%, about 50%, about 60%, about 70%, about 80%, about 90%, or about 100% compared to the first signal. For any of these embodiments, the reduction may indicate that the patient should continue to be treated with the anti-inflammatory drug.

In an alternate embodiment, the methods and uses described herein can be used to predict the response of a patient to an anti-inflammatory drug by making a determination whether the patient is expected to benefit from initiation of treatment, rather than continued treatment, with an anti-inflammatory drug, or whether the patient is not expected to benefit from initiation of treatment of treatment with an anti-inflammatory drug. In such embodiments, folate-imaging agent conjugates are administered, in the absence of treatment with an anti-inflammatory drug, and the intensity of the signal obtained is used to determine whether the patient is expected to benefit from initiation of treatment with an anti-inflammatory drug, or is not expected to benefit from initiation of treatment of treatment with an anti-inflammatory drug.

The methods and uses described herein are applicable to any anti-inflammatory drugs used to treat a patient with an inflammatory disease. Anti-inflammatory drugs include, but are not limited to, non-steroidal anti-inflammatory drugs (NSAID), analgesics, glucocorticoids, anti-rheumatic drugs, dihydrofolate reductase inhibitors, TNF-α inhibitors, biologic response modifiers, hormonal agents, and combinations thereof. Other exemplary anti-inflammatory drugs include corticosteroids, hydrocortisone, prednisolone, prednisone, allopurinol, aspirin, indomethacin, phenylbutazone, etanercept, infliximab, adalimumab, rituximab, abatacept, anakinra, efalizumab, methotrexate, dexamethasone, naproxen, and combinations thereof.

In the various embodiments described herein, the methods or uses described herein are applicable to inflammatory diseases, including, but not limited to, inflammatory diseases selected from the group consisting of arthritis, osteoarthritis, rheumatoid arthritis, atherosclerosis, psoriasis, ischemia/reperfusion injury, pulmonary fibrosis, organ transplant rejection, ulcerative colitis, impact trauma, osteomyelitis, multiple sclerosis, scleroderma, Crohn's disease, Sjögren's syndrome, glomerulonephritis, systemic sclerosis, sarcoidosis, an inflammatory lesion, and chronic inflammation.

The methods and uses described herein, can be used for both human clinical medicine and veterinary applications. Thus, the patient can be human or, in the case of veterinary applications, can be a laboratory, agricultural, domestic, or wild animal. The methods and uses described herein can be applied to humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

As used herein, the term "folate-imaging agent conjugate" for the methods and uses described herein, means a folate ligand linked to an imaging agent. Thus, the folate-imaging agent conjugate comprises a folate ligand linked to an imaging agent. The folate-imaging agent conjugates described below provide a means for detecting a signal in a patient treated with a folate-imaging agent conjugate.

In various embodiments, the folate ligand linked to the imaging agent in the folate-imaging agent conjugate can include, but is not limited to, folate, folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refer to the art-recognized analogs having a carbon atom substituted for one or two nitrogen atoms in the naturally occurring folic acid structure, or analog or derivative thereof. For example, the deaza analogs include the 1-deaza, 3-deaza, 5-deaza, 8-deaza, and 10-deaza analogs of folate, folinic acid, pteropolyglutamic acid, and folate receptor-binding pteridines such as tetrahydropterins, dihydrofolates, and tetrahydrofolates. The dideaza analogs include, for example, 1,5-dideaza, 5,10-dideaza, 8,10-dideaza, and 5,8-dideaza analogs of folate, folinic acid, pteropolyglutamic acid, and folate receptor-binding pteridines such as tetrahydropterins, dihydrofolates, and tetrahydrofolates. Other folates useful to form folate-imaging agent conjugates for use in the methods and uses described herein are the folate receptor-binding analogs aminopterin, amethopterin (also known as methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate). The foregoing "folates" bind to folate receptors.

Additional folate ligands that can be used in the folate-imaging agent conjugates have the general formula:

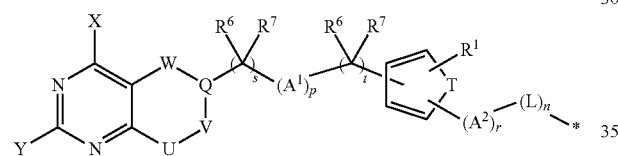

wherein X and Y are each-independently selected from the group consisting of halo, $R^2$, $OR^2$, $SR^3$, and $NR^4R^5$;

U, V, and W represent divalent moieties each independently selected from the group consisting of —($R^{6a}$)C=, —N=, —($R^{6a}$)C($R^{7a}$)—, and —N($R^{4a}$)—; Q is selected from the group consisting of C and CH; T is selected from the group consisting of S, O, N, and —C=C—;

$A^1$ and $A^2$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4a}$)S(O)$_2$—, —C($R^{6b}$)($R^{7b}$)—, —N(C≡CH)—, —N(CH$_2$C≡CH)—, $C_1$-$C_{12}$ alkylene, and $C_1$-$C_{12}$ alkyeneoxy, where Z is oxygen or sulfur;

$R^1$ is selected-from the group consisting of hydrogen, halo, $C_1$-$C_{12}$ alkyl, and $C_1$-$C_{12}$ alkoxy; $R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group; $R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group;

L is a divalent linker as described herein;

n, p, r, s and t are each independently either 0 or 1; and wherein * indicates the attachment point to the rest of the conjugate.

It is appreciated that the forgoing folate ligands can be present in one or more tautomeric forms.

In various embodiments, the imaging agent portion of the folate-imaging agent conjugate can be any imaging agent useful for medical imaging. For example the imaging agent can be a radioactive imaging agent or a chromophore, and the chromophore can be a fluorophore. In one illustrative embodiment, the fluorophore is selected from the group consisting of fluorescein, rhodamine, Texas Red, phycoerythrin, Oregon Green, AlexaFluor 488 (Molecular Probes, Eugene, Oreg.), Cy3, Cy5, and Cy7.

In another aspect, the fluorophore is a fluorescent agent selected from Oregon Green fluorescent agents, including but not limited to Oregon Green 488, Oregon Green 514, and the like, AlexaFluor fluorescent agents, including but not limited to AlexaFluor 488, AlexaFluor 647, and the like, fluorescein, and related analogs, rhodamine fluorescent agents, including but not limited to tetramethylrhodamine, and the like, DyLight fluorescent agents, including but not limited to DyLight 680, and the like, CW 800, Texas Red, phycoerythrin, and others. In another embodiment, the fluorophore is selected from a fluorescein, a rhodamine, a phycoerythrin, a long wavelength fluorescent dye, and a cyanine. Illustrative fluorophores are shown in the following illustrative general structures:

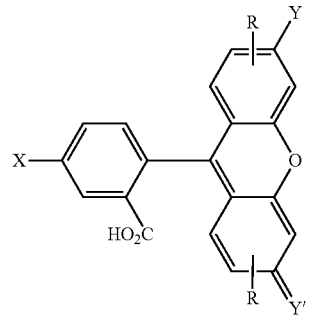

where X is oxygen, nitrogen, or sulfur, and where X is attached to linker L; Y is $OR^a$, $NR^a_2$, or $NR^a_3{}^+$; and Y' is O, $NR^a$, or $NR^a_2{}^+$; where each R is independently selected in each instance from H, fluoro, sulfonic acid, sulfonate, and salts thereof, and the like; and $R^a$ is hydrogen or alkyl, and, in another embodiment,

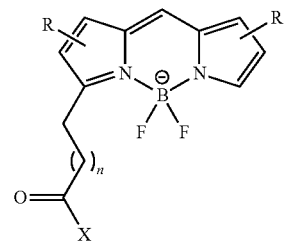

where X is oxygen, nitrogen, or sulfur, and where X is attached to linker L; and each R is independently selected in each instance from H, alkyl, heteroalkyl, and the like; and n is an integer from 0 to about 4.

In another embodiment, the fluorophore has the formula

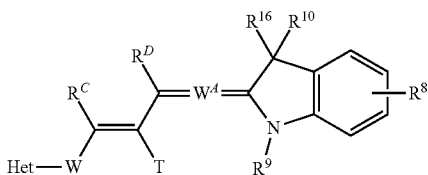

or a salt thereof
wherein
W is a bond or

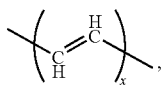

where x is an integer from about 1 to about 4;
$W^A$ is a double bond or

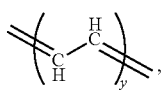

where y is an integer from about 1 to about 4;
$R^C$ and $R^D$ are independently hydrogen or alkyl, or $R^C$ and $R^D$ and the atoms to which they are attached form a cycloalkene;
T is hydrogen, fluoro, chloro, or hydroxy, alkyl, heteroalkyl, alkoxy, aryl, heteroaryl, aryloxy, or heteroaryloxy, each of which is optionally substituted, or T is O, S, $R^{17}N$, where  represents the attachment point to the rest of the conjugate;
$R^8$ represents from 1 to 3 substituents independently selected in each instance from the group consisting of alkyl, heteroalkyl, alkoxy, alkylhydroxy, fluoro, sulfonic acid, or a salt thereof, alkylsulfonic acid, or a salt thereof, or an amine, and an alkylamine; or $R^8$ represents 2 to 3 substituents where at least two substituents are on adjacent carbons and together with the atoms to which they are attached form an optionally substituted fused aromatic ring, and the other substituent, if present, is alkyl, heteroalkyl, alkoxy, alkylhydroxy, fluoro, sulfonic acid, or a salt thereof, alkylsulfonic acid, or a salt thereof, or an amine, and an alkylamine;

$R^{11}$ represents from 1 to 3 substituents independently selected in each instance from the group consisting of alkyl, heteroalkyl, alkoxy, alkylhydroxy, fluoro, sulfonic acid, or a salt thereof, alkylsulfonic acid, or a salt thereof, or an amine, and an alkylamine; or $R^{11}$ represents 2 to 3 substituents where at least two substituents are on adjacent carbons and together with the atoms to which they are attached form a fused aromatic ring, and the other substituent, if present, is alkyl, heteroalkyl, alkoxy, alkylhydroxy, fluoro, sulfonic acid, or a salt thereof, alkylsulfonic acid, or a salt thereof, or an amine, and an alkylamine;
$L_1$ is an alkylene linked via a divalent linker to a folate;
Het is selected from the group consisting of

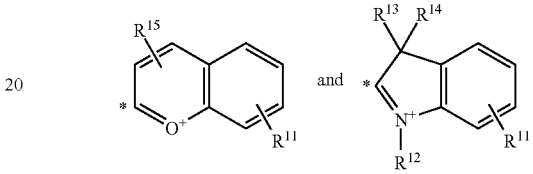

where * is the attachment point to W;
$R^9$, $R^{10}$, $R^{12}$, $R^{13}$, $R^{14}$, and $R^{17}$ are in each instance independently selected from the group consisting of alkyl, heteroalkyl, hydroxyalkyl, alkylamine, aminoalkyl, thioalkyl, alkylsulfonic acid, or salt thereof, and alkylcarboxylic acid, or a salt thereof;
$R^{15}$ represents from 0 to 3 substituents selected from the group consisting of fluoro, alkyl, alkoxy, sulfonic acid, or a salt thereof, and heteroalkyl; and
$R^{16}$ is selected from the group consisting of alkyl, heteroalkyl, hydroxyalkyl, alkylamine, aminoalkyl, thioalkyl, alkylsulfonic acid, or salt thereof, and alkylcarboxylic acid, or a salt thereof; or $R^{16}$ is alkylene* where * represents the attachment point to the rest of the conjugate via a divalent linker. In other embodiments, x is an integer from 0 to 4. In other embodiments, y is an integer from 0 to 4.

In another embodiment, the imaging agent portion of the folate-imaging agent conjugate can be a radioactive imaging agent. For example, the folate-imaging agent conjugate can be a compound of either of the following formulas where the imaging agent is a metal chelator, and wherein M is a radionuclide:

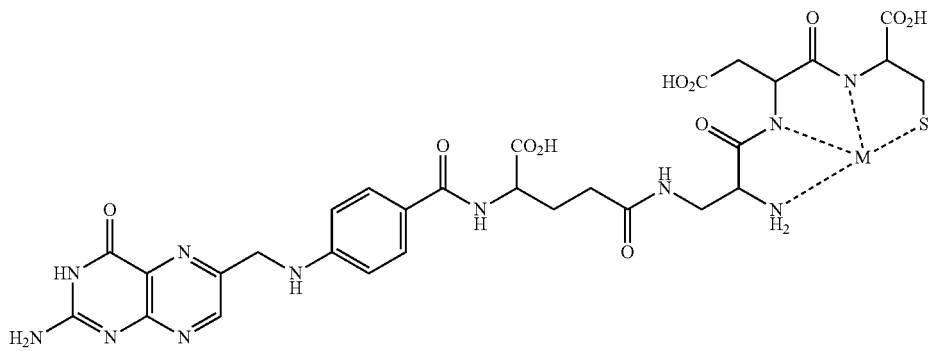

-continued

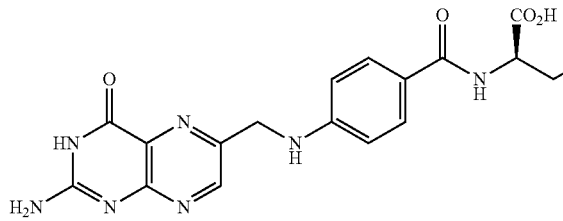

In these embodiments, the radionuclide can be selected from the group consisting of an isotope of gallium, an isotope of indium, an isotope of copper, an isotope of technetium, and an isotope of rhenium. In another embodiment, the radionuclide can be an isotope of technetium. In yet another embodiment, the radionuclide can be $^{99m}$-technicium.

In another embodiment, the imaging agent is technetium-99m-labeled EC20 ($^{99m}$Tc-EC20). $^{99m}$Tc-EC20 has been developed and provides for detection of tissues or cells expressing folate receptors capable of binding folate. $^{99m}$Tc-EC20 has the formula In the context of administration to patients for detecting and assessing tissues and cells expressing folate receptors capable of binding folate, "$^{99m}$Tc-EC20" is used herein to denote the radioactive drug substance, or a pharmaceutically acceptable salt thereof. It will be appreciated that $^{99m}$Tc-EC20 may be present in solution or suspension in an ionized form, including a deprotonated form. "EC20" is used herein to denote the non-radioactive reagent lacking a radionuclide, or a pharmaceutically acceptable salt of EC20. It will be appreciated that EC20 may be present in solution or suspension in an ionized form, including a deprotonated form.

$^{99m}$Tc-EC20

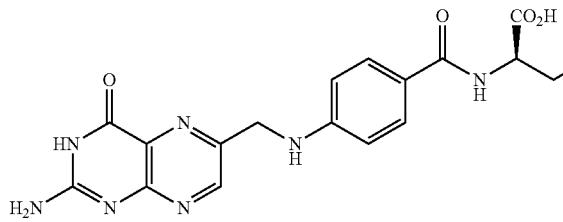

The term EC20 can be used to identify the non-radioactive reagent lacking a radionuclide. EC20 has the formula:

In yet another embodiment, the folate-imaging agent conjugate has the formula:

EC20

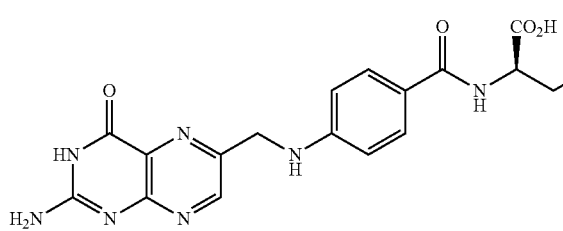

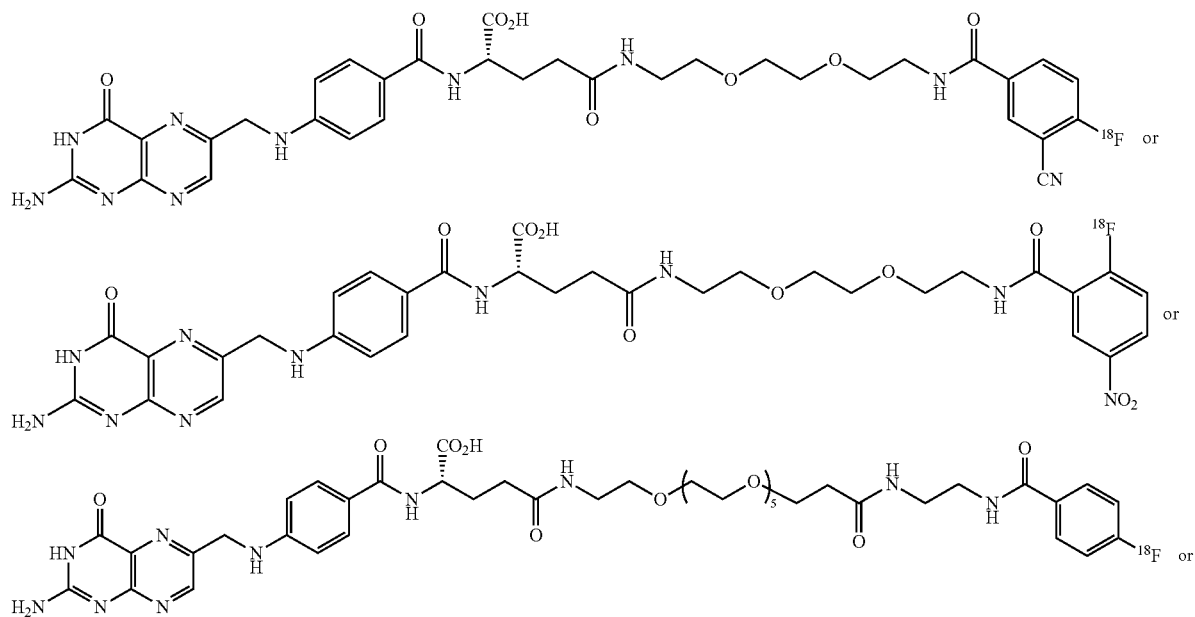

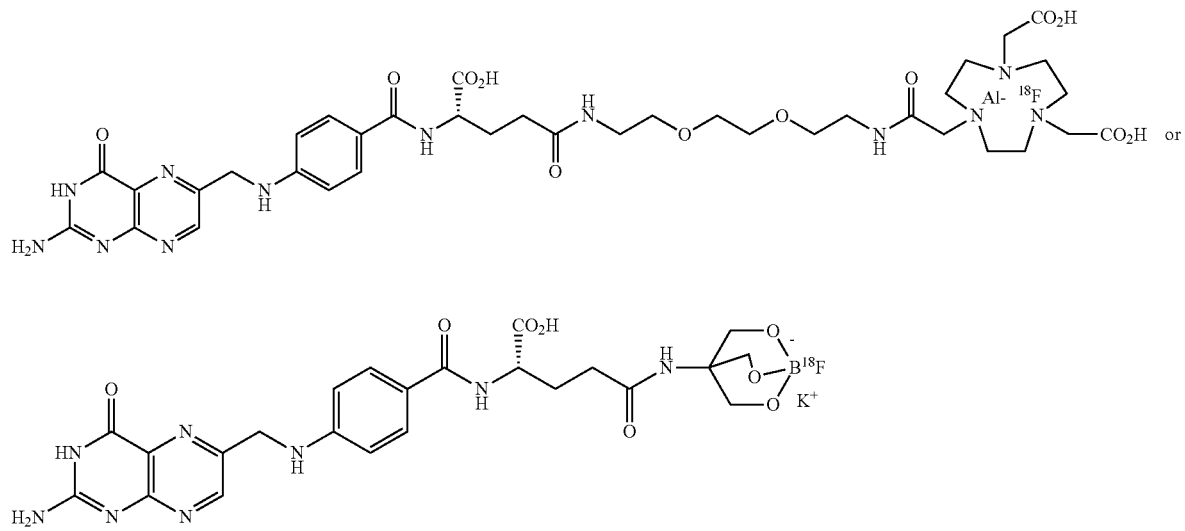

or a pharmaceutically acceptable salt of any of these compounds.

In another embodiment, the folate imaging agent conjugate has the formula:

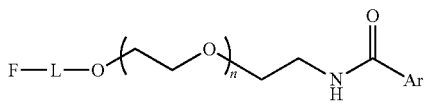

wherein F is a folate ligand, L is an optional bivalent linker; n is an integer selected from 1 to about 100, or from 1 to about 20, or n is 1, 2, 3, 4, 5, 6, 7, or 8; Ar is an aryl group, including heteroaryl groups, that includes one or more substituents $R^f$ comprising a radiophore or a precursor to a radiophore.

In another embodiment, the folate-imaging agent conjugate has the formula:

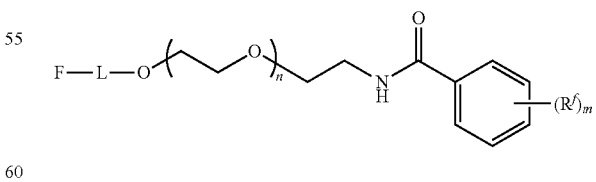

wherein F is a folate ligand; L is an optional bivalent linker; n is an integer selected from 1 to about 100, or from 1 to about 20, or n is 1, 2, 3, 4, 5, 6, 7, or 8; $R^f$ is as described below; and m is an integer selected from 1 to about 3.

In another embodiment of the folate-imaging agent conjugate, has the formula:

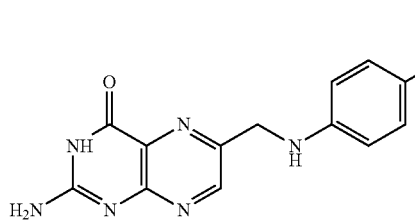
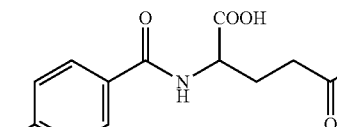

wherein L is an optional bivalent linker; n is an integer selected from 1 to about 100; $R^f$ is as defined in the various embodiments herein; and m is an integer selected from 1 to about 3.

In each of the embodiments described above with $R^f$, a suitable radiophore may be prepared using the fluorine isotope $^{18}F$. Other useful positron-emitting isotopes may also be employed, such as $^{34}Cl$, $^{45}Ti$, $^{51}Mn$, $^{61}Cu$, $^{63}Zn$, $^{82}Rb$, $^{68}Ga$, $^{11}C$, $^{13}N$, $^{15}O$, and $^{18}F$. In one illustrative embodiment, the radioisotope is selected from $^{34}Cl$, $^{64}Cu$, $^{68}Ga$, $^{66}Ga$, or $^{18}F$. In one aspect $R^f$ is $^{18}F$, nitro, or $-N(CH_3)_3^+$.

In another embodiment, the folate ligand portion of the folate-imaging agent conjugate comprises a compound of the formula:

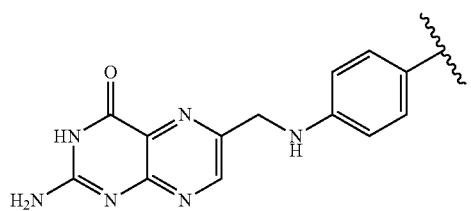 [SMILES: *c1ccc(NCc2cnc3nc(N)[nH]c(=O)c3n2)cc1]

In yet another embodiment, the folate-imaging agent conjugate has the formula:

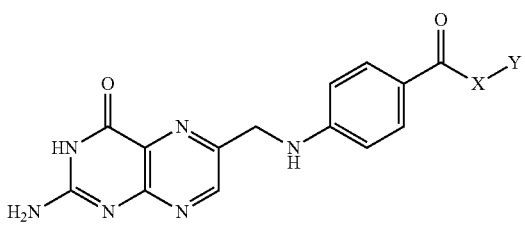

wherein:

X is an amino acid or a derivative thereof, and

Y is a dye that has a fluorescence excitation and emission spectra in the near infrared range, and said compound maintains or enhances the fluorescence of Y.

The amino acid X may be selected from the group consisting of tyrosine, cysteine, lysine, a derivative of tyrosine, a derivative of cysteine and a derivative of lysine. In a particular embodiment, the amino acid X is tyrosine, and in another embodiment, the amino acid X is a derivative of tyrosine selected from the group consisting of:

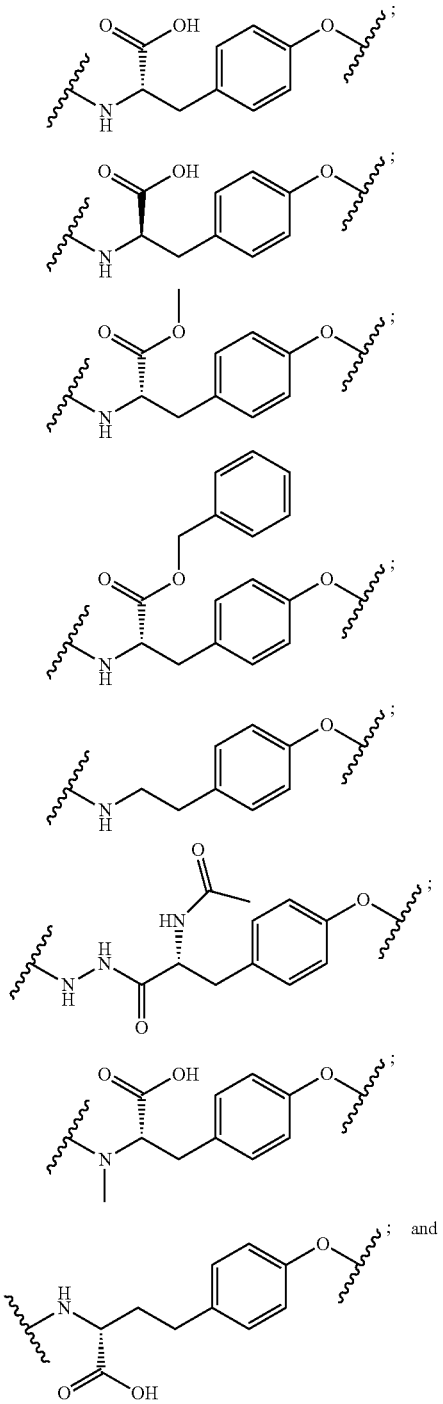

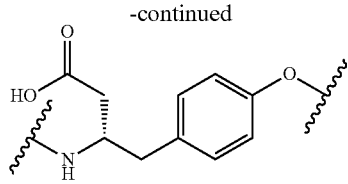

and racemic mixtures thereof.

In another embodiment, the dye Y may have the formula:

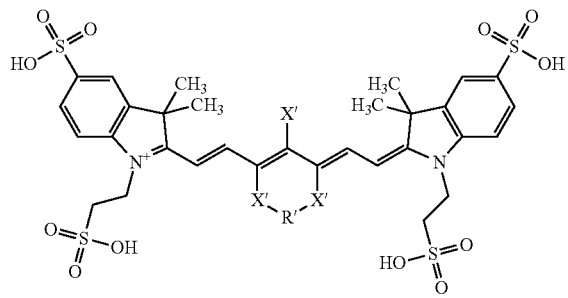

wherein:

X' is independently selected from the group consisting of O, S, N and C, and

R' is independently selected from the group consisting of CH2 and CH2CH2. In some embodiments, the dye Y is selected from the group consisting of LS288, IR800, SP054, S0121, KODAK IRD28, S2076, S0456 and derivatives thereof.

In another embodiment, the folate-imaging agent conjugate has the formula:

may have a wide variety of lengths, such as in the range from about 2 to about 100 atoms. The atoms used in forming the linker may be combined in all chemically relevant ways, such as chains of carbon atoms forming alkylene, alkenylene, and alkynylene groups, and the like; chains of carbon and oxygen atoms forming ethers, polyoxyalkylene groups, or when combined with carbonyl groups forming esters and carbonates, and the like; chains of carbon and nitrogen atoms forming amines, imines, polyamines, hydrazines, hydrazones, or when combined with carbonyl groups forming amides, ureas, semicarbazides, carbazides, and the like; chains of carbon, nitrogen, and oxygen atoms forming alkoxyamines, alkoxylamines, or when combined with carbonyl groups forming urethanes, amino acids, acyloxylamines, hydroxamic acids, and the like; and many others. In addition, it is to be understood that the atoms forming the chain in each of the foregoing illustrative embodiments may be either saturated or unsaturated, such that for example, alkanes, alkenes, alkynes, imines, and the like may be radicals that are included in the linker. In addition, it is to be understood that the atoms forming the linker may also be cyclized upon each other to form divalent cyclic structures that form the linker, including cyclo alkanes, cyclic ethers, cyclic amines, arylenes, heteroarylenes, and the like in the linker. The linker may be bivalent. In another embodiment, there is no linker in the folate-imaging agent conjugate, rather the folate ligand and the imaging agent are directly linked.

In other embodiments of the methods and uses described herein, pharmaceutically acceptable salts of the folate-imaging agent conjugates described herein are contemplated. Pharmaceutically acceptable salts of the folate-imaging agent conjugates described herein include the acid addition and base salts thereof.

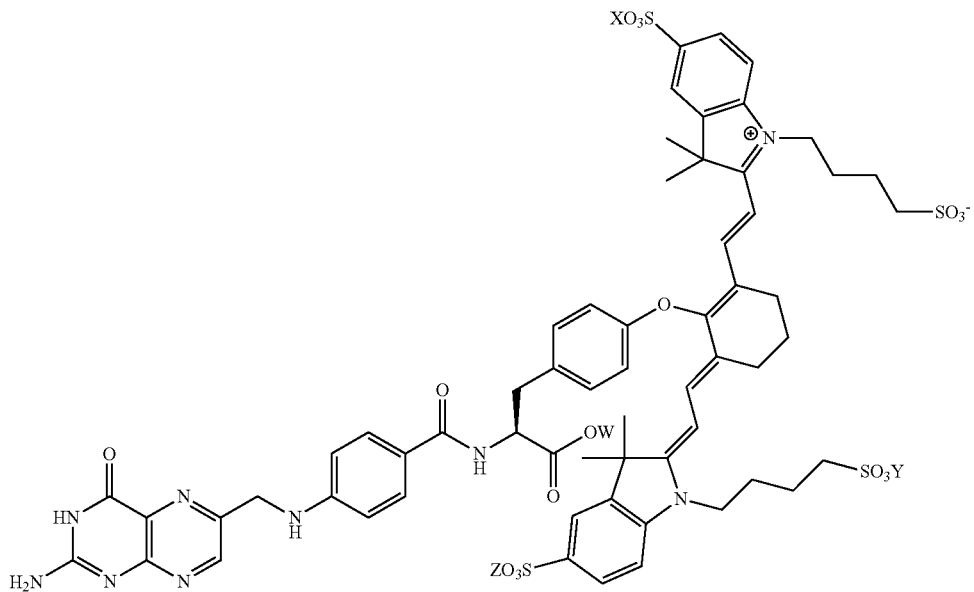

wherein W, X, Y, Z each are H, $Na^+$, $K^+$ or $NH_4^+$.

The folate ligand and the imaging agent in the folate-imaging agent conjugates, may be linked in any chemically relevant way. In one embodiment, the linker includes a chain of atoms selected from C, N, O, S, Si, and P that covalently connects the folate ligand to the imaging agent. The linker Suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts of the conjugates described herein are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemi-salts of acids and bases may also be formed, for example, hemi-sulphate and hemi-calcium salts.

In one embodiment, the folate-imaging agent conjugates described herein may be administered as a composition in association with one or more pharmaceutically acceptable carriers. The carriers can be excipients. The choice of carrier will to a large extent depend on factors such as the particular mode of administration, the effect of the carrier on solubility and stability, and the nature of the dosage form. Pharmaceutical compositions suitable for the delivery of folate-imaging agent conjugates described herein and methods for their preparation will be readily apparent to those skilled in the art. Such compositions and methods for their preparation may be found, for example, in Remington: The Science & Practice of Pharmacy, 21st Edition (Lippincott Williams & Wilkins, 2005), incorporated herein by reference.

In one illustrative aspect, a pharmaceutically acceptable carrier can include any solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions and sterile powders for the extemporaneous preparation of sterile injectable solutions or dispersions. Supplementary active compounds can also be incorporated into the compositions for use in the methods and uses described herein. Other possible carriers include, for example, water, ethanol, polyethylene glycol, propylene glycol, methylcellulose, or a suitable oil, and one or more emulsifying agents and/or suspending agents. In another embodiment, the pharmaceutically acceptable carrier is a liquid carrier and the liquid carrier can be selected from the group consisting of saline, glucose, alcohols, glycols, esters, amides, and a combination thereof. In another embodiment, the folate-imaging agent conjugate is in a sterile, pyrogen-free, aqueous solution.

In one embodiment, an aqueous suspension may contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ascorbic acid, ethyl, n-propyl, or p-hydroxybenzoate; or one or more coloring agents.

Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate. In other embodiments, isotonic agents, for example, sugars, polyalcohols such as mannitol, sorbitol, or sodium chloride can be included in the composition. In another embodiment, solubility enhancing agents may be used.

In one aspect, the folate-imaging agent conjugates can be administered parenterally. Suitable routes for such parenteral administration include intravenous, intraarterial, intraperitoneal, intrathecal, epidural, intracerebroventricular, intraurethral, intrasternal, intracranial, intramuscular and subcutaneous delivery. Suitable means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water (e.g., an aqueous solution).

The preparation of parenteral formulations under sterile conditions may readily be accomplished using standard pharmaceutical techniques well-known to those skilled in the art. In one embodiment, the folate-imaging agent conjugate can be present in the form of a reconstituted lyophilizate.

Any effective regimen for administering the folate-imaging agent conjugate can be used. For example, the folate-imaging agent conjugate can be administered as single doses, or can be divided and administered as a multiple-dose regimen. The effective amount to be administered to a patient is based on body surface area, and mass. Effective doses can range, for example, from about 1 ng/kg to about 1 mg/kg, from about 1 µg/kg to about 500 µg/kg, and from about 1 µg/kg to about 100 µg/kg. These doses are based on an average patient weight of about 70 kg, and the kg are kg of patient body weight (mass).

The folate-imaging agent conjugate can be administered in a dose of from about 1.0 ng/kg to about 1000 µg/kg, from about 10 ng/kg to about 1000 µg/kg, from about 50 ng/kg to about 1000 µg/kg, from about 100 ng/kg to about 1000 µg/kg, from about 500 ng/kg to about 1000 µg/kg, from about 1 ng/kg to about 500 µg/kg, from about 1 ng/kg to about 100 µg/kg, from about 1 µg/kg to about 50 µg/kg, from about 1 µg/kg to about 10 µg/kg, from about 5 µg/kg to about 500 µg/kg, from about 10 µg/kg to about 100 µg/kg, from about 20 µg/kg to about 200 µg/kg, from about 10 µg/kg to about 500 µg/kg, or from about 50 µg/kg to about 500 µg/kg. The total dose may be administered in single or divided doses and may, at the physician's discretion, fall outside of the typical range given herein. These dosages are based on an average patient weight of about 70 kg and the "kg" are kilograms of patient body weight.

In another embodiment, the folate-imaging agent conjugate can be administered in a dose of from about 1 µg/m$^2$ to about 500 mg/m$^2$, from about 1 µg/m$^2$ to about 300 mg/m$^2$, or from about 100 µg/m² to about 200 mg/m². In other embodiments, the folate-imaging agent conjugate can be administered in a dose of from about 1 mg/m² to about 500 mg/m², from about 1 mg/m² to about 300 mg/m², from about 1 mg/m² to about 200 mg/m², from about 1 mg/m² to about 100 mg/m², from about 1 mg/m² to about 50 mg/m², or from about 1 mg/m² to about 600 mg/m². The total dose may be administered in single or divided doses and may, at the physician's discretion, fall outside of the typical range given herein. These dosages are based on m² of body surface area.

The folate-imaging agent conjugates described herein may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The folate-imaging agent conjugates described herein may be capable of existing as geometric isomers. Accordingly, it is to be understood that the present invention includes pure geometric isomers or mixtures of geometric isomers.

It is appreciated that the folate-imaging agent conjugates described herein may exist in unsolvated forms as well as solvated forms, including hydrated forms. In general, the solvated forms are equivalent to unsolvated forms and are encompassed within the scope of the present invention. The folate-imaging agent conjugates described herein may exist in multiple crystalline or amorphous forms before reconstitution and administration to the patient. In another embodiment, the folate-imaging agent conjugate is provided in a sterile container or package.

In another embodiment, the folate-imaging agent conjugates having a radioactive imaging agent, such as $^{99m}$Tc-EC20, have a radiochemical purity of at least about 90%, or about 95%, or about 96%, or about 97%, or about 98%, or about 99%, or about 99.5%. As used herein, purity determinations may be based on weight percentage, mole percentage, and the like.

In addition, purity determinations for the folate-imaging agent conjugates may be based on the absence or substantial absence of certain predetermined components, such as, but not limited to, folic acid, oxidation products, disulfide components not containing a folate ligand, and the like. In those instances, purity measurements, including weight percentage and mole percentage measurements, are related to the components of the solution exclusive of the solvent. The folate-imaging agent conjugates may have a purity of at least about 90%, or about 95%, or about 96%, or about 97%, or about 98%, or about 99%, or about 99.5%.

The purity of the folate-imaging agent conjugates may be measured using any conventional technique, including various chromatography or spectroscopic techniques, such as high pressure or high performance liquid chromatography (HPLC), nuclear magnetic resonance spectroscopy, TLC, UV absorbance spectroscopy, fluorescence spectroscopy, and the like.

Any type of medical imaging procedure known in the art can be used to detect the signal produced in the patient by the folate-imaging agent conjugate. Examples of medical imaging procedures include, but are not limited to, the use of radioactive imaging agents in imaging procedures, the use of fluorescent imaging agents or other types of dyes in medical imaging, positron emission tomography (PET), magnetic resonance imaging, computed tomography, scintigraphic imaging, SPECT, SPECT/CT, planar imaging, optical imaging, ultrasound, and the like. The images can be quantitated by any method known in the art for quantitation of medical images, including but not limited to, densitometry, quantitative PET imaging, and the like.

In one embodiment specific for $^{99m}$Tc-EC20, for the imaging procedure the patient is injected with 0.5 mg of unlabeled folic acid, followed within 1 to 3 minutes by a 1 to 2 mL injection of 0.1 mg of EC20 labeled with 20 to 25 mCi of $^{99m}$Tc and imaging is performed 1 to 2 hours later. In this embodiment, the imaging methods can be selected from the group consisting of planar, SPECT, and SPECT/CT imaging.

In any embodiment described herein, unlabeled folic acid can be administered to the patient, and, in such embodiments, the unlabeled folic acid can be administered to the patient prior to administration of the folate-imaging agent conjugate, or within one hour of administration of the folate-imaging agent conjugate.

In another embodiment, the methods and uses described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention.

Example 1

Animal Models

All animal procedures were approved by the Purdue Animal Care and Use Committee in accordance with guidelines from the National Institutes of Health. Mice were maintained in a temperature and humidity controlled room on a 12-h dark-light cycle with food and water available ad libitum.

Example 2

Collagen-Induced Arthritis

Collagen-induced arthritis (CIA) was initiated using established methods on 6-7 week old female DBA/1 mice (Jackson Laboratories) maintained on folate-deficient diet (Harlan-Teklad). Briefly, mice were immunized at the base of the tail with 100 µg bovine type II collagen emulsified in complete Freund's adjuvant (Chondrex, Inc., Redmond, Wash., USA). Mice were then boosted 21 days later with a similar injection of 100 µg bovine type II collagen emulsified in incomplete Freund's adjuvant. After four days, onset of arthritis was synchronized in all mice with an intraperitoneal injection of 25 µg lipopolysaccharide (LPS) dissolved in saline. Three days later mice were distributed equally across control and treatment groups (n=5). Healthy mice and disease control mice received daily intraperitoneal injections of 100 µL saline. Diseased mice to be tested for response to therapy received intraperitoneal injections of methotrexate (9 mg/kg, every 3 days), dexamethasone (0.5 mg/kg, daily), etanercept (300 µg, daily), or abatacept (300 µg, daily), or an oral gavage with naproxen (50 mg/kg, 5× week). Arthritis scores were assessed every other day by researchers blinded to the various treatment groups, using the following scoring system: 0=normal; 1=mild, but definite redness and swelling of the ankle or wrist, or apparent redness and swelling limited to individual digits, regardless of the number of affected digits; 2=moderate redness and swelling of ankle or wrist; 3=severe redness and swelling of the entire paw including digits; 4=maximally inflamed limb with involvement of multiple joints. A total score for each mouse was calculated by summing the scores for each of the four paws, allowing a maximum possible score of 16 per animal. Paw thickness was measured with calipers every other day starting on the first day of treatment. On day 3 of treatment, mice were anesthetized with isoflurane and imaged with $^{99m}$Tc-EC20 as described below. Mice were again imaged and then euthanized by $CO_2$ asphyxiation on day 11 of treatment.

Example 3

Ulcerative Colitis

Ulcerative colitis was induced as previously described in S. Wirtz, C. Neufert, B. Weigmann, M. F. Neurath, Chemically induced mouse models of intestinal inflammation. *Nat Protoc.* 2, 541-546 (2007), incorporated herein by reference. Seven week old Balb/c mice (Harlan Laboratories) maintained on a folate-deficient diet were administered 5% dextran sodium sulfate (DSS) in their drinking water. Mice were divided into treatment groups (n=10 per group). Healthy mice and disease control mice received 100 µL saline daily by oral gavage. Diseased mice were treated daily with cimetidine (100 mg/kg) or sulphasalazine (150 mg/kg) by oral gavage. Healthy mice were maintained on normal water and similarly treated with saline. Disease symptoms were assessed daily and quantitated by adding the scores from each of the following tests: Weight loss: 0=no weight loss, 1=1-5% weight loss, 2=6-10% weight loss, 3=11-15% weight loss, 4=>15% weight loss; Stool appearance: 0=normal, 1=loose feces, 2=diarrhea; Hematochezia (blood in stool): 0=no blood, 1=positive via guaiac paper, 2=visually bloody; Overall appearance: 0=normal, 1=ruffled fur/altered gait, 2=lethargic, moribund. On day 4 of therapy, half of each treatment group (n=5) received an intraperitoneal injection of $^{99m}$Tc-EC20. After 4 hours, the injected mice were euthanized and the bladder and kidneys were removed to reduce background radiation associated with $^{99m}$Tc-EC20 undergoing excretion. Mice were then imaged to assess uptake of $^{99m}$Tc-EC20 in the colon, and the colons were removed and measured with calipers to evaluate colon shortening as a measure of disease severity. On day 8, the remaining mice were injected with $^{99m}$Tc-EC20 and analyzed similarly.

Example 4

Atherosclerosis

Five week old male ApoE-/- mice were purchased from Jackson Laboratories and placed on an adjusted calorie diet (42% from fat, Harlan Laboratories). Healthy control mice (C57BL/6) were similarly maintained on normal chow. Mice were divided into therapy groups (n=5). Healthy mice and disease control mice received 100 µL saline daily by oral gavage. Diseased mice were treated daily with valsartan (1 mg/kg), or fluvastatin (3 mg/kg) by oral gavage. After three weeks of treatment, mice were imaged with 300 µCi $^{99m}$Tc-EC20. Mice were again imaged with $^{99m}$Tc-EC20 after 12 weeks of therapy and then euthanized by $CO_2$ asphyxiation. Aortas were dissected and H&E and oil red O staining was performed.

Example 5

Pulmonary Fibrosis

Pulmonary fibrosis was induced in mice as previously described in B. B. Moore, C. M. Hogaboam, Murine models of pulmonary fibrosis. *Am J Physiol Lung Cell Mol Physiol.* 294, L152-160 (2008), incorporated herein by reference. Briefly, 6 week old female C57BL/6 mice (Harlan Laboratories) maintained on a folate-deficient diet were anaesthetized with isoflurane, and 50 µL of bleomycin (2 U/kg body weight) dissolved in saline was intratracheally instilled into each mouse. Healthy control mice were similarly intratracheally instilled with 50 µL saline. Mice were then separated into treatment groups (n=5). Healthy mice and disease control mice received daily intraperitoneal injections of 100 µL saline. Diseased mice were injected every day intraperitoneally with dexamethasone (0.5 mg/kg) or etanercept (300 µg). Mice were imaged with $^{99m}$Tc-EC20 after 6 days of treatment and again after 15 days of treatment. Mice were then euthanized by $CO_2$ asphyxiation and bronchoalveolar lavage fluid was collected and cells were counted using a Beckman Coulter Z™ Series COULTER COUNTER® Cell and Particle Counter. The left lung was fixed in formalin and submitted to the Purdue Histology & Phenotyping Laboratory for H&E staining and the right lung was used for analysis of hydroxyproline content using a hydroxyproline assay kit from Sigma-Aldrich (St. Louis, Mo.).

Example 6

Preparation of $^{99m}$Tc-EC20 and Imaging of Sites of Macrophage Accumulation in Inflamed Mice $^{99m}$Tc-EC20 was prepared as previously described in C. P. Leamon, M. A. Parker, I. R. Vlahov, L. Xu, J. A. Reddy, M. Vetzel, N. Douglas, Synthesis and Biological Evaluation of EC20: A New Folate-Derived, $^{99m}$Tc-Based Radiopharmaceutical. *Bioconjugate Chem.* 13, 1200-1210 (2002), incorporated herein by reference. A preparation method for $^{99m}$Tc-EC20 is also described in U.S. Pat. No. 7,128,893, incorporated herein by reference. Briefly, 1 mL of 15 mCi/mL sodium pertechnetate (Cardinal Health) was added to 0.1 mg of EC20 (a gift from Endocyte, Inc.) and heated at 100° C. for 18 min. After diluting with saline, 100 µL $^{99m}$Tc-EC20 (150 µCi (~75 nmol of EC20 per kilogram for CIA, ulcerative colitis and pulmonary fibrosis mice) or 300 µCi (~150 nmol of EC20 per kilogram for atherosclerosis)) was injected intraperitoneally into the desired mice, and unbound $^{99m}$Tc-EC20 was allowed to clear from tissues for 4 h. Mice were then either anesthetized with 3% isoflurane (CIA, atherosclerosis, and pulmonary fibrosis mice) or euthanized (ulcerative colitis mice) prior to image acquisition using a Kodak Image Station operated with Kodak molecular imaging software (version 4.5; Carestream Molecular Imaging). Radioimages were acquired for 2 minutes using a radioisotopic phosphor screen, no illumination source, 4×4 binning, focal plane=5, FOV=160, and f-stop=0. White light images were acquired for 0.175 seconds with white light transillumination source, no binning, focal plane=5, FOV=160, and f-stop=11.

Example 7

Figure 1B:
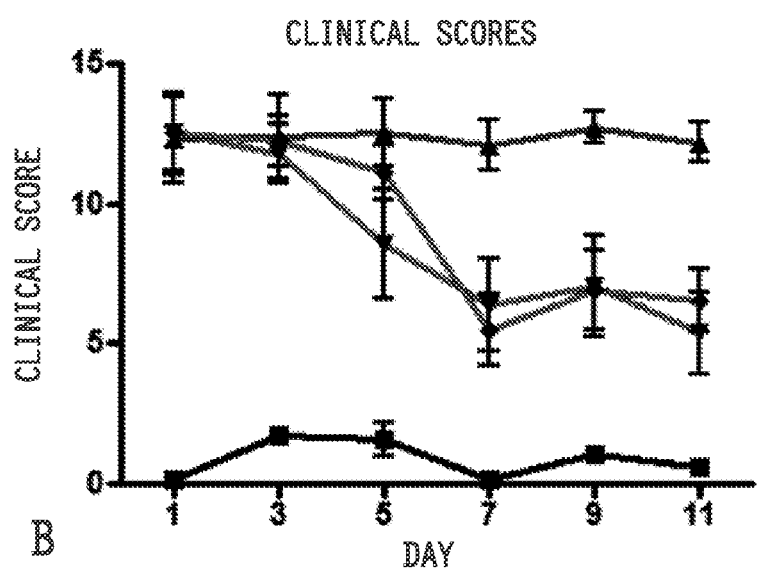
Figure 1C:
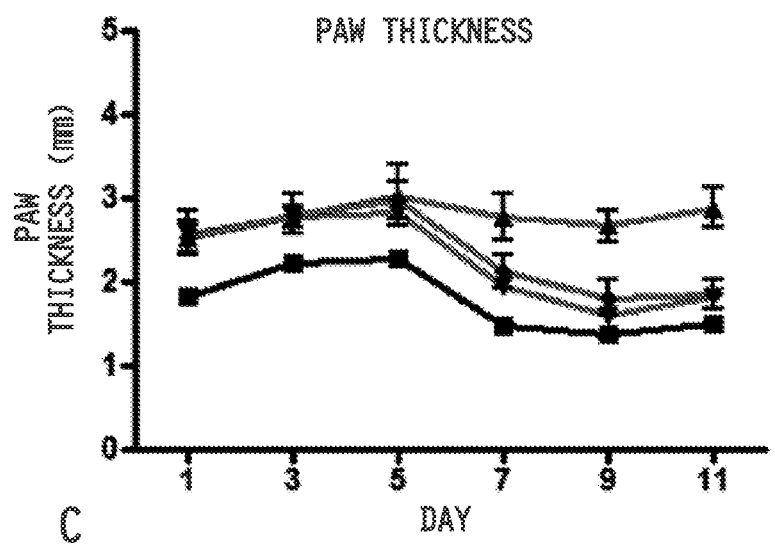
Figure 7:
FIG. 7. Analysis of $^{99m}$Tc-EC20 accumulation in CIA mice treated with methotrexate or dexamethasone. A: Radioimage of mice injected with $^{99m}$Tc-EC20 11 days after initiation of treatment with methotrexate (left), saline (middle) or dexamethasone (right).

Imaging with $^{99m}$Tc-EC20 Predicts Response to Treatment in a Murine Model of Rheumatoid Arthritis Mice were induced to develop collagen-induced arthritis (CIA, a well-established model of rheumatoid arthritis) and subjected 28 days later to treatment with methotrexate, dexamethasone or saline (disease control). Three days after initiation of therapy, the mice were injected with 150 µCi of $^{99m}$Tc-EC20 and subjected to their first planned radioimage analysis. As seen in FIG. 1A, mice induced to develop CIA but not treated with any anti-inflammatory drug exhibited the accumulation of $^{99m}$Tc-EC20 in their inflamed appendages, confirming involvement of folate receptor-positive activated macrophages in the autoimmune disease. Inflamed mice injected with either methotrexate or dexamethasone displayed markedly less $^{99m}$Tc-EC20 in the affected appendages, despite revealing no reduction in disease symptoms (arthritis score, paw swelling) at this early time point (FIGS. 1B & C). Moreover, after 11 days of continuous therapy, when the treated mice had finally responded to their respective therapies and joint inflammation had substantially resolved (FIGS. 1B & C), images of the same mice (FIG. 7) confirmed the significantly reduced uptake of $^{99m}$Tc-EC20 in the treated mice relative to disease control mice. These data show that uptake of $^{99m}$Tc-EC20 in the inflamed joints of CIA mice soon after initiation of therapy can be used to predict an eventual response of the mice to both methotrexate and dexamethasone.

Figure 2A:
FIG. 2. Analysis of $^{99m}$Tc-EC20 uptake in CIA mice treated with etanercept or abatacept. A: Radioimages of mice injected with $^{99m}$Tc-EC20 three days after initiation of treatment with etanercept (left), saline (middle) or abatacept (right). B and C: Arthritis scores and paw thickness measurements of mice in each of the following treatment groups: disease control (up triangle), etanercept (down triangle), abatacept (diamond), and healthy control (square).
Figure 2B:
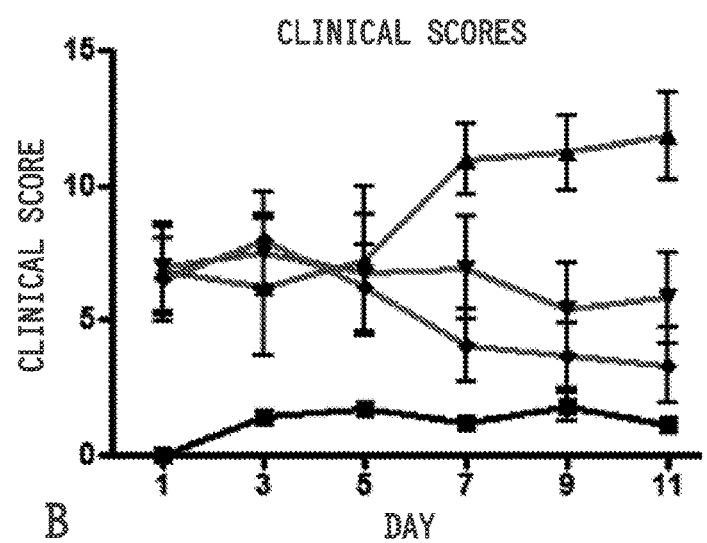
Figure 2C:
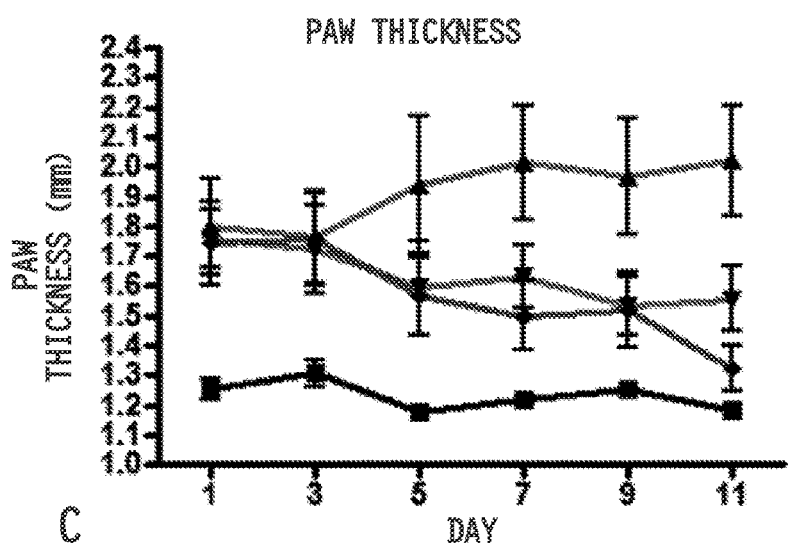
Figure 8:
FIG. 8. Analysis of $^{99m}$Tc-EC20 uptake in CIA mice treated with etanercept or abatacept. A: Radioimages of mice injected with $^{99m}$Tc-EC20 11 days after initiation of treatment with etanercept (left), saline (middle) or abatacept (right).

To explore whether the ability of $^{99m}$Tc-EC20 to predict response to methotrexate and dexamethasone might also extend to biologic therapies, the above study was repeated, only etanercept and abatacept were substituted for methotrexate and dexamethasone. As seen in FIG. 2A, mice treated with the aforementioned biologics also showed significantly less uptake of $^{99m}$Tc-EC20 on day 3 of therapy than mice in the disease control group, even though no significant difference in clinical symptoms was again measurable at this early time point (FIGS. 2B & C). Moreover, analysis of disease symptoms on day 11 of therapy revealed that the treated mice did indeed eventually respond to etanercept and abatacept with significantly reduced inflammation. Radioimages of the mice on day 11 (FIG. 8) demonstrated a similar $^{99m}$Tc-EC20 biodistribution to the radioimages on day 3. These data show that images acquired with $^{99m}$Tc-EC20 early in the course of therapy can also predict the response of CIA mice to a biologic therapy.

Figure 3A:
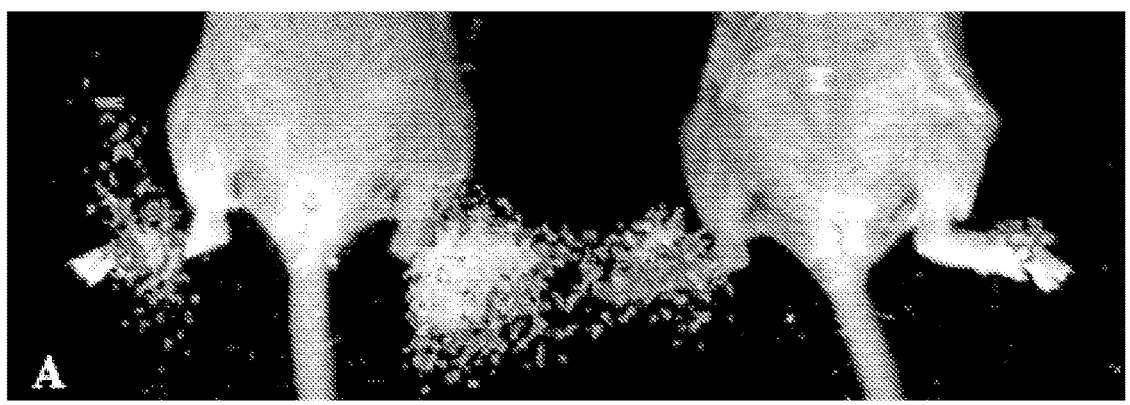
FIG. 3. Analysis of $^{99m}$Tc-EC20 accumulation in CIA mice treated with naproxen. A: Radioimage of mice injected with $^{99m}$Tc-EC20 three days after initiation of treatment with naproxen (left), or saline (right). B and C: Arthritis scores and paw thickness measurements of mice for the following treatment groups: disease control (up triangle), naproxen (down triangle), and healthy control (square).
Figure 3B:
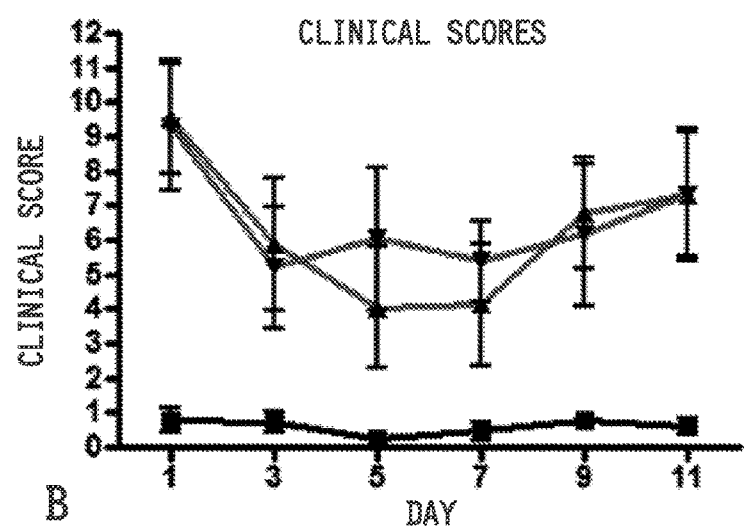
Figure 3C:
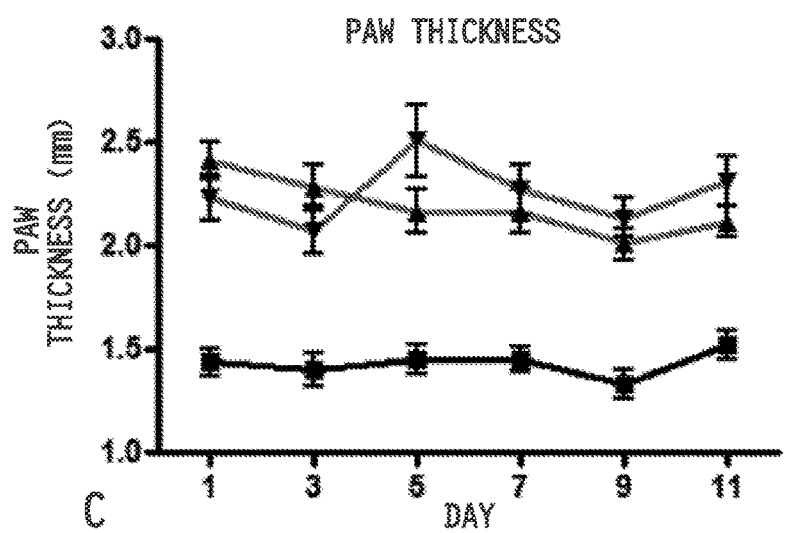

In order to evaluate whether imaging with $^{99m}$Tc-EC20 might also be useful for identifying patients that will eventually fail to respond to a particular therapy, CIA mice were treated with naproxen, an anti-inflammatory drug (NSAID) used to treat rheumatoid arthritis in humans, but previously found to have little efficacy in the CIA model of arthritis in mice. Importantly, $^{99m}$Tc-EC20 images on day 3 of therapy revealed no significant difference in uptake between naproxen-treated and disease control groups, showing that mice unable to respond to therapy also fail to show a decrease in $^{99m}$Tc-EC20 accumulation (FIG. 3A). Following 11 days of naproxen therapy, there was still no significant difference in arthritis scores or paw thickness between treated and disease control mice (FIGS. 3B & C). These data show that $^{99m}$Tc-EC20 images acquired before changes in disease symptoms occur can accurately identify mice that will eventually fail to respond to therapy.

Example 8

Figure 4A:
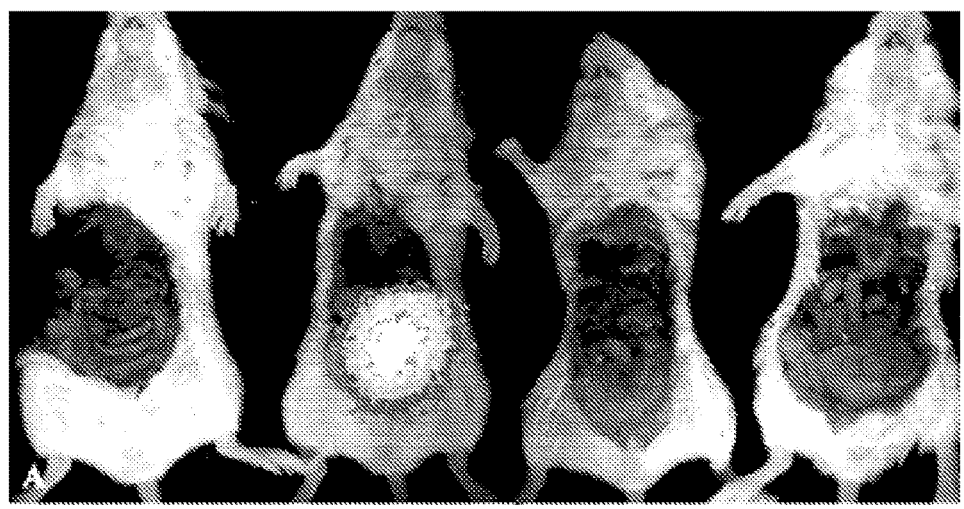
FIG. 4. Analysis of $^{99m}$Tc-EC20 accumulation in mice with ulcerative colitis treated with cimetidine or sulphasalazine. A: Radioimages of mice injected with $^{99m}$Tc-EC20 four days after initiation of treatment. From left to right, healthy control, treatment with saline, treatment with cimetidine and treatment with sulphasalazine. B: Clinical colitis scores of mice were recorded daily for each treatment group: disease control (up triangle), cimetidine (diamond), sulphasalazine (down triangle), and healthy control (square). C. Colons were removed after 4 days of treatment (left columns) and 8 days of treatment (right columns), and the lengths were measured using calipers.
Figure 4B:
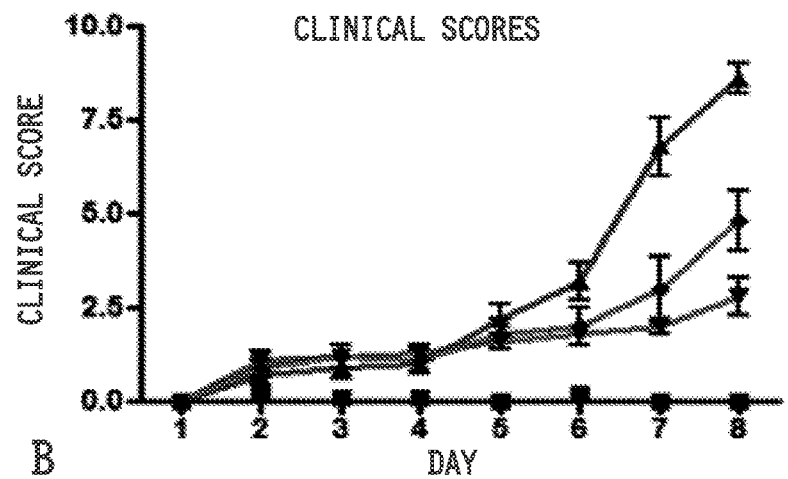
Figure 4C:
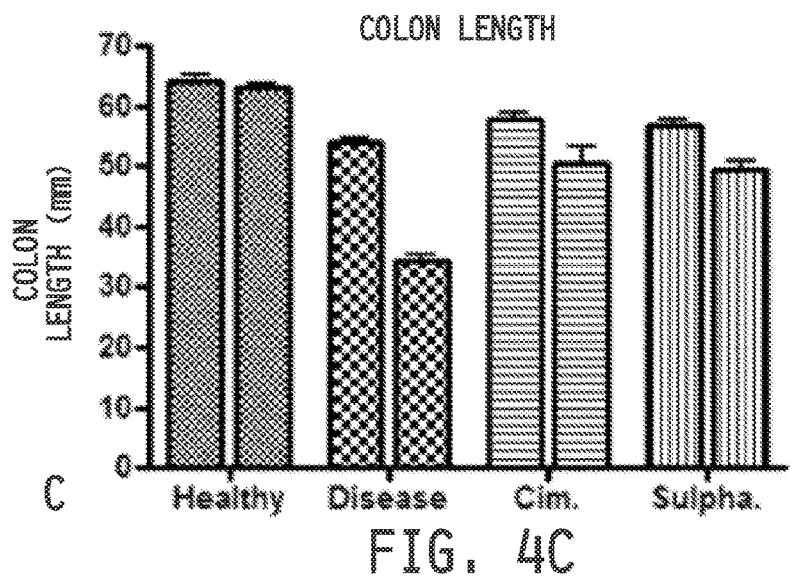
Figure 9:
FIG. 9. Analysis of $^{99m}$Tc-EC20 accumulation in mice with ulcerative colitis treated with cimetidine or sulphasalazine. A: Radioimages of mice injected with $^{99m}$Tc-EC20 8 days after initiation of treatment. From left to right, healthy control, treatment with saline, treatment with cimetidine and treatment with sulphasalazine.

Imaging with $^{99m}$Tc-EC20 Predicts Response to Therapy in a Murine Model of Ulcerative Colitis Mice (n=10/group) were administered 5% dextran sulfate sodium (DSS) in water to induce ulcerative colitis and then treated daily with cimetidine, sulphasalazine or saline (disease control). Then on day 4, half of the mice (n=5/group) were injected with 150 μCi $^{99m}$Tc-EC20 and euthanized in preparation for subsequent imaging of their colons. As seen in FIG. 4A, cimetidine- and sulphasalazine-treated mice showed significantly less $^{99m}$Tc-EC20 uptake than saline-treated mice, even though there was no significant difference in their clinical scores or colon lengths at this early time point (FIGS. 4B & C). More importantly, after 8 days of continuous therapy, treated mice were found to have significantly lower clinical scores and reduced colon shortening when compared to disease control mice (FIGS. 4B & C). And as before, radioimages remained essentially unchanged from those collected at the earlier time point (FIG. 9). Taken together, these data show that imaging with $^{99m}$Tc-EC20 shortly after the initiation of therapy can also predict response to treatment in a murine model of ulcerative colitis.

Example 9

Figure 5A:
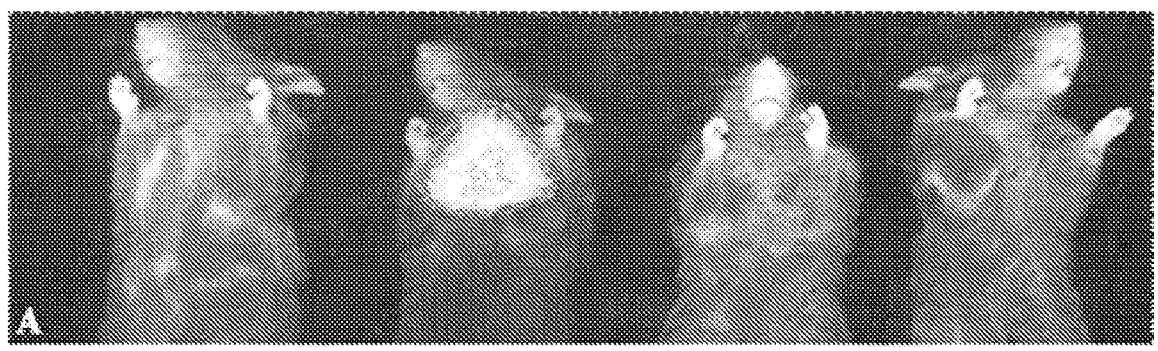
FIG. 5. Analysis of $^{99m}$Tc-EC20 accumulation in the aortic sinus of ApoE−/− mice treated with valsartan or fluvastatin. A: Radioimages of mice injected with $^{99m}$Tc-EC20 3 weeks after initiation of treatment. From left to right: healthy (C57BL/6) control, ApoE−/− mouse treated with saline, ApoE−/− mouse treated with valsartan, ApoE−/− mouse treated with fluvastatin. B. H&E staining of arterial walls from the aortic sinus of each of the mice imaged directly overhead. RBCs=red blood cells.
Figure 5B:
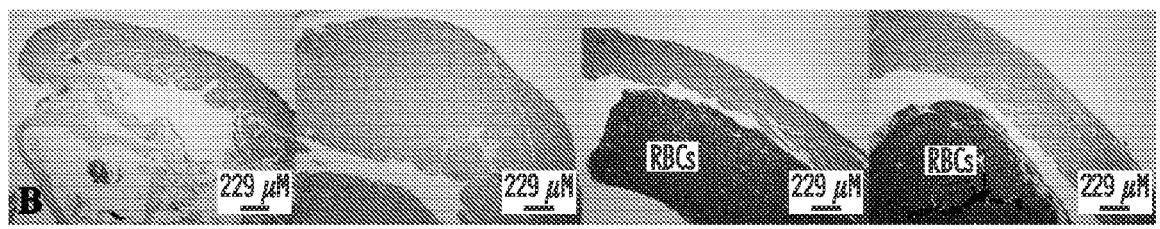
Figure 10:
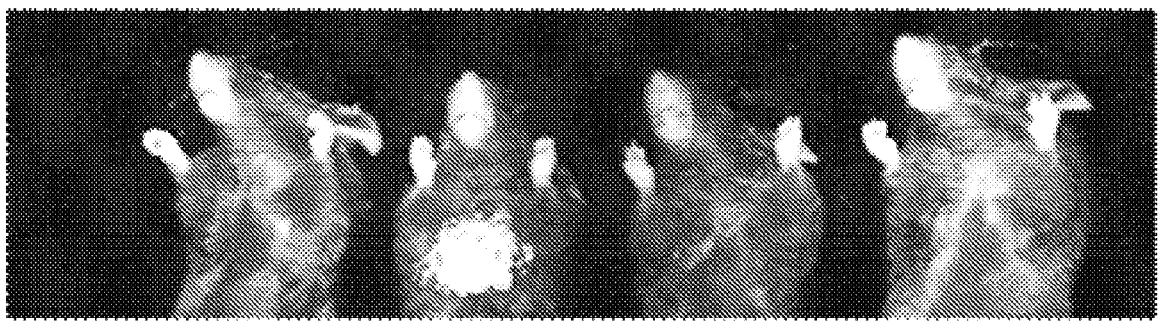
FIG. 10. Analysis of $^{99m}$Tc-EC20 accumulation in the aortic sinus of ApoE−/− mice treated with valsartan or fluvastatin. A: Radioimages of mice injected with $^{99m}$Tc-EC20 3 weeks after initiation of treatment. From left to right: healthy (C57BL/6) mouse, ApoE−/− mouse treated with saline, ApoE−/− mouse treated with valsartan, ApoE−/− mouse treated with fluvastatin.

Imaging with $^{99m}$Tc-EC20 Predicts Response to Therapy in a Murine Model of Atherosclerosis The ability to predict response to therapy might be most useful when applied to treatment of inflammatory/autoimmune diseases that are either intrinsically difficult to monitor or slow to respond to therapeutic intervention. Because atherosclerosis suffers from both disadvantages due to its inaccessible location and slow rate of progression, $^{99m}$Tc-EC20 was analyzed to determine if it might be effective in predicting response to therapy in a common murine model of heart disease. For this purpose, five week old ApoE−/− mice were fed a high fat diet and treated daily with valsartan or fluvastatin, both of which have been shown to reduce plaque formation in murine models of atherosclerosis. After 3 weeks of daily treatment, when no morphological symptoms of heart disease could be detected, mice were anesthetized and imaged with $^{99m}$Tc-EC20. As seen in FIG. 5A, ApoE−/− mice treated with either valsartan or fluvastatin displayed significantly less $^{99m}$Tc-EC20 uptake in their chest cavities than mice treated with saline. Moreover, after 12 weeks of daily therapy, the valsartan- and fluvastatin-treated groups showed significantly reduced aortic wall thickening than their saline-treated counterparts (FIG. 5B). Radioimages on week 12 revealed a similar uptake pattern to images obtained on week 3 (FIG. 10). These data show that imaging with $^{99m}$Tc-EC20 shortly after the initiation of therapy can also predict response to treatment in a murine model of atherosclerosis.

Example 10

Figure 6A:
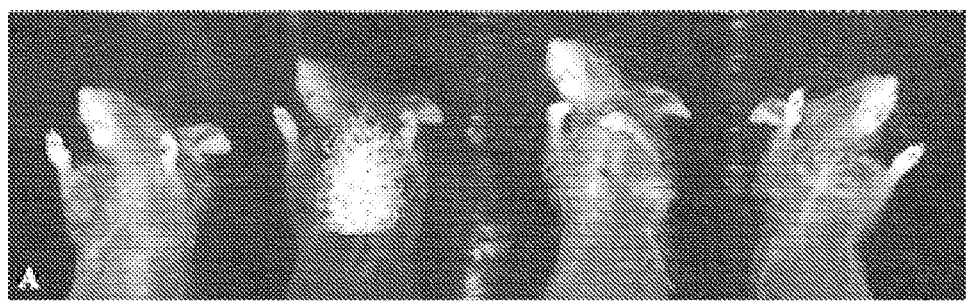
FIG. 6. Analysis of $^{99m}$Tc-EC20 accumulation in mice with pulmonary fibrosis treated with etanercept or dexamethasone. A: Radioimages of mice injected with $^{99m}$Tc-EC20 after six days of treatment. From left to right, healthy control, treatment with saline, treatment with dexamethasone and treatment with etanercept. B: Lung hydroxyproline content of lungs analyzed after 15 days of treatment. C: Total bronchoalveolar lavage fluid cell counts after 15 days of treatment. D. H&E staining of lung tissue, from left to right: healthy control, treatment with saline, treatment with dexamethasone and treatment with etanercept.
Figure 6B:
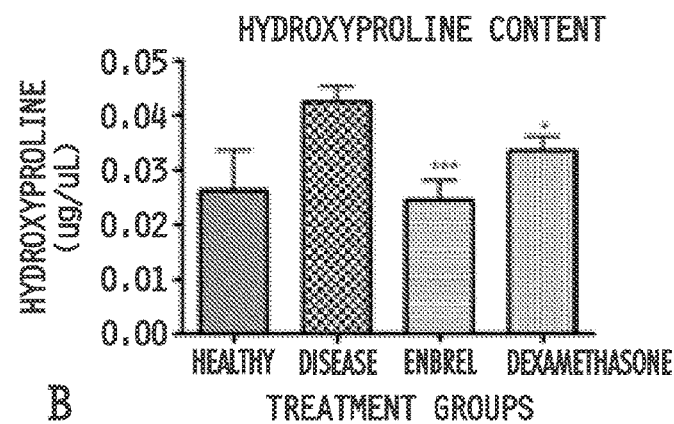
Figure 6C:
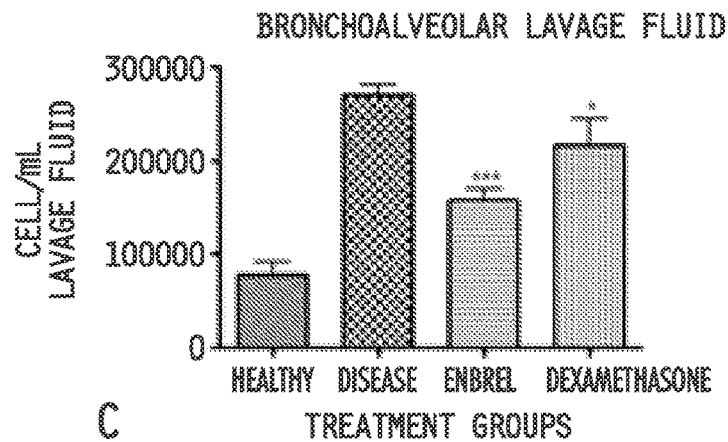
Figure 6D:
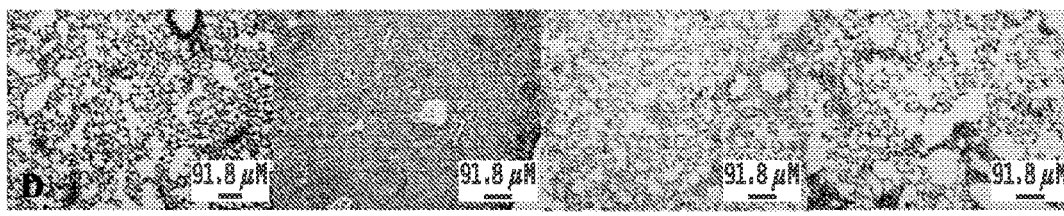
Figure 11:
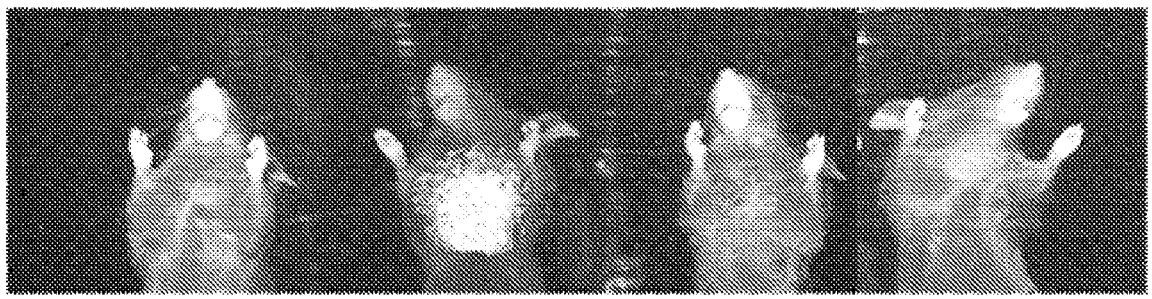
FIG. 11. Analysis of $^{99m}$Tc-EC20 accumulation in mice with pulmonary fibrosis treated with etanercept or dexamethasone. A: Radioimages of mice injected with $^{99m}$Tc-EC20 after 15 days of treatment. From left to right, healthy control mouse, mouse treated with saline, mouse treated with dexamethasone, and mouse treated with etanercept.

Imaging with $^{99m}$Tc-EC20 Predicts Response to Treatment in a Murine Model of Pulmonary Fibrosis Because the folate receptor-positive activated macrophages that accumulate in murine models of rheumatoid arthritis and ulcerative colitis consist predominantly of classically activated (M1) macrophages, $^{99m}$Tc-EC20 imaging was analyzed to determine if it might also prove useful in predicting response to therapy in an autoimmune disease mediated primarily by alternatively activated (M2) macrophages. Since pulmonary fibrosis is thought to be primarily driven by M2 macrophages, C57BL/6 mice were induced to develop an acute form of lung fibrosis by intratracheal instillation of bleomycin. Immediately following disease induction, mice were treated daily with intraperitoneal injections of dexamethasone, etanercept, or saline, and then imaged with $^{99m}$Tc-EC20 six days later. As shown in FIG. 6A, dexamethasone- and etanercept-treated mice displayed decreased accumulation of $^{99m}$Tc-EC20 compared to their saline-treated disease controls. Moreover, on day 15 of treatment, when the mice were again imaged with $^{99m}$Tc-EC20 (FIG. 11), dexamethasone- and etanercept-treated mice exhibited decreased total cell counts in their broncho-alveolar lavage fluids, as well as reduced hydroxyproline contents in their resected lung tissues compared to saline-treated controls (FIGS. 6B & C). H&E analysis of the lungs confirmed the reduced fibrosis in mice treated with dexamethasone or etanercept (FIG. 6D). Taken together, these results indicate that $^{99m}$TC-EC20 imaging can successfully predict response to treatment in an inflammatory disease mediated by alternatively activated macrophages, such as for pulmonary fibrosis.

Example 11

Figure 12:
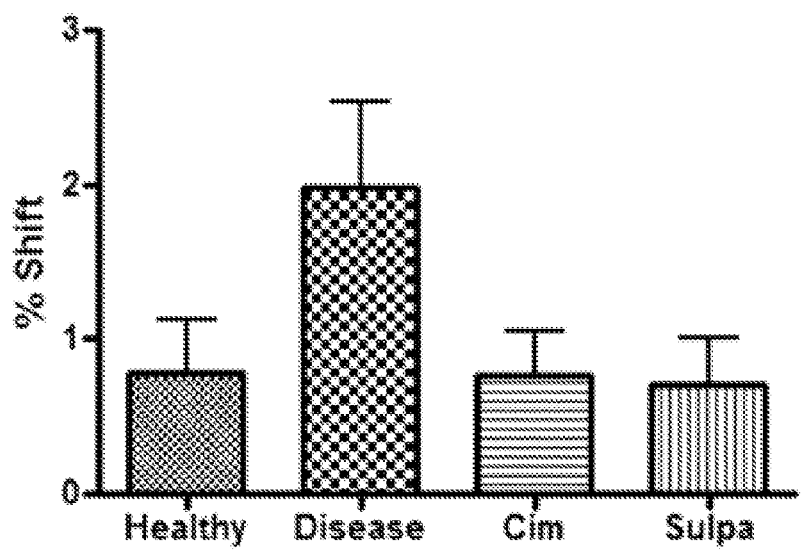
FIG. 12. Flow cytometric analysis of macrophage accumulation in mice with ulcerative colitis treated with cimetidine or sulphasalazine.
Figure 13:
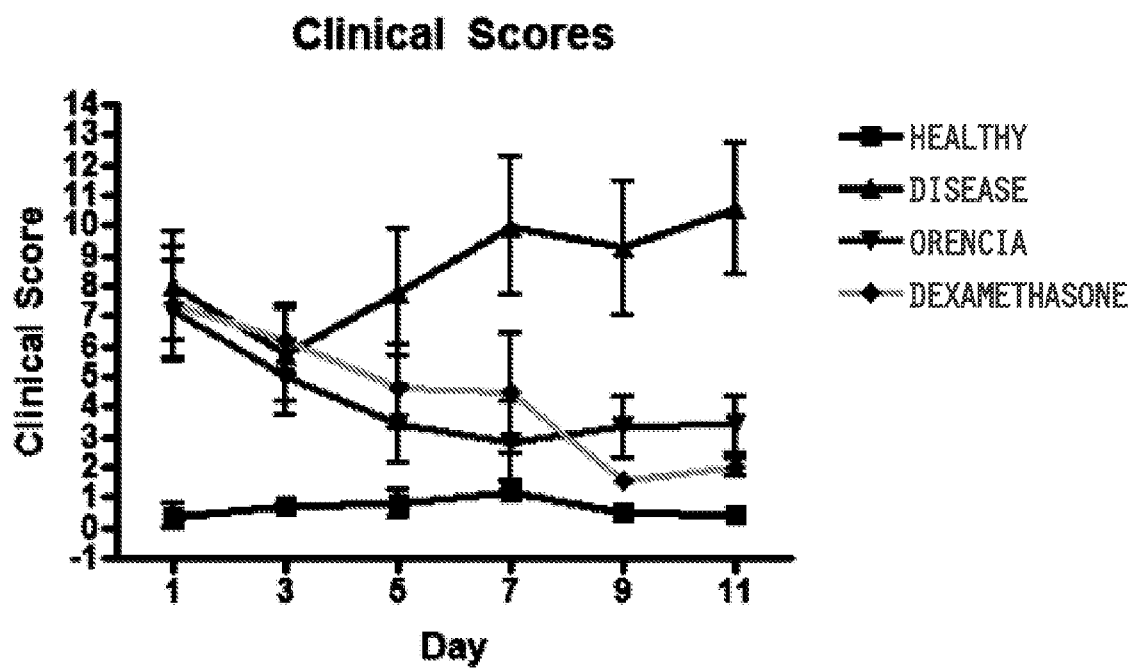
FIG. 13. Analysis of OTL-38 accumulation in CIA mice treated with orencia or dexamethasone. Clinical scores are shown for mice in each of the following treatment groups: healthy control, disease control, orencia, and dexamethasone.
Figure 14:
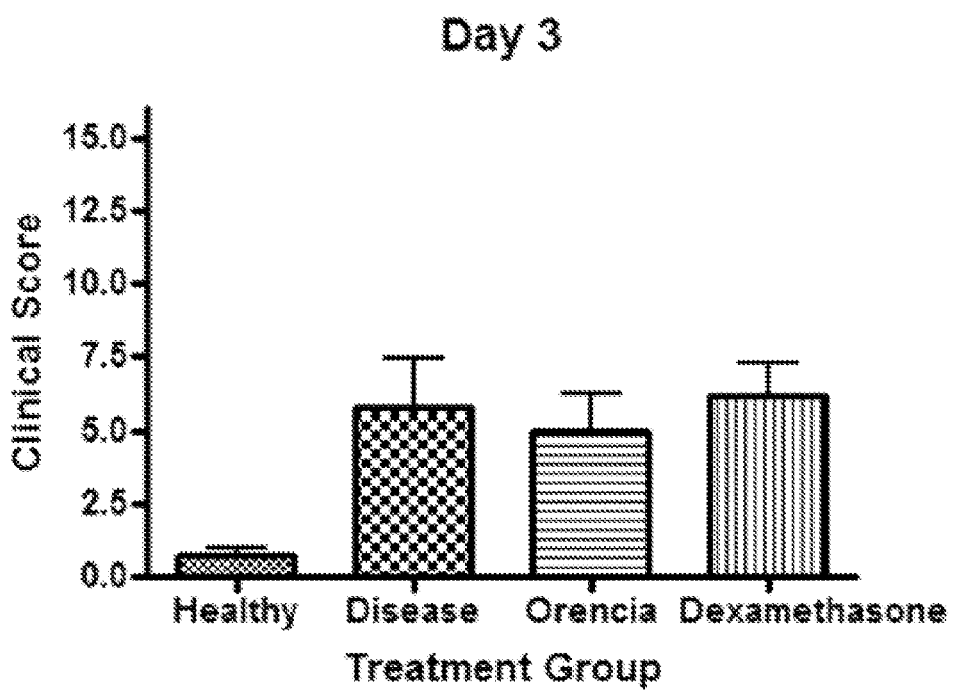
FIG. 14. Analysis of OTL-38 accumulation (Day 3) in CIA mice treated with orencia or dexamethasone. Clinical scores are shown for mice in each of the following treatment groups: healthy control, disease control, orencia, and dexamethasone.
Figure 15:
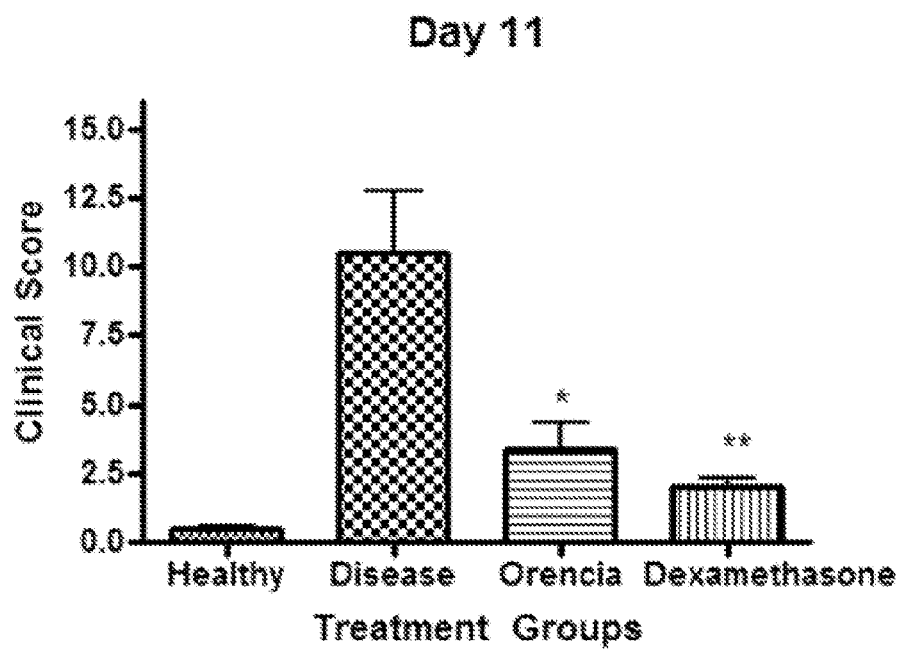
FIG. 15. Analysis of OTL-38 accumulation (Day 11) in CIA mice treated with orencia or dexamethasone. Clinical scores are shown for mice in each of the following treatment groups: healthy control, disease control, orencia, and dexamethasone.
Figure 16:
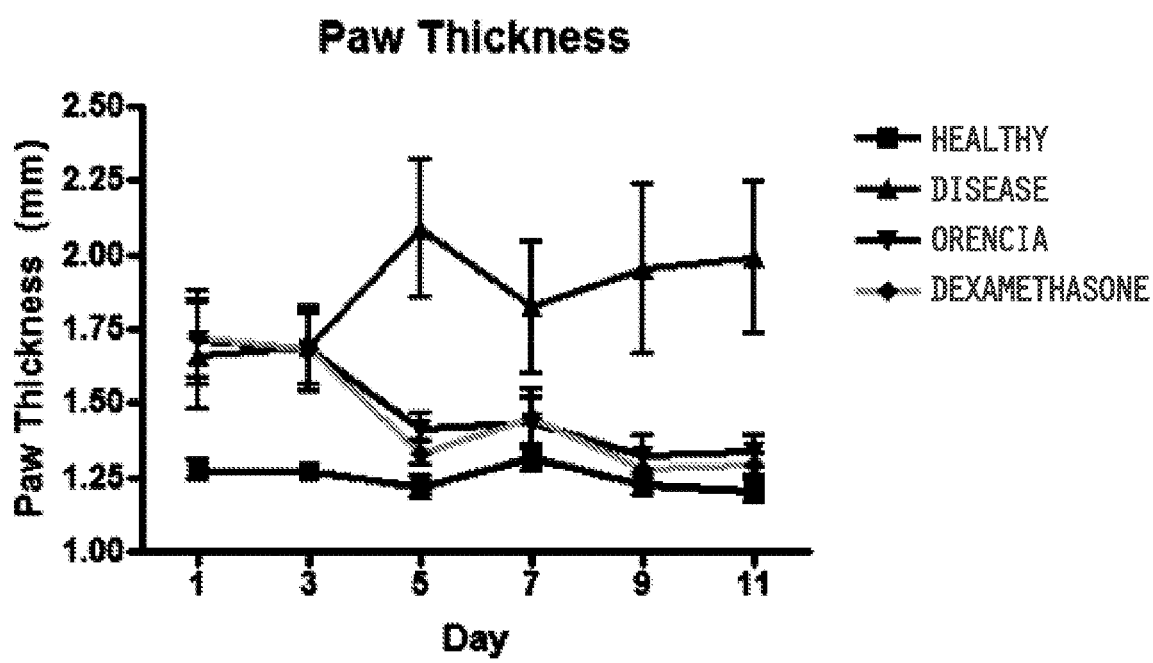
FIG. 16. Analysis of OTL-38 accumulation in CIA mice treated with orencia or dexamethasone. Paw thickness measurements of mice in each of the following treatment groups are shown: healthy control, disease control, orencia, and dexamethasone.
Figure 17:
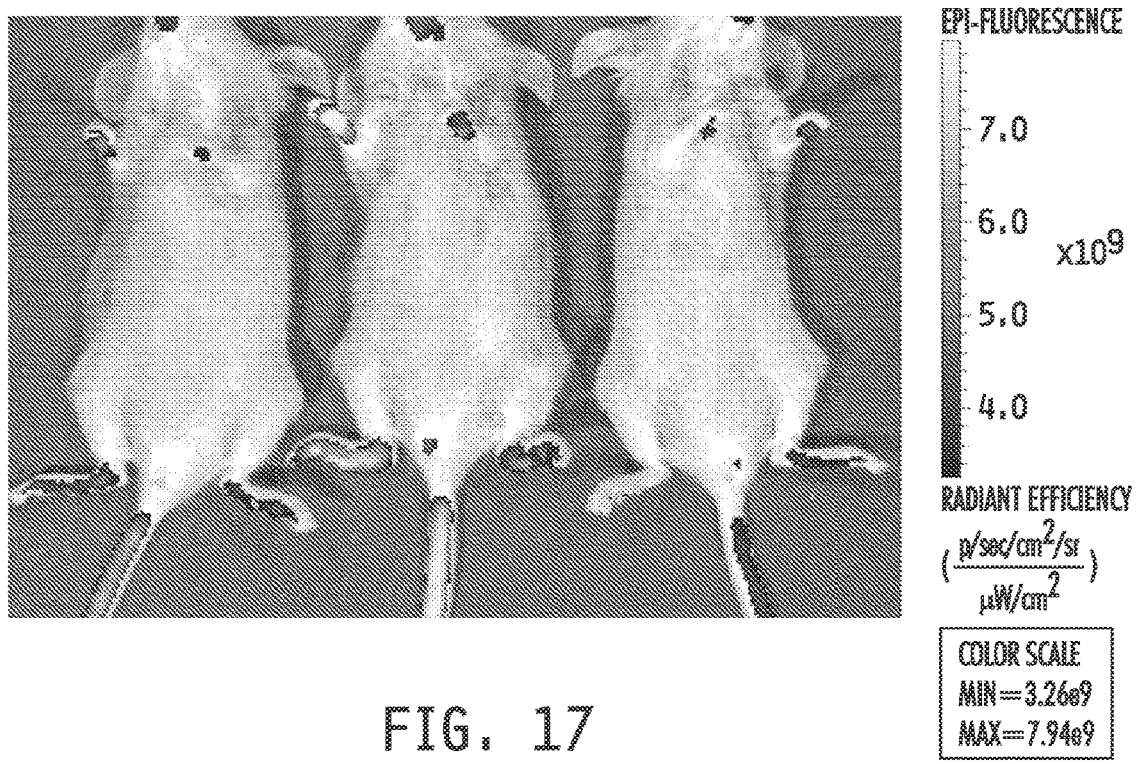
FIG. 17. Analysis of OTL-38 accumulation in CIA mice treated with orencia or dexamethasone. Imaging of mice injected with OTL-38 three days after initiation of treatment is shown: dexamethasone (left), saline (middle) or orencia (right).
Figure 18:
FIG. 18. Analysis of OTL-38 accumulation in CIA mice treated with orencia or dexamethasone. Imaging of mice injected with OTL-38 eleven days after initiation of treatment is shown: dexamethasone (left), saline (middle) or orencia (right).
Figure 19:
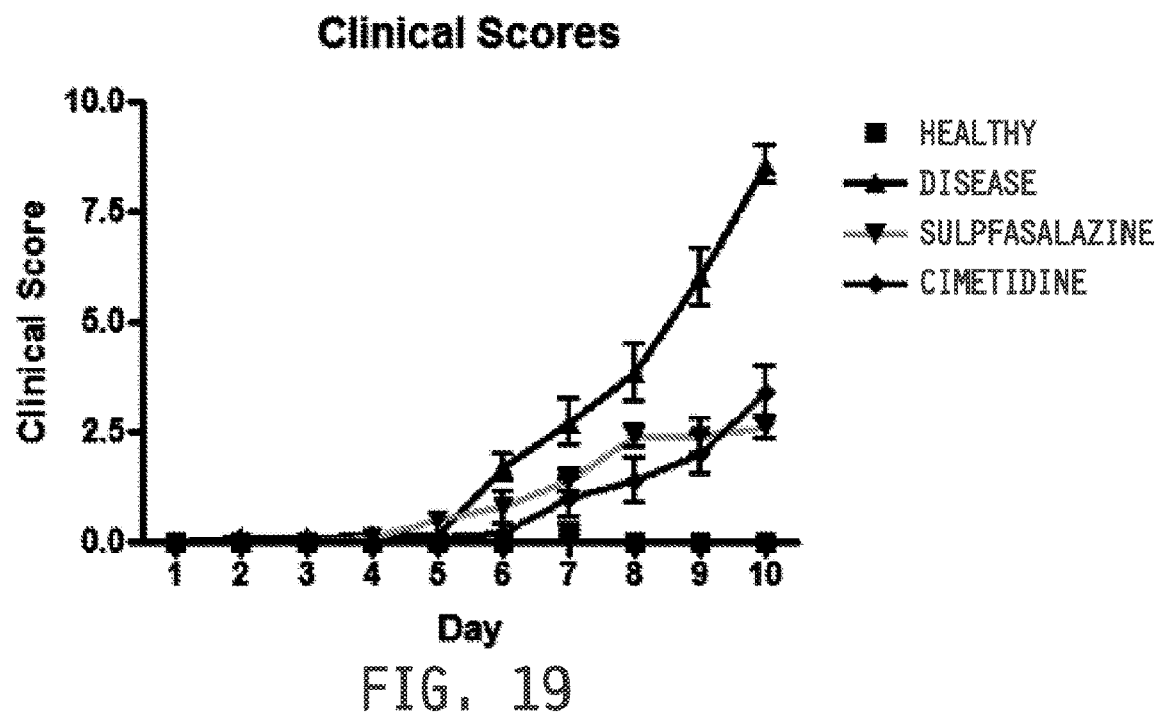
FIG. 19. Analysis of OTL-38 accumulation in mice with ulcerative colitis treated with sulphasalazine or cimetidine. Clinical scores are shown for mice in each of the following treatment groups: healthy control, disease control, sulphasalazine, and cimetidine.
Figure 20:
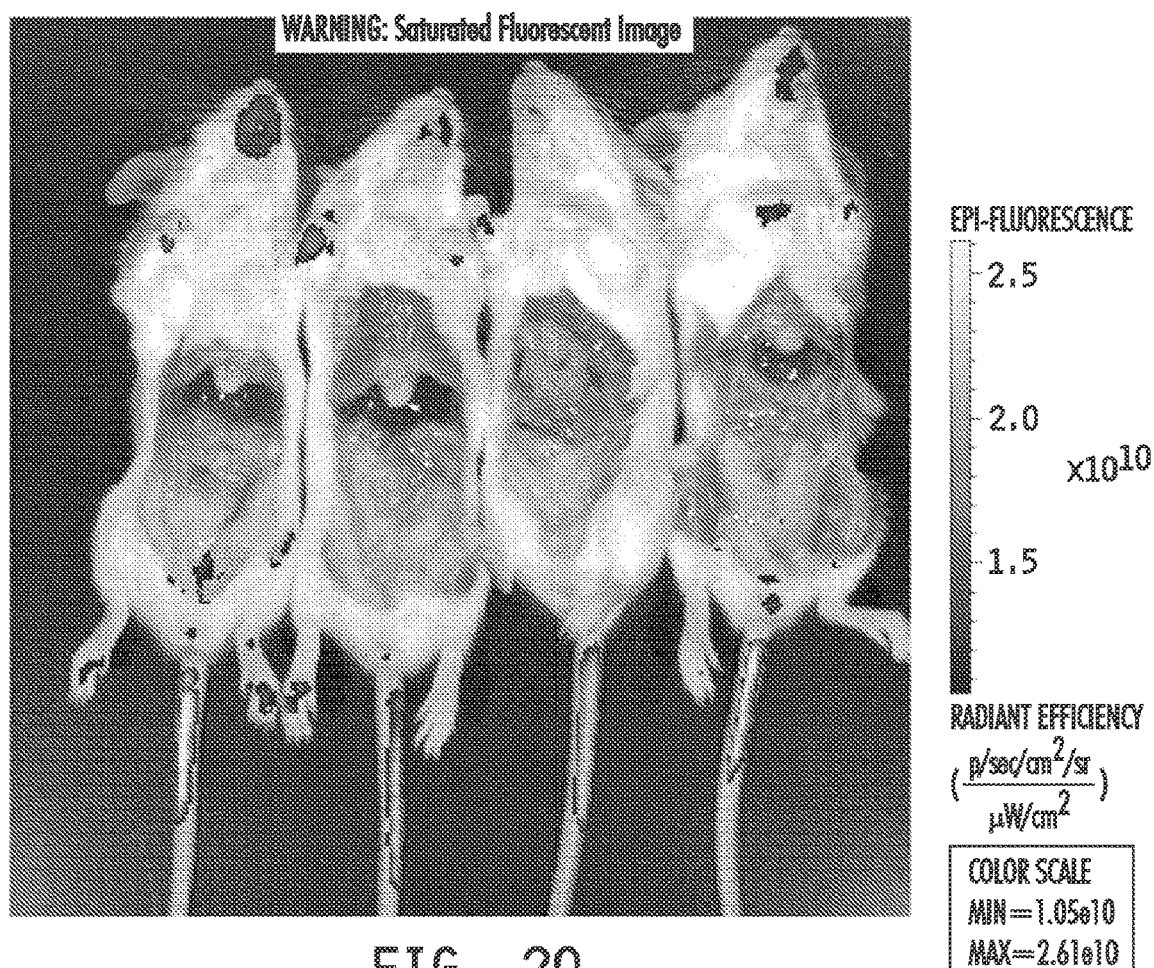
FIG. 20. Analysis of OTL-38 accumulation (Day 4) in mice with ulcerative colitis treated with sulphasalazine or cimetidine. Imaging of mice injected with OTL-38 four days after initiation of treatment is shown: healthy control (far left), disease control (middle left), cimetidine (middle right), and sulphasalazine (far right).
Figure 21:
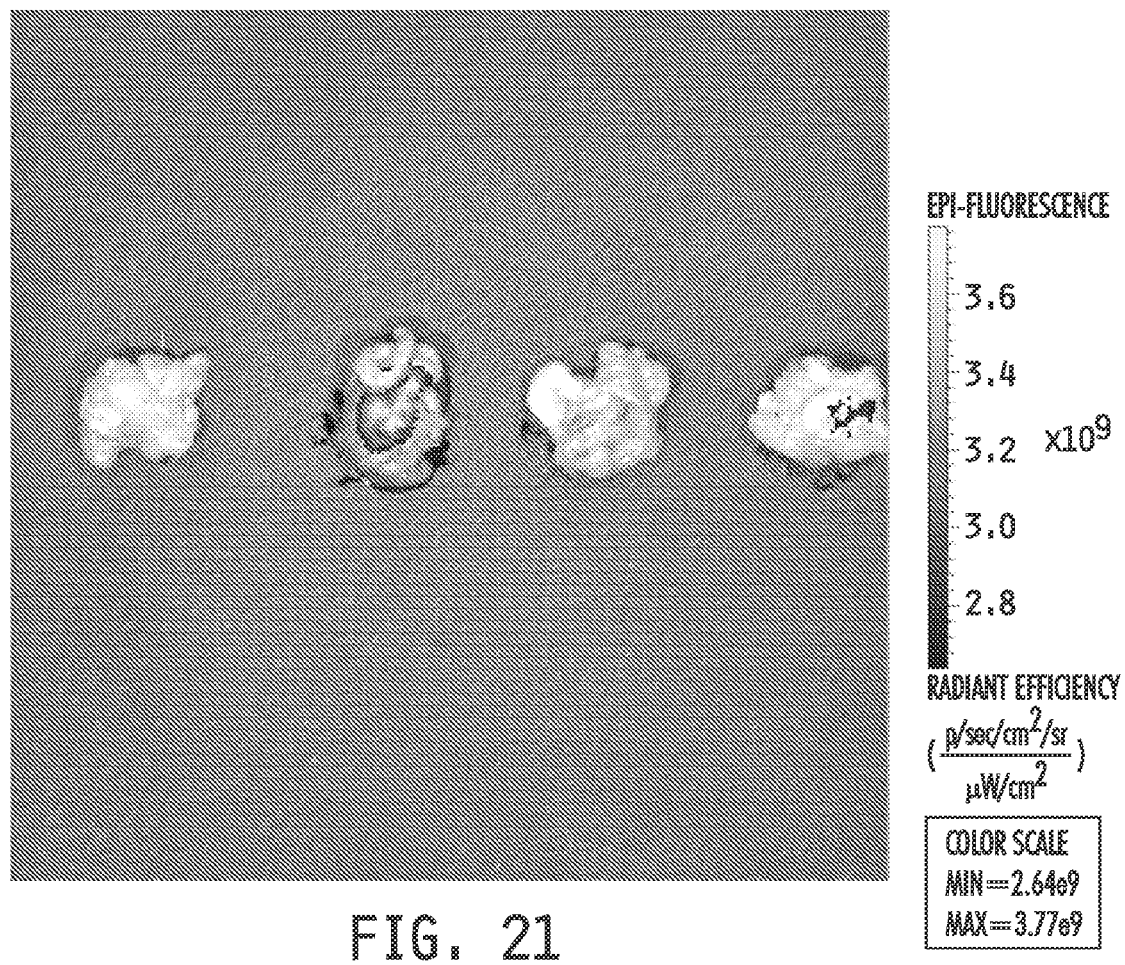
FIG. 21. Analysis of OTL-38 accumulation (Day 4) in mice with ulcerative colitis treated with sulphasalazine or cimetidine. Imaging of colons of mice injected with OTL-38 four days after initiation of treatment is shown: healthy control (far left), disease control (middle left), cimetidine (middle right), and sulphasalazine (far right).
Figure 22:
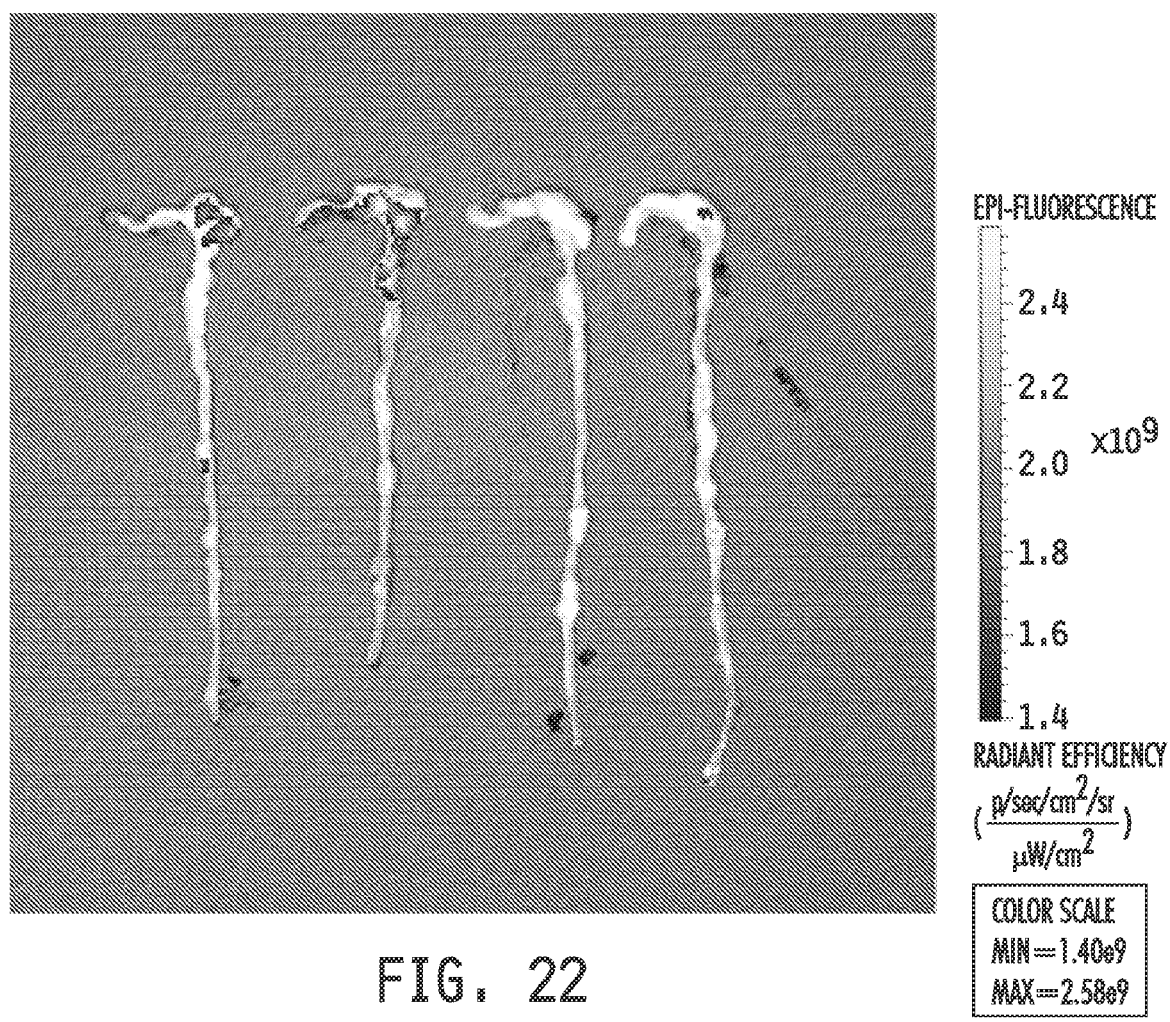
FIG. 22. Analysis of OTL-38 accumulation (Day 4) in mice with ulcerative colitis treated with s sulphasalazine or cimetidine. Imaging of colons of mice injected with OTL-38 four days after initiation of treatment is shown: healthy control (far left), disease control (middle left), cimetidine (middle right), and sulphasalazine (far right).
Figure 23:
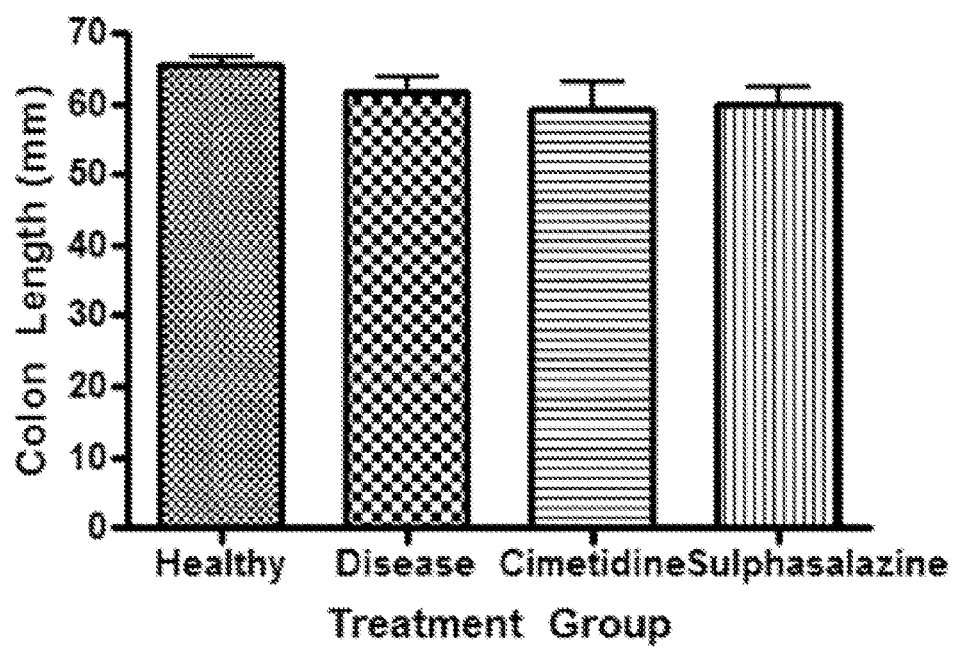
FIG. 23. Analysis of OTL-38 accumulation in mice with ulcerative colitis treated with sulphasazine or cimetidine. Colon length is shown for mice in each of the following treatment groups on day 4 of treatment: healthy control, disease control, sulphasalazine, and cimetidine.
Figure 24:
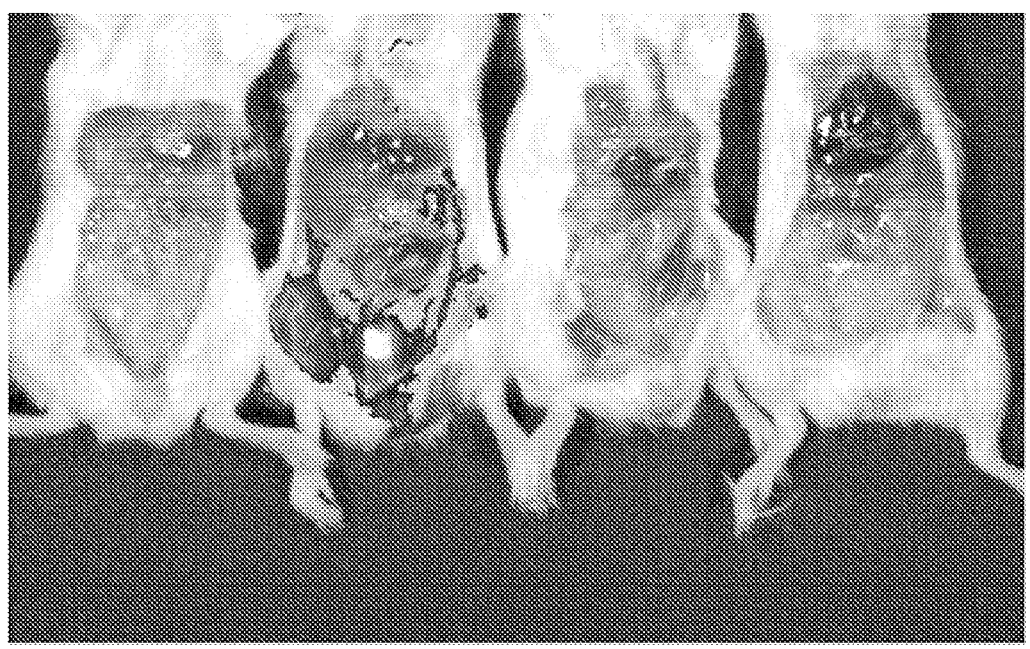
FIG. 24. Analysis of OTL-38 accumulation (Day 10) in mice with ulcerative colitis treated with sulphasalazine or cimetidine. Imaging of mice injected with OTL-38 ten days after initiation of treatment is shown: healthy control (far left), disease control (middle left), cimetidine (middle right), and sulphasalazine (far right).
Figure 25:
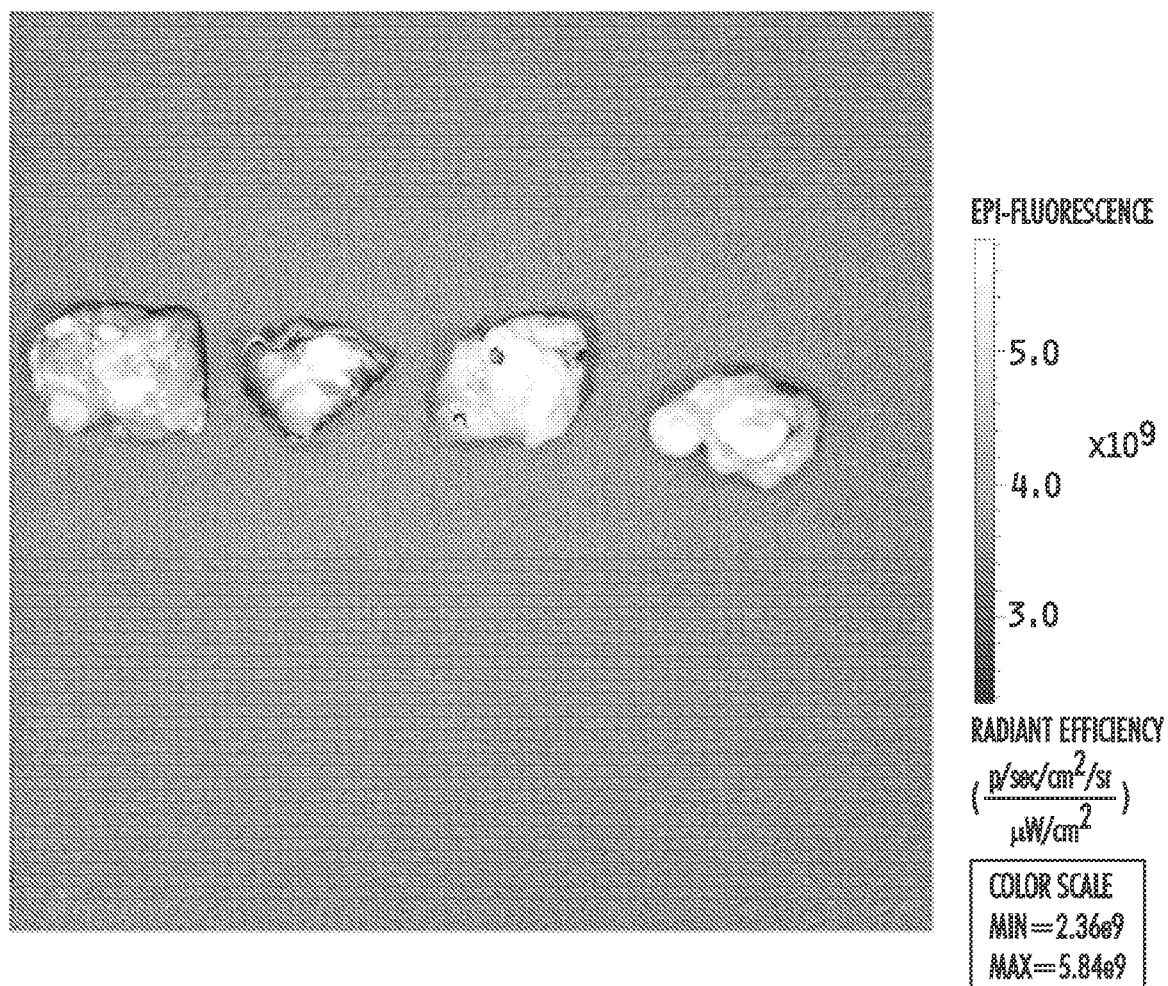
FIG. 25. Analysis of OTL-38 accumulation (Day 10) in mice with ulcerative colitis treated with sulphasalazine or cimetidine. Imaging of colons of mice injected with OTL-38 ten days after initiation of treatment is shown: healthy control (far left), disease control (middle left), cimetidine (middle right), and sulphasalazine (far right).
Figure 26:
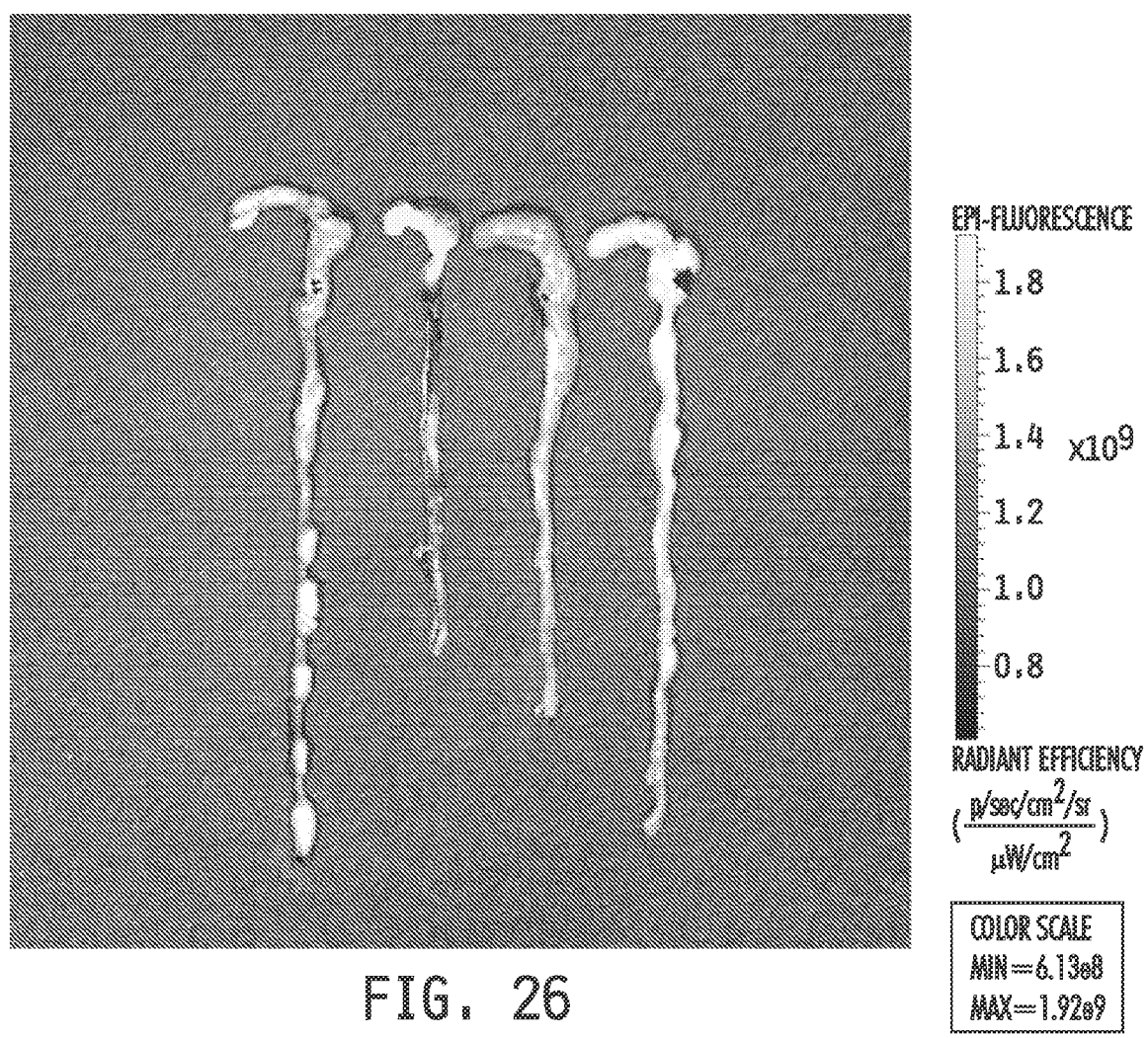
FIG. 26. Analysis of OTL-38 accumulation (Day 10) in mice with ulcerative colitis treated with sulphasalazine or cimetidine. Imaging of colons of mice injected with OTL-38 ten days after initiation of treatment is shown: healthy control (far left), disease control (middle left), cimetidine (middle right), and sulphasalazine (far right).
Figure 27:
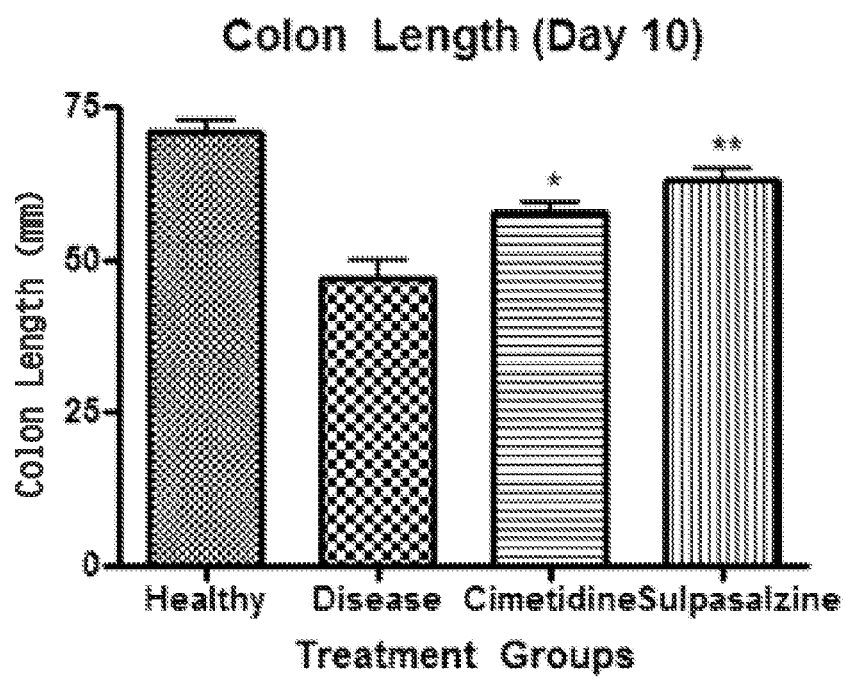
FIG. 27. Analysis of OTL-38 accumulation in mice with ulcerative colitis treated with sulphasalazine or cimetidine. Colon length is shown for mice in each of the following treatment groups on day 10 of treatment: healthy control, disease control, sulphasalazine, and cimetidine.

Treated Mice have Reduced Macrophage Accumulation in a Murine Model of Ulcerative Colitis Ulcerative colitis was induced as described. Seven week old Balb/c mice (Harlan Laboratories) maintained on a folate-deficient diet were administered 5% dextran sodium sulfate (DSS) in their drinking water. Healthy control mice were maintained on normal water. Mice were divided into treatment groups (n=3 per group). Healthy mice and disease control mice received 100 μL saline daily by oral gavage. Diseased mice were treated daily with cimetidine (100 mg/kg) or sulphasalazine (150 mg/kg) by oral gavage. After 4 days of treatment, mice were euthanized and large intestines were removed. Equal weights of the large intestines were digested and made into single cell suspensions. Cells were included with mouse macrophage marker F480-PE and analyzed by flow cytometry. Treated mice were found to have reduced macrophage accumulation compared to the disease control group (FIG. 12).

Example 12

Compound Preparation Method

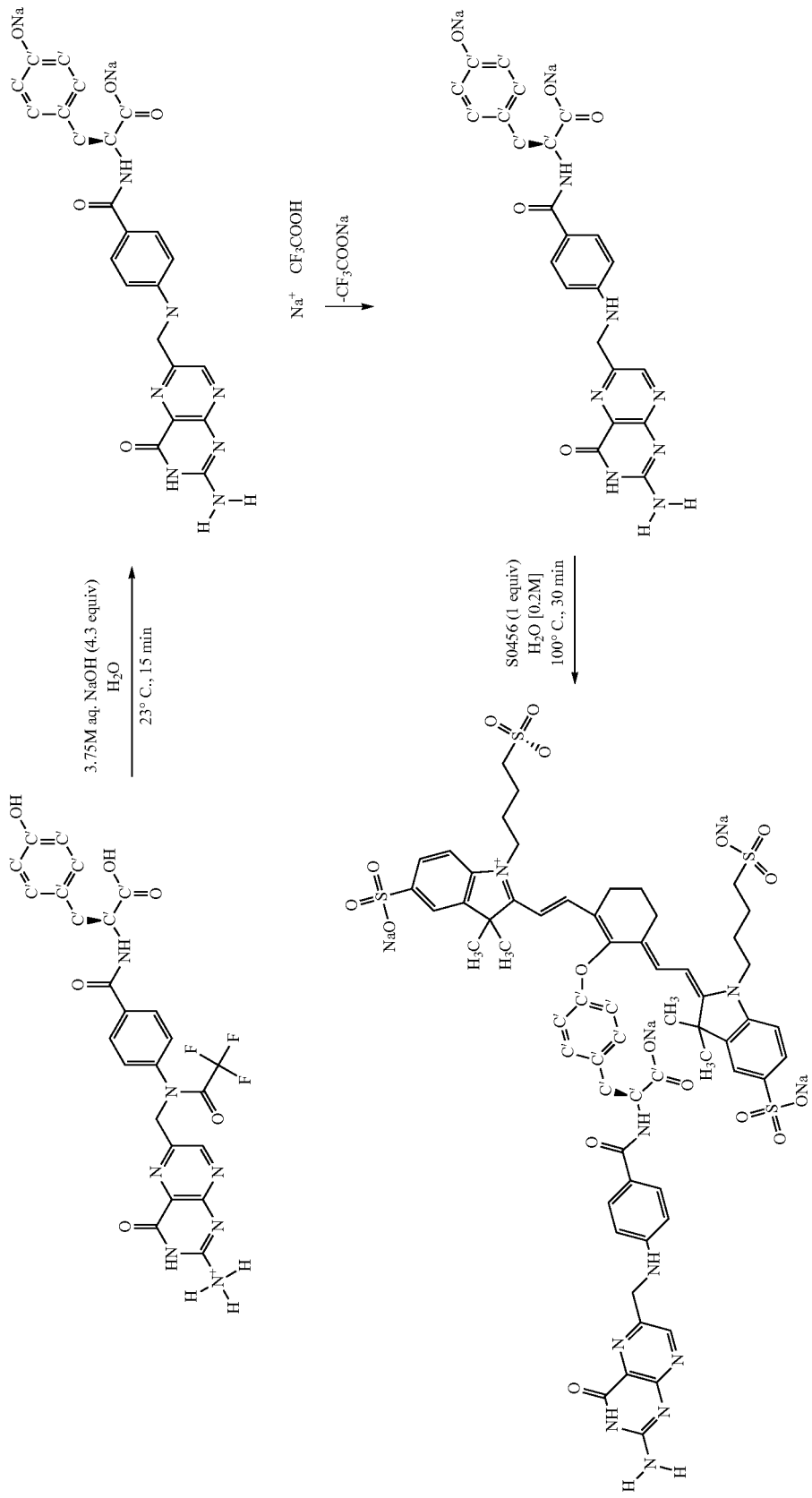

Preparation of Pte-L-Try-S0456 (the final compound as shown above). Fmoc-Tyr($^t$Bu)-Wang Resin was combined with a mixture of piperidine, dichloromethane (DCM), and dimethylformamide (DMF) in a solid phase peptide synthesis vessel. A solution of $N^{10}$-(trifluoroacetyl)pteroic acid, (2-(7-aza-1H-benzotriazole-1-yl)-1,1,3,3-tetramethyluronium hexafluorophosphate) (HATU), Hunig's base (di-isopropylethylamine) and dimethylformamide (DMF) was added to the resin mixture. The resin was washed alternately with dimethylformamide (DMF) and isopropyl alcohol (IPA) and (DCM). The resin product was dried under argon. The TFA-Pte-L-Tyr compound was cleaved from the resin with TFA:H$_2$O:TIPS (95:2.5:2.5). The cleaved product was dried under vacuum conditions. The resulting TFA-Pte-L-Tyr solid was suspended in water with S0456 fluorescent dye (CAS 162093-39-2). The mixture was treated with aqueous sodium hydroxide (NaOH) and heated to 100° C. for 30 min. After the mixture was cooled to room temperature it was added with stirring to acetone to precipitate the Pte-L-Try-S0456. The solid was washed with acetone followed by drying under vacuum conditions. Further purification of the solid product could be accomplished by dissolving the solid in water, filtering the solution, and diluting the solution with i-PrOH. The precipitated solid is collected by filtration, washed sequentially with i-PrOH and acetone, and dried under vacuum conditions.

Example 13

Predicting Response to Treatment in Mice with Arthritis

Collagen-induced arthritis (CIA) was initiated as described above. The mice were treated with etanercept or dexamethasone. On day 3, mice were given an intraperitoneal (i.p.) injection of 10 nmol OTL-38 dye. After 4 hours, mice were anesthetized with isofluorane and imaged on the IVIS Lumina. On day 11, mice were given an i.p. injection of 10 nmol OTL-38 dye. After 4 hours, mice were euthanized and imaged on the IVIS Lumina. Results are shown in FIGS. 13-19.

Example 14

Predicting Response to Treatment in Mice with Ulcerative Colitis

Ulcerative colitis was induced in mice as described above. On day 4, mice were given an intravenous (i.v.) injection of 10 nmol OTL-38 dye. Mice were euthanized after 2 hours. The bladder was emptied and kidneys were removed. On day 10, mice were given an i.v. injection of 10 nmol OTL dye. Mice were euthanized after 2 hours. The bladder was emptied and the kidneys were removed. Results are shown in FIGS. 20-27.

Example 15

Predicting Response to Treatment in Mice with Atherosclerosis

Figure 28:
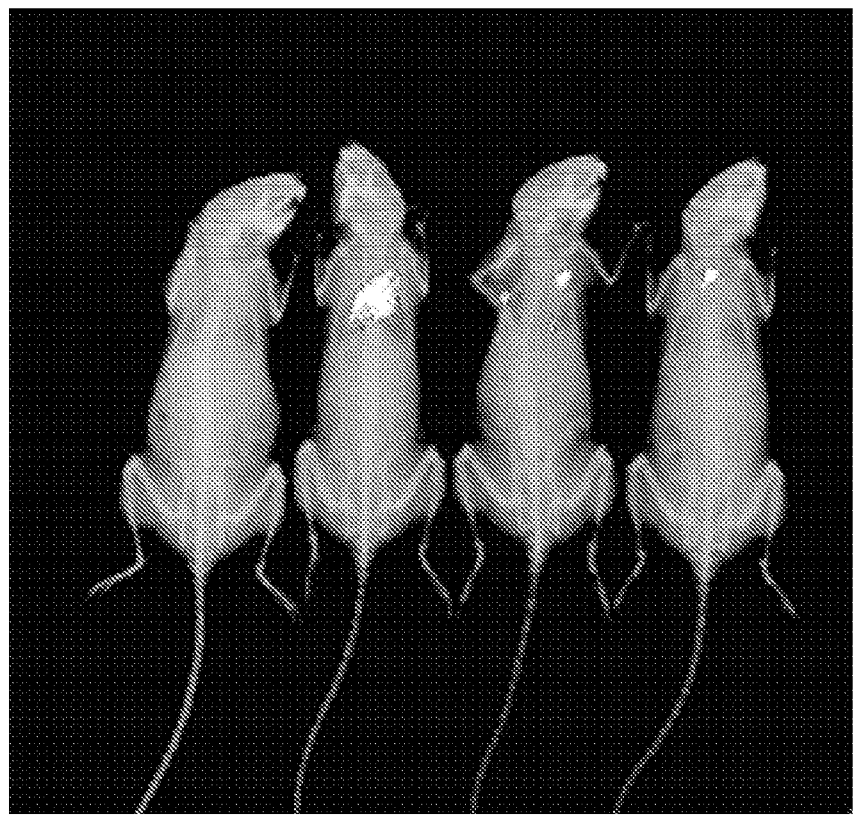
FIG. 28. Analysis of OTL-38 accumulation (Day 21) in mice with atherosclerosis treated with valsartan or fluvastatin. Imaging of mice injected with OTL-38 at 21 days after initiation of treatment is shown: healthy control (far left), disease control (middle left), valsartan (middle right), and fluvastatin (far right).

Atherosclerosis was initiated as described above. The mice were treated with valsartan or fluvastatin. On day 21, mice were given an intraperitoneal (i.p.) injection of 10 nmol OTL-38 dye. After 4 hours, mice were anesthetized with isofluorane and imaged. Results are shown in FIG. 28.

Example 16

Predicting Response to Treatment in Mice with Pulmonary Fibrosis

Figure 29:
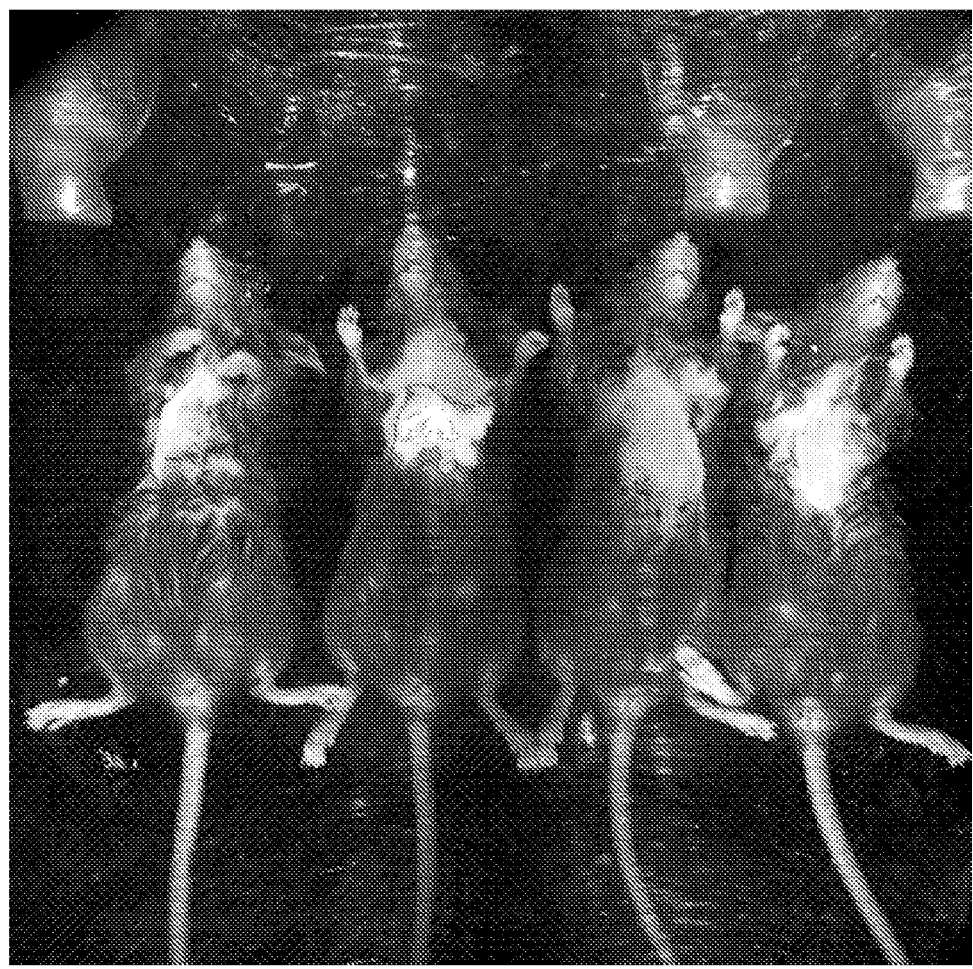
FIG. 29. Analysis of OTL-38 accumulation (Day 6) in mice with pulmonary fibrosis treated with etanercept or dexamethasone. Imaging of mice injected with OTL-38 at 6 days after initiation of treatment is shown: healthy control (far left), disease control (middle left), etanercept (middle right), and dexamethasone (far right).

Pulmonary fibrosis was initiated as described above. The mice were treated with etanercept or dexamethasone. On day 6, mice were given an intraperitoneal (i.p.) injection of 10 nmol OTL-38 dye. After 4 hours, mice were anesthetized with isofluorane and imaged. Results are shown in FIG. 29.

What is claimed is:

1. A method for selecting a patient with arthritis for therapy with an anti-inflammatory drug, the method comprising the steps of:
   (i) administering to the patient a first dose of at least one isomer of a folate-imaging agent conjugate to detect folate-imaging agent conjugate uptake in the patient;
   (ii) detecting the uptake of the first dose of at least one isomer of the folate-imaging agent conjugate in the patient;
   (iii) administering to the patient at least one dose of an anti-inflammatory drug;
   (iv) administering to the patient a second dose of the at least one isomer of a folate-imaging agent conjugate;
   (v) detecting whether there is a reduction in the uptake of the second dose of the at least one isomer of the folate-imaging agent conjugate in comparison to the uptake of the first dose of the at least one isomer of the folate-imaging agent conjugate, wherein a reduction in the uptake of the folate imaging agent conjugate is used to predict that the patient will respond to therapy with the anti-inflammatory drug, whereupon the patient with arthritis is selected for therapy with the anti-inflammatory drug,
   wherein the at least one isomer of a folate-imaging agent conjugate is of the formula:

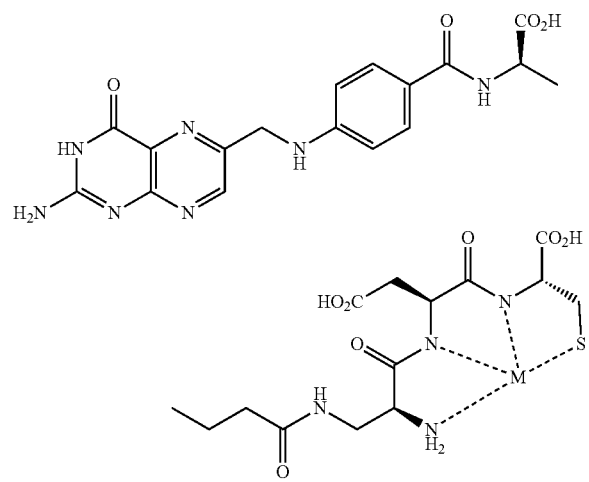

wherein M is a radionuclide, and
wherein the at least one isomer of the folate-imaging agent conjugate produces a detectable signal in the patient.

2. The method of claim 1 wherein the detectable signal is produced as a result of binding of the at least one isomer of a folate-imaging agent conjugate to activated macrophages.

3. The method of claim 1 wherein administering step (i) and administering step (iv) produce a first signal and a second signal, respectively.

4. The method of claim 3 wherein the first signal and the second signal are quantified.

5. The method of claim 3 wherein the first signal is obtained by administering the at least one isomer of a folate-imaging agent conjugate prior to administration of the anti-inflammatory drug, wherein the anti-inflammatory drug is selected from the group consisting of non-steroidal anti-inflammatory drugs (NSAID), analgesics, glucocorticoids, anti-rheumatic drugs, dihydrofolate reductase inhibitors, TNF-α inhibitors, biologic response modifiers, hormonal agents, corticosteroids, hydrocortisone, prednisolone, prednisone, allopurinol, aspirin, indomethacin, phenylbutazone, etanercept, infliximab, adalimumab, rituximab, abatacept, anakinra, efalizumab, methotrexate, dexamethasone, naproxen, and combinations thereof.

6. The method of claim 3 wherein the first signal is obtained by administering the at least one isomer of a folate-imaging agent conjugate on the same day as treatment with the anti-inflammatory drug is initiated.

7. The method of claim 3 wherein the second signal is obtained by administering the at least one isomer of a folate-imaging agent conjugate subsequent to the administration of the anti-inflammatory drug.

8. The method of claim 3 wherein the second signal is obtained by administering the at least one isomer of a folate-imaging agent conjugate within about 21 days after administration of the anti-inflammatory drug is initiated.

9. The method of claim 3 wherein the second signal is obtained by administering the at least one isomer of a folate-imaging agent conjugate within about 1 week, about 2 weeks, about 3 weeks, or about 4 weeks after the administration of the anti-inflammatory drug is initiated.

10. The method of claim 3 wherein the second signal is obtained by administering the at least one isomer of a folate-imaging agent conjugate on any one of the days within about 21 days after the administration of the anti-inflammatory drug is initiated.

11. The method of claim 3 wherein the second signal is obtained by administering the at least one isomer of a folate-imaging agent conjugate on any one of the days within about 12 weeks after the administration of the anti-inflammatory drug is initiated.

12. The method of claim 3 wherein the second signal is reduced by about 10%, about 20%, about 30%, about 40%, about 50%, about 60%, about 70%, about 80%, about 90%, or about 100% compared to the first signal, and wherein the reduction indicates that the patient should continue to be treated with the anti-inflammatory drug.

13. The method of claim 3 wherein the second signal is obtained by administering the at least one isomer of a folate-imaging agent conjugate about 2, about 3, about 4, about 5, about 6, about 12, about 15, or about 21 days after the administration of the anti-inflammatory drug is initiated.

14. A method for selecting a patient with an inflammatory disease for therapy with an anti-inflammatory drug, the method comprising the steps of:
(i) administering to the patient a first dose of at least one isomer of a folate-imaging agent conjugate of the formula:

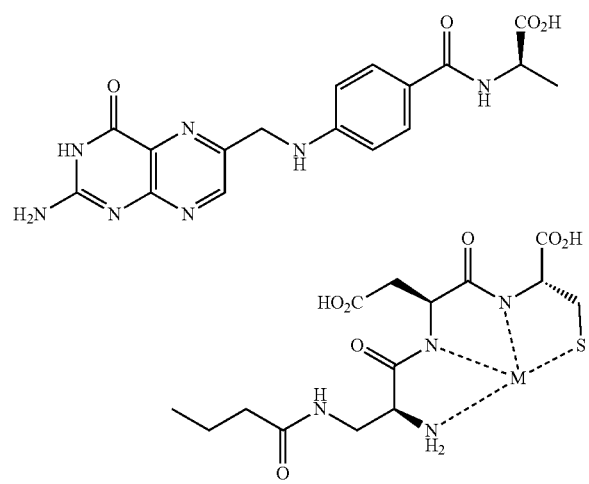

wherein M is $^{99m}$-technetium;
(ii) detecting uptake of the first dose of at least one isomer of the folate-imaging agent conjugate in the patient;
(iii) administering to the patient at least one dose of an anti-inflammatory drug;
(iv) administering to the patient a second dose of the at least one isomer of a folate-imaging agent conjugate;
(v) detecting whether there is a reduction in the uptake of the second dose of the at least one isomer of the folate-imaging agent conjugate in comparison to the uptake of the first dose of the at least one isomer of the folate-imaging agent conjugate, wherein a reduction in the uptake of the folate imaging agent conjugate is used to predict that the patient will respond to therapy with the anti-inflammatory drug, whereupon the patient with the inflammatory disease is selected for therapy with the anti-inflammatory drug,
wherein the inflammatory disease is selected from the group consisting of arthritis, osteoarthritis, rheumatoid arthritis, atherosclerosis, psoriasis, ischemia/reperfusion injury, pulmonary fibrosis, organ transplant rejection, ulcerative colitis, impact trauma, osteomyelitis, multiple sclerosis, scleroderma, Crohn's disease, Sjogren's syndrome, glomerulonephritis, systemic sclerosis, sarcoidosis, an inflammatory lesion, and a chronic inflammation.

15. The method of claim 14, wherein the reduction in the uptake of the folate-imaging agent conjugate in the patient after treatment with the at least one dose of an anti-inflammatory drug relative to the uptake of the folate imaging agent conjugate before treatment with the drug is about 10%, about 20%, about 30%, about 40%, about 50%, about 60%, about 70%, about 80%, about 90%, or about 100%.

16. The method of claim 14, wherein the patient is diagnosed with arthritis.

17. The method of claim 1, wherein the radionuclide is selected from the group consisting of an isotope of gallium, an isotope of indium, an isotope of copper, an isotope of technetium, and an isotope of rhenium.

18. The method of claim 1, wherein the radionuclide is an isotope of technetium.

19. The method of claim 1, wherein the folate-imaging agent conjugate is $^{99}$mTc-EC20.

20. The method of claim 14, wherein the anti-inflammatory drug is selected from the group consisting of: non-steroidal anti-inflammatory drugs (NSAID), analgesics, glucocorticoids, anti-rheumatic drugs, dihydrofolate reductase inhibitors, TNF-α inhibitors, biologic response modifiers, hormonal agents, corticosteroids, hydrocortisone, prednisolone, prednisone, allopurinol, aspirin, indomethacin, phenylbutazone, etanercept, infliximab, adalimumab, rituximab, abatacept, anakinra, efalizumab, methotrexate, dexamethasone, naproxen, and combinations thereof.

* * * * *